United States Patent
Hillebrand et al.

(10) Patent No.: US 6,369,044 B1
(45) Date of Patent: Apr. 9, 2002

(54) TRIAZOLINETHIONE-PHOSPHORIC ACID DERIVATIVES

(75) Inventors: Stefan Hillebrand, Neuss; Bernd-Wieland Krüger, Bergisch Gladbach; Manfred Jautelat, Burscheid; Klaus Stenzel, Düsseldorf; Astrid Mauler-Machnik, Leichlingen; Stefan Dutzmann, Langenfeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/859,779

(22) Filed: May 17, 2001

Related U.S. Application Data

(62) Division of application No. 09/463,270, filed as application No. PCT/EP98/04354 on Jul. 14, 1998, now Pat. No. 6,262,039.

(30) Foreign Application Priority Data

Jul. 25, 1997 (DE) .......................... 197 32 033

(51) Int. Cl.$^7$ .................. A01N 57/32; A01N 57/16; C07F 9/6558
(52) U.S. Cl. ........................... 514/93; 548/111
(58) Field of Search ............... 514/93; 548/111

(56) References Cited

FOREIGN PATENT DOCUMENTS

| DE | 195 20 095 | 12/1996 |
|---|---|---|
| DE | 195 20 096 | 12/1996 |
| DE | 195 20 097 | 12/1996 |
| DE | 195 20 098 | 12/1996 |
| DE | 195 20 593 | 12/1996 |
| DE | 195 20 597 | 12/1996 |
| DE | 195 21 030 | 12/1996 |
| DE | 195 21 487 | 12/1996 |
| DE | 195 28 300 | 2/1997 |
| DE | 195 29 089 | 2/1997 |
| DE | 195 29 091 | 2/1997 |

*Primary Examiner*—Patricia L. Morris
(74) *Attorney, Agent, or Firm*—Joseph C. Gil

(57) ABSTRACT

Novel triazolinethione-phosphoric acid derivatives of the formula

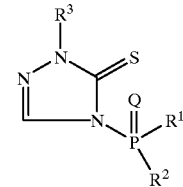

(I)

in which

R$^1$, R$^2$, R$^3$ and Q are each as defined in the description and their metal salt complexes, a process for preparing the novel substances and their use as microbicides in crop protection and in the protection of materials are described.

4 Claims, No Drawings

TRIAZOLINETHIONE-PHOSPHORIC ACID DERIVATIVES

This application is a division of application Ser. No. 09/463,270 filed Jan. 1, 2000, now U.S. Pat. No. 6,262,039, which is a 371 of PCT/EP98/04354, filed Jul. 14, 1998.

The present invention relates to novel triazolinethione-phosphoric acid derivatives, to a process for their preparation and to their use as microbicides.

It is already known that numerous alkylthio-triazolyl derivatives have fungicidal properties (cf. WO 96-16 048). Thus, for example, 2-(1-chlorocyclopropyl)-1-(2-chlorophenyl)-3-(5-methylthio-1,2,4-triazol-1-yl)-propan-2-ol can be employed for controlling fungi. The activity of this substance is good, but it is sometimes unsatisfactory at low application rates.

This invention, accordingly, provides novel triazolinethione-phosphoric acid derivatives of the formula

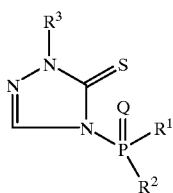

(I)

in which $R^1$ and $R^2$ independently of one another each represent alkyl, halogenoalkyl, alkoxy, alkoxyalkoxy, halogenoalkoxy, alkoxyalkyl, alkylthio, alkenylthio, alkinylthio, cycloalkyl, cycloalkylthio, optionally substituted phenyl, optionally substituted phenylalkyl having 1 to 4 carbon atoms in the alkyl moiety, optionally substituted phenoxy, optionally substituted phenylthio, optionally substituted phenylalkoxy having 1 to 4 carbon atoms in the alkoxy moiety, optionally substituted heteroaryl or represent a radical of the formula

in which $R^4$ represents hydrogen or alkyl and $R^5$ represents alkyl, optionally substituted phenylalkyl having 1 to 4 carbon atoms in the alkyl moiety or represents optionally substituted phenyl or $R^4$ and $R^5$ together represent an alkylene chain having 4 or 5 carbon atoms or represent a radical of the formula
—CH$_2$—CH$_2$—O—CH$_2$—CH$_2$— or

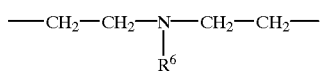

in which $R^6$ represents hydrogen or alkyl having 1 to 4 carbon atoms, $R^3$ represents a radical of the formula

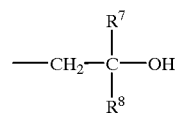

in which $R^7$ and $R^8$ are identical or different and each represent optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl, or $R^3$ represents a radical of the formula

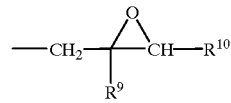

in which $R^9$ represents alkyl having 1 to 4 carbon atoms, halogenoalkyl having 1 to 4 carbon atoms and 1 to 5 halogen atoms, optionally halogen-substituted cycloalkyl having 3 to 7 carbon atoms, naphthyl or represents phenyl which is optionally mono- to trisubstituted by identical or different substitutents from the group consisting of halogen, nitro, phenyl, phenoxy, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkythio having 1 to 4 carbon atoms and 1 to 5 halogen atoms, and $R^{10}$ represents phenyl which is optionally mono- to trisubstituted by identical or different substitutents from the group consisting of halogen, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms, or $R^3$ represents a radical of the formula

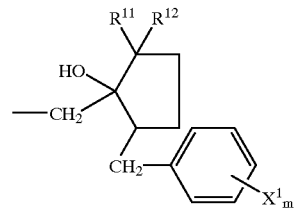

in which $R^{11}$ and $R^{12}$ independently of one another each represent hydrogen or alkyl having 1 to 6 carbon atoms, $X^1$ represents halogen, alkyl having 1 to 5 carbon atoms, alkoxy having 1 to 4 carbon atoms, phenyl, phenoxy, halogenoalkyl having 1 to 4 carbon atoms and 1 to 5 halogen atoms, halogenoalkoxy having 1 to 4 carbon atoms and 1 to 5 halogen atoms or represents halogenoalkylthio having 1 to 4 carbon atoms and 1 to 5 halogen atoms, and m represents the numbers 0, 1 or 2, or $R^3$ represents a radical of the formula

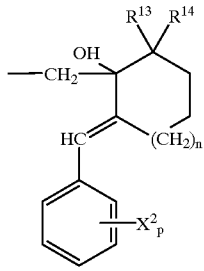

in which $R^{13}$ and $R^{14}$ independently of one another each represent hydrogen or alkyl having 1 to 6 carbon atoms, $X^2$ represents halogen, cyano, nitro, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms or phenyl, n represents the numbers 0, 1 or 2 and p represents the numbers 0, 1 or 2, or $R^3$ represents a radical of the formula

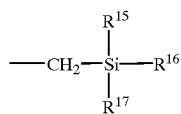

in which $R^{15}$ represents alkyl having 2 to 18 carbon atoms, cycloalkyl having 3 to 6 carbon atoms, naphthyl or the radical of the formula

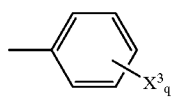

in which $X^3$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and q represents the numbers 0, 1 or 2, $R^{16}$ and $R^{17}$ independently of one another each represent alkyl having 1 to 6 carbon atoms, alkoxy having 1 to 6 carbon atoms, cycloalkyl having 3 to 6 carbon atoms or represent the radical of the formula

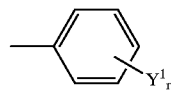

in which $Y^1$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and r represents the numbers 0, 1 or 2, or $R^3$ represents a radical of the formula

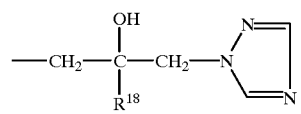

in which $R^{18}$ represents alkyl having 1 to 6 carbon atoms, halogenoalkyl having 1 to 6 carbon atoms and 1 to 5 halogen atoms, cycloalkyl having 3 to 6 carbon atoms which is optionally substituted by halogen and/or alkyl having 1 to 4 carbon atoms, optionally substituted aryl or represents optionally substituted aralkyl, or $R^3$ represents a radical of the formula

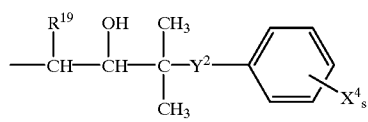

in which $R^{19}$ represents hydrogen, alkyl or optionally substituted cycloalkyl, $X^4$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, s represents the numbers 0, 1, 2 or 3 and $Y^2$ represents an oxygen atom, a $CH_2$ group or a direct bond, or $R^3$ represents a radical of the formula

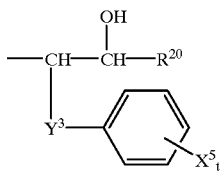

in which $R^{20}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted benzyl, $X^5$ represents halogen, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, t represents the numbers 0, 1, 2 or 3 and $Y^3$ represents an oxygen atom or represents a $CH_2$ group, or $R^3$ represents a radical of the formula

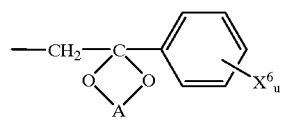

in which

A represents alkanediyl having 2 or 3 carbon atoms which is optionally substituted by halogen and/or alkyl having 1 to 4 carbon atoms, $X^6$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, and u represents the numbers 0, 1, 2 or 3, or $R^3$ represents a radical of the formula

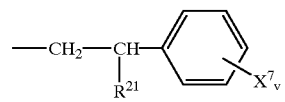

in which $R^{21}$ represents alkyl having 1 to 10 carbon atoms, halogenoalkyl having 1 to 6 carbon atoms and 1 to 5 halogen atoms, fluoroalkoxyalkyl having 1 to 4 carbon atoms in the fluoroalkoxy moiety and 1 to 4 carbon atoms in the alkyl moiety, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted phenylalkyl having 1 to 4 carbon atoms in the alkyl moiety, $X^7$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, and v represents the numbers 0, 1, 2 or 3, or $R^3$ represents a radical of the formula

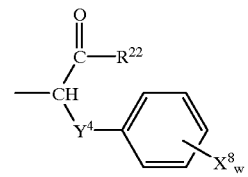

in which $R^{22}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted benzyl, $X^8$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, w represents the numbers 0, 1, 2 or 3 and $Y^4$ represents an oxygen atom or represents a $CH_2$ group, or $R^3$ represents a radical of the formula

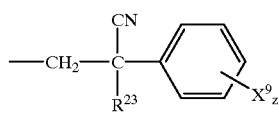

in which
  $R^{23}$ represents alkyl having 1 to 6 carbon atoms, halogenoalkyl having 1 to 6 carbon atoms and 1 to 5 halogen atoms, optionally substituted aryl or represents optionally substituted aralkyl,
  $X^9$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and
  z represents the numbers 0, 1, 2 or 3 and
Q represents oxygen or sulphur,
and their metal salt complexes.

Numerous substances according to the invention contain one or more asymmetrically substituted carbon atoms. They can therefore be obtained in the form of optical isomers. The present invention relates both to the individual isomers and to their mixtures.

Furthermore, it has been found that triazolinethione-phosphoric acid derivatives of the formula (I) and their metal salt complexes are obtained when triazolinethiones of the formula

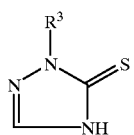

(II)

in which
  $R^3$ is as defined above, are reacted with phosphoric acid derivatives of the formula

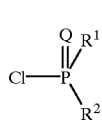

(III)

in which
  $R^1$, $R^2$ and Q are each as defined above in the presence of an acid binder and, if appropriate, in the presence of a diluent and, if appropriate, a metal salt is subsequently added to the resulting compounds of the formula (I).

Finally, it has been found that the novel triazolinethione-phosphoric acid derivatives of the formula (I) and their metal salt complexes have very good microbicidal properties and can be used both in crop protection and in the protection of materials for controlling undesirable microorganisms.

Surprisingly, the substances according to the invention have better microbicidal activity, in particular fungicidal activity, then 2-(1-chloro-cyclopropyl)-1-(2-chlorophenyl)-3-(5-methylthio-1,2,4-triazol-1-yl)-propan-2-ol, which is a constitutionally similar active compound of the prior art having the same direction of action.

The formula (I) provides a general definition of the triazolinethione-phosphoric acid derivatives according to the invention.
  $R^1$ preferably represents straight-chain or branched alkyl having 1 to 6 carbon atoms, cycloalkyl having 3 to 6 carbon atoms, straight-chain or branched alkoxy having 1 to 6 carbon atoms, alkoxyalkoxy having 1 to 4 carbon atoms in each alkoxy moiety, alkoxyalkyl having 1 to 4 carbon atoms in the alkoxy moiety and 1 to 4 carbon atoms in the alkyl moiety,
  or represents phenyl which may be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano,
  or represents phenylalkyl having 1 to 2 carbon atoms in the alkyl moiety, where the phenyl moiety may be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano,
  or represents phenoxy which may be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano,
  or represents phenylalkoxy having 1 or 2 carbon atoms in the alkoxy moiety, where the phenyl moiety may be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano,
  or represents a five- or six-membered heteroaromatic radical having 1 or 2 heteroatoms, such as nitrogen, sulphur and/or oxygen, where each of these radicals may be mono- or disubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical halogen atoms, halogenoalkoxy having 1 to 4 carbon atoms and 1 to 5 identical or different halogen atoms, phenyl, nitro and cyano,
or
$R^1$ represents a radical of the formula

in which
  $R^4$ preferably represents hydrogen or alkyl having 1 to 4 carbon atoms and R⁵ preferably represents alkyl having 1 to 6 carbon atoms or represents phenylalkyl having 1 or 2 carbon atoms in the alkyl moiety, where the phenyl moiety may be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical of different halogen atoms, halogenoalkoxy having 1 to 4 carbon atoms and 1 to 5 identical or different halogen atoms, phenyl, nitro and cyano, or R⁵ preferably represents phenyl which may be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano, or R⁴ and R⁵ together represent an alkylene chain having 4 or 5 carbon atoms or represent a radical of the formula
—CH₂—CH₂—O—CH₂—CH₂— or

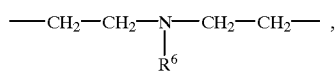

in which

R⁶ represents hydrogen, methyl or ethyl.

R² preferably represents straight-chain or branched alkoxy having 1 to 6 carbon atoms, cycloalkoxy having 3 to 6 carbon atoms, alkoxyalkoxy having 1 to 4 carbon atoms in each alkoxy moiety or represents phenoxy which may be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano, or represents phenylalkoxy having 1 or 2 carbon atoms in the alkoxy moiety, where the phenyl moiety may be mono- to trisubstituted by identical or different substituents from the group consisting of halogen, alkyl having 1 to 4 carbon atoms, alkoxy having 1 to 4 carbon atoms, halogenoalkoxy having 1 to 4 carbon atoms and 1 to 5 identical or different halogen atoms, halogenoalkoxy having 1 to 4 carbon atoms and 1 to 5 identical or different halogen atoms, phenyl, nitro and cyano, or represents five- or six-membered heteroaryloxy having 1 or 2 heteroatoms, such as nitrogen, sulphur and/or oxygen, in the heterocycle, where each of these radicals may be mono- or disubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano.

R³ preferably represents a radical of the formula

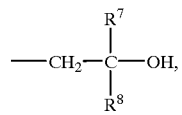

in which

R⁷ preferably represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, represents aralkenyl having 6 to 10 carbon atoms in the aryl moiety and 2 to 4 carbon atoms in the alkenyl moiety, where the aryl moiety may in each case be mono- to trisubstituted by identical or different substitutents from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 to 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused, five- or six-membered heteroaromatic radical having 1 to 3 heteroatoms, such as nitrogen, sulphur and/or oxygen, where each of these radicals may be mono- to trisubstituted by identical or different radicals from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 to 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in alkoxy moiety and 1 to 3 carbon atoms in alkyl moiety, nitro and cyano, and $R^8$ preferably represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, where each of these radicals may be mono- to trisubstituted by identical or different substituents from the group consisting of halogen, alkoxy having 1 to 4 carbon atoms cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 identical or different halogen atoms, halogenoalkoxy having 1 to 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoxyiminoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may in each case be mono- to trisubstituted by identical or different substitutents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoxyiminoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoxyiminoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused, five- or six-membered hetero-aromatic radical having 1 to 3 heteroatoms, such as nitrogen, sulphur and/or oxygen, where each of these radicals may be mono- to trisubstituted by identical or different radicals from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in alkoxy moiety and 1 to 3 carbon atoms in alkyl moiety, nitro and cyano.

$R^3$ furthermore preferably represents a radical of the formula

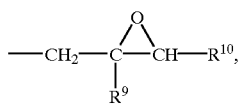

in which
$R^9$ preferably represents methyl, ethyl, n-propyl, isopropyl, n-butyl, sec-butyl, iso-butyl, tert-butyl, fluoro-tert-butyl, difluoro-tert-butyl, cycloalkyl having three to six carbon atoms which is optionally mono- to trisubstituted by identical or different substituents from the group consisting of fluorine, chlorine and bromine, represents naphthyl or represents phenyl which may be mono- to trisubstituted by identical or different substituents from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and trifluoromethylthio, and $R^{10}$ preferably represents phenyl which may be mono- to trisubstituted by identical or different substituents from the group consisting of fluorine, chlorine, bromine, methyl, ethyl, ispropyl, tert-butyl, methoxy, ethoxy, trifluoromethyl, trichloromethyl, difluoromethyl, difluorochloromethyl, trifluoromethoxy, difluoromethoxy and trifluoromethylthio.

$R^3$ furthermore preferably represents a radical of the formula

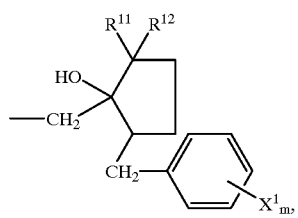

in which
$R^{11}$ preferably represents hydrogen, methyl, ethyl, n-propyl, isopropyl, n-butyl, iso-butyl, sec-butyl, tert-butyl or n-pentyl,
$R^{12}$ preferably represents hydrogen, methyl, ethyl, n-propyl, isopropyl, n-butyl, iso-butyl, sec-butyl, tert-butyl or n-pentyl, $X^1$ preferably represents fluorine, chlorine, bromine, methyl, ethyl, n-propyl, isopropyl, n-butyl, iso-butyl, sec-butyl, tert-butyl, methoxy, ethoxy, phenyl, phenoxy, trichloromethyl, trifluoromethyl, trifluoromethoxy, difluoromethoxy or trifluoromethyl and
m also preferably represents the numbers 0, 1 or 2, where
$X^1$ may represent identical or different radicals if m represents 2.

$R^3$ furthermore preferably represents a radical of the formula

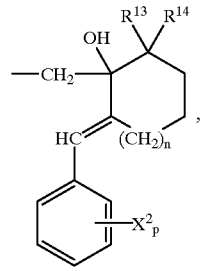

in which
$R^{13}$ preferably represents hydrogen, methyl, ethyl, n-propyl, isopropyl, n-butyl, iso-butyl, sec-butyl, tert-butyl or n-pentyl,
$R^{14}$ preferably represents hydrogen, methyl, ethyl, n-propyl, isopropyl, n-butyl, iso-butyl, sec-butyl, tert-butyl or n-pentyl,
$X^2$ preferably represents fluorine, chlorine, bromine, cyano, nitro, methyl, ethyl, n-propyl, isopropyl, n-butyl, iso-butyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl,
n also preferably represents the numbers 0 or 1 and
p also preferably represents the numbers 0, 1 or 2, where
$X^2$ may represent identical or different radicals if p represents 2.

$R^3$ furthermore preferably represents a radical of the formula

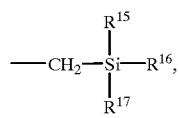

in which
$R^{15}$ preferably represents alkyl having 2 to 12 carbon atoms, cycloalkyl having 5 or 6 carbon atoms or represents a radical of the formula

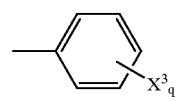

in which
$X^3$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy and q also preferably represents the numbers 0, 1 or 2, where $X^3$ represents identical or different radicals if q represents 2, $R^{16}$ preferably represents alkyl having 1 to 4 carbon atoms or represents the radical of the formula

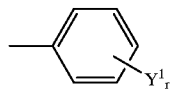

in which
$Y^1$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy and r also preferably represents the numbers 0, 1 or 2, where $Y^1$ represents identical or different radicals if r represents 2, and $R^{17}$ preferably represents alkyl having 1 to 4 carbon atoms.

$R^3$ furthermore preferably represents a radical of the formula

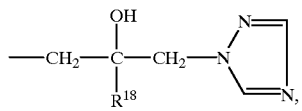

in which
$R^{18}$ preferably represents straight-chain or branched alkyl having 1 to 4 carbon atoms, straight-chain or branched halogenoalkyl having 1 to 4 carbon atoms and 1 to 5 fluorine, chlorine and/or bromine atoms, represents cycloalkyl having 3 to 6 carbon atoms which is optionally mono- to trisubstituted by identical or different substituents from the group consisting of fluorine, chlorine, bromine, methyl and ethyl, represents phenyl, benzyl or phenethyl, where each of the three last-mentioned radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or phenoxy which is optionally substituted by halogen and/or alkyl having 1 to 4 carbon atoms.

$R^3$ furthermore preferably represents a radical of the formula

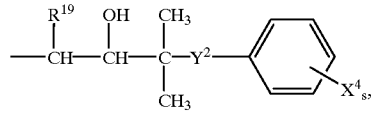

in which
$R^{19}$ preferably represents hydrogen, straight-chain or branched alkyl having 1 to 12 carbon atoms or represents cycloalkyl having 3 to 7 carbon atoms which is optionally mono- to trisubstituted by identical or different substituents from the group consisting of halogen and alkyl having 1 to 4 carbon atoms, $X^4$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy, s preferably represents the numbers 0, 1, 2 or 3, where $X^4$ represents identical or different radicals if s represents 2 or 3, and $Y^2$ preferably represents an oxygen atom, a $CH_2$ group or a direct bond.

$R^3$ furthermore preferably represents a radical of the formula

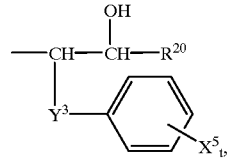

in which
$R^{20}$ preferably represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents from the group consisting of fluorine, chlorine, bromine, methyl and ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents from the group consisting of fluorine, chlorine and bromine or represents benzyl which is optionally mono- to trisubstituted by identical or different substituents from the group consisting of fluorine, chlorine and bromine, $X^5$ preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents from the group consisting of fluorine, chlorine, bromine and methyl or represents phenoxy which is optionally mono- or disubstituted by identical or different substituents from the group consisting of fluorine, chlorine, bromine and methyl, t preferably represents the numbers 0, 1, 2 or 3, where $X^5$ represents identical or different radicals if t represents 2 or 3 and $Y^3$ preferably represents an oxygen atom or represents a $CH_2$ group.

$R^3$ furthermore preferably represents a radical of the formula

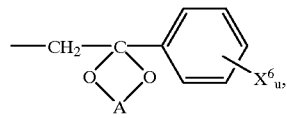

in which
A preferably represents alkanediyl having 2 or 3 carbon atoms which is optionally mono- to trisubstituted by identical or different substituents from the group consisting of fluorine, chlorine, bromine, methyl, ethyl, n-propyl, isopropyl, n-butyl, i-butyl, sec-butyl and tert-butyl, $X^6$ preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally mono- to trisubstituted by identical or different substituents from the group consisting of fluorine, chlorine and methyl or represents phenoxy which is optionally mono- to trisubstituted by identical or different substituents from the group consisting of fluorine, chlorine and methyl and u preferably represents the numbers 0, 1, 2 or 3, where $X^6$ represents identical or different radicals if u represents 2 or 3.

$R^3$ furthermore preferably represents a radical of the formula

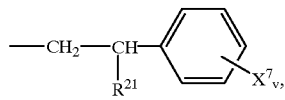

in which $R^{21}$ preferably represents straight-chain or branched alkyl having 1 to 6 carbon atoms, straight-chain or branched halogenoalkyl having 1 to 6 carbon atoms and 1 to 5 fluorine, chlorine and/or bromine atoms, fluoroalkoxyalkyl having 1 to 3 carbon atoms and 1 to 5 fluorine atoms in the fluoroalkoxy moiety and 1 to 3 carbon atoms in the alkyl moiety, cycloalkyl which is optionally mono- to trisubstituted by identical or different substituents from the group consisting of fluorine, chlorine, bromine, methyl and ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents from the group consisting of fluorine, chlorine and bromine or phenylalkyl having 1 or 2 carbon atoms in the alkyl moiety which is optionally mono- to trisubstituted by identical or different substituents from the group consisting of fluorine, chlorine and bromine, $X^7$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents from the group consisting of fluorine, chlorine, bromine and methyl or represents phenoxy which is optionally mono- or disubstituted by identical or different substituents from the group consisting of fluorine, chlorine, bromine and methyl and v preferably represents the numbers 0, 1, 2 or 3, where $X^7$ represents identical or different radicals if v represents 2 or 3.

$R^3$ furthermore preferably represents a radical of the formula

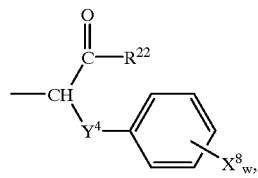

in which $R^{22}$ preferably represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents from the group consisting of fluorine, chlorine, bromine, methyl and ethyl, cycloalkylalkyl having 3 to 6 carbon atoms in the cycloalkyl moiety and 1 to 3 carbon atoms in alkyl moiety, phenyl which is optionally mono- to trisubstituted by identical or different substituents from the group consisting of fluorine, chlorine and bromine or represents benzyl which is optionally mono- to trisubstituted by identical or different substituents from the group consisting of fluorine, chlorine and bromine, $X^8$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents from the group consisting of fluorine, chlorine, bromine and methyl or represents phenoxy which is optionally mono- or disubstituted by identical or different substituents from the group consisting of fluorine, chlorine, bromine and methyl, w preferably represents the numbers 0, 1, 2 or 3, where $X^8$ represents identical or different radicals if w represents 2 or 3, and $Y^4$ preferably represents an oxygen atom or represents a $CH_2$ group.

$R^3$ moreover also preferably represents a radical of the formula

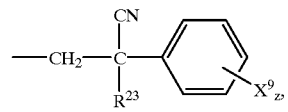

in which $R^{23}$ preferably represents straight-chain or branched alkyl having 1 to 4 carbon atoms, halogenoalkyl having 1 to 4 carbon atoms and 1 to 5 halogen atoms, phenyl which is optionally mono- to trisubstituted by identical or different substituents from the group consisting of halogen, alkyl having 1 to 4 carbon atoms, halogenoalkyl having 1 or 2 carbon atoms having 1 to 5 halogen atoms, alkoxy having 1 to 4 carbon atoms and halogenoalkoxy having 1 or 2 carbon atoms and 1 to 5 halogen atoms or represents phenylalkyl having 1 to 4 carbon atoms in the alkyl moiety which is optionally mono- to trisubstituted by identical or different substituents from the group consisting of halogen, alkyl having 1 to 4 carbon atoms, halogenoalkyl having 1 or 2 carbon atoms and 1 to 5 halogen atoms, alkoxy having 1 to 4 carbon atoms and halogenoalkoxy having 1 or 2 carbon atoms and 1 to 5 halogen atoms, $X^9$ preferably represents fluorine, chlorine, bromine, methyl ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents from the group consisting of fluorine, chlorine, bromine and methyl or represents phenoxy which is optionally mono- or disubstituted by identical or different substituents from the group consisting of fluorine, chlorine, bromine and methyl and z preferably represents the numbers 0, 1, 2 or 3, where $X^9$ represents identical or different radicals if z represents 2 or 3.

Q preferably represents sulphur.

R¹ particularly preferably represents straight-chain or branched alkyl having 1 to 5 carbon atoms, cyclopentyl, cyclohexyl, straight-chain or branched alkoxy having 1 to 5 carbon atoms, alkoxyalkoxy having 1 or 2 carbon atoms in each alkoxy moiety, alkoxyalkyl having 1 or 2 carbon atoms in the alkoxy moiety and 1 or 2 carbon atoms in the alkyl moiety, or represents phenyl which may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or represents phenylalkyl having 1 or 2 carbon atoms in the alkyl moiety, where the phenyl moiety may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or represents phenoxy which may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or represents phenylakoxy having 1 or 2 carbon atoms in the alkoxy moiety, where the phenyl moiety may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or represents pyridyl, pyrrolyl, thienyl or furanyl, where each of these radicals may be mono- or disubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or R¹ represents a radical of the formula

in which

R⁴ particularly preferably represents hydrogen, methyl, ethyl, n-propyl, isopropyl or n-butyl and R⁵ particularly preferably represents alkyl having 1 to 4 carbon atoms or represents phenylalkyl having 1 or 2 carbon atoms in the alkyl moiety, where the phenyl moiety may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or R⁵ particularly preferably represents phenyl which may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or R⁴ and R⁵ together represent an alkylene chain having 4 or 5 carbon atoms or represent a radical of the formula —CH₂—CH₂—O—CH₂—CH₂— or

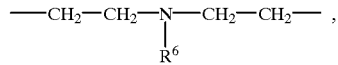

in which

R⁶ represents hydrogen, methyl or ethyl,

R² particularly preferably represents straight-chain or branched alkoxy having 1 to 5 carbon atoms, cyclopentyloxy, cyclohexyloxy, alkoxyalkoxy having 1 or 2 carbon atoms in each alkoxy moiety, or represents phenyloxy which may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or represents phenylalkoxy having 1 or 2 carbon atoms in the alkoxy moiety, where the phenyl moiety may be mono- to trisubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano, or represents pyridyloxy, pyrrolyloxy, thienyloxy or furanyloxy, where each of these radicals may be mono- or disubstituted by identical or different substituents from the group consisting of fluorine, chlorine, bromine, methyl, ethyl, methoxy, ethoxy, trifluoromethyl, difluoromethyl, trichloromethyl, trifluoromethoxy, difluoromethoxy, phenyl, nitro and cyano.

R³ particularly preferably represents a radical of the formula

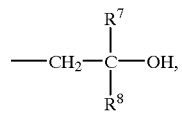

in which

R⁷ particularly preferably represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in alkoxy moiety, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, which each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and cyano, formyl, dimethoxymethyl, acetyl and propionyl, and $R^8$ particularly preferably represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in alkoxy moiety, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, which each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and cyano, formyl, dimethoxymethyl, acetyl and propionyl.

$R^3$ furthermore particularly preferably represents a radical of the formula

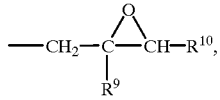

in which $R^9$ particularly preferably represents methyl, ethyl, n-propyl, isopropyl, n-butyl, sec-butyl, iso-butyl, tert-butyl, fluoro-tert-butyl, difluoro-tert-butyl, cycloalkyl having 3 to 6 carbon atoms which is optionally mono- to trisubstituted by identical or different substituents from the group consisting of fluorine, chlorine and bromine, represents naphthyl or represents phenyl which may be mono- to trisubstituted by identical or different substituents from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and trifluoromethylthio, and $R^{10}$ particularly preferably represents phenyl which may be mono- to trisubstituted by identical or different substituents from the group consisting of fluorine, chlorine, bromine, methyl, ethyl, isopropyl, tert-butyl, methoxy, ethoxy, trifluoromethyl, trichloromethyl, difluoromethyl, difluorochloromethyl, trifluoromethoxy, difluoromethoxy and trifluoromethylthio.

$R^3$ furthermore particularly preferably represents a radical of the formula

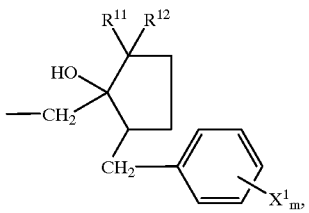

in which $R^{11}$ particularly preferably represents hydrogen, methyl, ethyl, n-propyl, isopropyl, n-butyl, iso-butyl, sec-butyl, tert-butyl or n-pentyl, $R^{12}$ particularly preferably represents hydrogen, methyl, ethyl, n-propyl, isopropyl, n-butyl, iso-butyl, sec-butyl, tert-butyl or n-pentyl, $X^1$ particularly preferably represents fluorine, chlorine, bromine, methyl, ethyl, n-propyl, isopropyl, n-butyl, iso-butyl, sec-butyl, tert-butyl, methoxy, ethoxy, phenyl, phenoxy, trichloromethyl, trifluoromethyl, trifluoromethoxy, difluoromethoxy or trifluoromethyl and m also particularly preferably represents the numbers 0, 1 or 2,
where
$X^1$ may represent identical or different radicals if m represents 2.

$R^3$ furthermore particularly preferably represents a radical of the formula

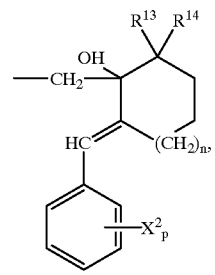

in which $R^{13}$ particularly preferably represents hydrogen, methyl, ethyl, n-propyl, isopropyl, n-butyl, iso-butyl, sec-butyl, tert-butyl or n-pentyl, $R^{14}$ particularly preferably represents hydrogen, methyl, ethyl, n-propyl, isopropyl, n-butyl, iso-butyl, sec-butyl, tert-butyl or n-pentyl, $X^2$ particularly preferably represents fluorine, chlorine, bromine, cyano, nitro, methyl, ethyl, n-propyl, isopropyl, n-butyl, iso-butyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n also particularly preferably represents the numbers 0 or 1 and p also particularly preferably represents the numbers 0, 1 or 2,
where
$X^2$ may represent identical or different radicals if p represents 2.

$R^3$ furthermore particularly preferably represents a radical of the formula

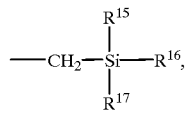

in which $R^{15}$ particularly preferably represents the radical of the formula

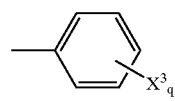

in which $X^3$ particularly preferably represents fluorine, chlorine, bromine, methyl, methoxy, methylthio, trichloromethyl, trifluoromethyl, trifluoromethoxy, difluoromethoxy or phenyl and q also particularly preferably represents the numbers 0, 1 or 2, where $X^3$ represents identical or different radicals if q represents 2, $R^{16}$ particularly preferably represents methyl, ethyl, n-propyl, n-butyl or represents the radical of the formula

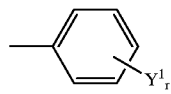

in which
- $Y^1$ particularly preferably represents fluorine, chlorine, bromine, methyl, ethyl, methoxy, trichloromethyl, trifluoromethyl, trifluoromethoxy, difluoromethoxy or phenyl, and
- r also particularly preferably represents the numbers 0, 1 or 2, where $Y^1$ represents identical or different radicals if r represents 2, and
- $R^{17}$ particularly preferably represents methyl, ethyl, n-propyl or n-butyl.

$R^3$ furthermore particularly preferably represents a radical of the formula

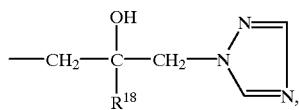

in which
- $R^{18}$ particularly preferably represents methyl, ethyl, n-propyl, isopropyl, n-butyl, sec-butyl, iso-butyl, tert-butyl, halogenoalkyl having 1 to 4 carbon atoms and 1 to 3 fluorine, chlorine and/or bromine atoms, cyclopropyl, cyclopentyl or cyclohexyl, which is optionally mono- to trisubstituted by identical or different substituents from the group consisting of fluorine, chlorine, bromine, methyl and ethyl, and also represents phenyl, benzyl or phenethyl, where each of the three last-mentioned radicals may be mono- to trisubstituted in the phenyl moiety by identical or different substituents from the group consisting of fluorine, chlorine, bromine, methyl, ethyl, methoxy, methylthio, trichloromethyl, trifluoromethyl, trifluoromethoxy, difluoromethoxy, trifluoromethylthio, phenyl and phenoxy.

$R^3$ furthermore particularly preferably represents a radical of the formula

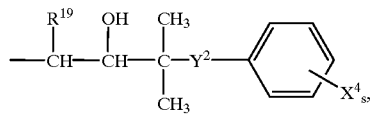

in which
- $R^{19}$ particularly preferably represents hydrogen, straight-chain or branched alkyl having 1 to 6 carbon atoms or represents cyclopropyl, cyclopentyl or cyclohexyl, which is optionally mono- to trisubstituted by identical or different substituents from the group consisting of fluorine, chlorine, bromine, methyl and ethyl,
- $X^4$ particularly preferably represents fluorine, chlorine, bromine, methyl, methoxy, methylthio, trichloromethyl, trifluoromethyl, trifluoromethoxy, difluoromethoxy, trifluoromethylthio, phenyl or phenoxy,
- s also particularly preferably represents the numbers 0, 1, 2 or 3, where $X^4$ represents identical or different radicals if s represents 2 or 3 and
- $Y^2$ also particularly preferably represents an oxygen atom, a $CH_2$ group or a direct bond.

$R^3$ furthermore particularly preferably represents a radical of the formula

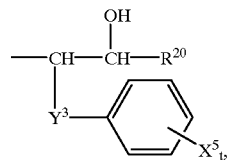

in which
- $R^{20}$ particularly preferably represents methyl, isopropyl, tert-butyl, fluoro-tert-butyl, difluoro-tert-butyl, represents cyclopropyl, cyclopentyl or cyclohexyl, which is optionally mono- to trisubstituted by identical or different substituents from the group consisting of fluorine, chlorine, and methyl, represents cycloalkylalkyl having 3 to 6 carbon atoms in the cycloalkyl moiety and 1 or 2 carbon atoms in alkyl moiety, phenyl which is optionally mono- or disubstituted by identical or different substituents from the group consisting of fluorine, chlorine and bromine, or represents benzyl which is optionally mono- or disubstituted by identical or different substituents from the group consisting of fluorine, chlorine and bromine,
- $X^5$ particularly preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl or phenoxy,
- t also particularly preferably represents the numbers 0, 1, 2 or 3, where $X^5$ represents identical or different radicals if t represents 2 or 3 and
- $Y^3$ also particularly preferably represents an oxygen atom or represents a $CH_2$ group.

$R^3$ furthermore particularly preferably represents a radical of the formula

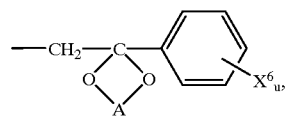

in which
- A particularly preferably represents alkanediyl having 2 or 3 carbon atoms which is optionally mono- to trisubstituted by identical or different substituents from the group consisting of fluorine, chlorine, bromine, methyl, ethyl, n-propyl, isopropyl, n-butyl, i-butyl, sec-butyl and tert-butyl,
- $X^6$ particularly preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally mono- to trisubstituted by identical or different substituents from the group consisting of fluorine, chlorine and methyl and/or represents phenoxy which is optionally mono- to trisubstituted by identical or different substituents from the group consisting of fluorine, chlorine and methyl and
- u also particularly preferably represents the numbers 0, 1, 2 or 3, where $X^6$ represents identical or different radicals if u represents 2 or 3.

$R^3$ furthermore particularly preferably represents a radical of the formula

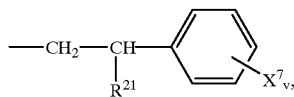

in which
- $R^{21}$ particularly preferably represents methyl, ethyl, n-propyl, isopropyl, n-butyl, iso-butyl, sec-butyl, tert-butyl, halogenoalkyl having 1 to 4 carbon atoms and 1 to 5 fluorine, chlorine and/or bromine atoms, fluoroalkoxyalkyl having 1 or 2 carbon atoms and 1 to 5 fluorine atoms in the fluoroalkoxy moiety and 1 or 2 carbon atoms in the alkyl moiety, represents cyclopropyl, cyclopentyl or cyclohexyl, which is optionally mono- to trisubstituted by identical or different substituents from the group consisting of fluorine, chlorine nd methyl, represents cycloalkylalkyl having 3 to 6 carbon atoms in the cycloalkyl moiety and 1 or 2 carbon atoms in the alkyl moiety, phenyl which is optionally mono- or disubstituted by identical or different substituents from the group consisting of fluorine, chlorine and bromine or represents benzyl which is optionally mono- or disubstituted by identical or different substituents from the group consisting of fluorine, chlorine and bromine,
- $X^7$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy and
- v also particularly preferably represents the numbers 0, 1, 2 or 3, where $X^7$ represents identical or different radicals if v represents 2 or 3.

$R^3$ furthermore particularly preferably represents a radical of the formula

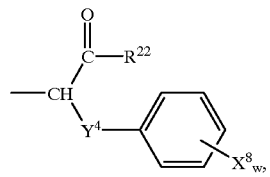

in which
- $R^{22}$ particularly preferably represents methyl, isopropyl, tert-butyl, fluoro-tert-butyl, difluoro-tert-butyl, represents cyclopropyl, cyclopentyl or cyclohexyl, which is optionally mono- to trisubstituted by identical or different substituents from the group consisting of fluorine, chlorine and methyl, represents cycloalkylalkyl having 3 to 6 carbon atoms in the cycloalkyl moiety and 1 or 2 carbon atoms in the alkyl moiety, phenyl which is optionally mono- or disubstituted by identical or different substituents from the group consisting of fluorine, chlorine and bromine, or represents benzyl which is optionally mono- or disubstituted by identical or different substituents from the group consisting of fluorine, chlorine and bromine,
- $X^8$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy,
- $Y^4$ also particularly preferably represents an oxygen atom or represents a $CH_2$ group, and
- w also particularly preferably represents the numbers 0, 1, 2 or 3, where $X^8$ represents identical or different radicals if w represents 2 or 3.

$R^3$ moreover also preferably represents a radical of the formula

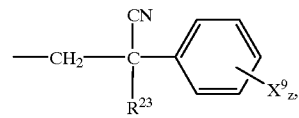

in which
- $R^{23}$ particularly preferably represents methyl, ethyl, n-propyl, isopropyl, n-butyl, sec-butyl, iso-butyl, tert-butyl, fluoro-tert-butyl, difluoro-tert-butyl, phenyl which is optionally mono- or disubstituted by identical or different substituents from the group consisting of fluorine, chlorine, methyl, ethyl, trifluoromethyl, trichloromethyl, methoxy, ethoxy, trifluoromethoxy and difluoromethoxy or represents phenylalkyl having 1 or 2 carbon atoms in the alkyl moiety which is optionally mono- or disubstituted in the phenyl moiety by identical or different substituents from the group consisting of fluorine, chlorine, bromine, methyl, ethyl, trifluomethyl, trichloromethyl, methoxy, ethoxy, trifluoromethoxy and difluoromethoxy,
- $X^9$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy, and
- z also particularly preferably represents the numbers 0, 1, 2 or 3, where $X^9$ represents identical or different radicals if z represents 2 or 3.
- Q also particularly preferably represents sulphur.

Preferred compounds according to the invention are also addition products of salts of metals of main groups II to IV and subgroups I and II and IV to VIII of the Periodic Table of the Elements and those triazolinethione-phosphoric acid derivatives of the formula (I) in which $R^1$, $R^2$, $R^3$ and Q each have those meanings which have been mentioned as being preferred for those substituents.

Particular preference is given here to salts of copper, zinc, manganese, magnesium, tin, iron and nickel. Suitable anions of these salts are those which are derived from acids which lead to physiologically acceptable addition products. Particularly preferred acids to this type are, in this context, the hydrohalic acids, such as, for example, hydrochloric acid and hydrobromic acid, furthermore phosphoric acid, nitric acid and sulphuric acid.

The triazolinethiones required as starting materials for preparing the substances according to the invention can be present in the "thiono" form of the formula (II)

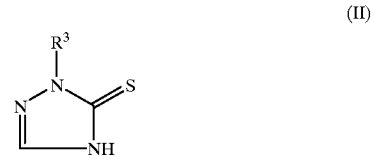

or in the tautomeric "mercapto" form of the formula (IIa)

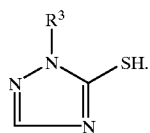

Thus, it is possible that the substances according to the invention are derived both from the "thiono" form of the formula (II) and from the "mercapto" form of the formula (IIa). This means that the substances according to the invention are present either as substances of the formula (I)

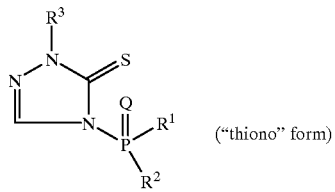 ("thiono" form)

or of the formula (Ia)

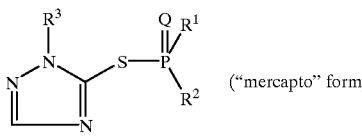 ("mercapto" form)

or as mixtures of the substances of the formulae (I) and (Ia). For the sake of simplicity, only the structure of the "thiono" form is given in each case.

Examples of substances according to the invention which may be mentioned are the triazolinethione-phosphoric acid derivatives listed in the tables below.

TABLE 1

(Ib)

| $R^7$ | $R^8$ | $R^1$ | $R^{2'}$ |
|---|---|---|---|
| Cl—C₆H₄—CH₂—CH₂— | —C(CH₃)₃ | —CH₃ | —C₂H₅ |
| Cl—C₆H₄—CH₂—CH₂— | —C(CH₃)₃ | —C₂H₅ | —C₂H₅ |
| Cl—C₆H₄—CH₂—CH₂— | —C(CH₃)₃ | —C₆H₄—Cl | —C₂H₅ |
| Cl—C₆H₄—CH₂—CH₂— | —C(CH₃)₃ | —O—CH₃ | —C₂H₅ |
| Cl—C₆H₄—CH₂—CH₂— | —C(CH₃)₃ | —CH₂—C₆H₅ | —C₂H₅ |
| Cl—C₆H₄—CH₂—CH₂— | —C(CH₃)₃ | —NH—CH₃ | —C₂H₅ |

TABLE 1-continued (Ib) Structure: R7-C(OH)(R8)-CH2-N(triazole-thione with N-P(=S)(R1)(OR2'))

| R⁷ | R⁸ | R¹ | R²' |
|---|---|---|---|
| 4-Cl-C₆H₄-CH₂-CH₂- | —C(CH₃)₃ | —NH-C₆H₄-4-Cl | —C₂H₅ |
| 4-Cl-C₆H₄-CH₂- | —C(CH₃)₃ | —CH₃ | —C₂H₅ |
| 4-Cl-C₆H₄-CH₂- | —C(CH₃)₃ | —C₂H₅ | —C₂H₅ |
| 4-Cl-C₆H₄-CH₂- | —C(CH₃)₃ | -C₆H₄-4-Cl | —C₂H₅ |
| 4-Cl-C₆H₄-CH₂- | —C(CH₃)₃ | —OCH₃ | —C₂H₅ |
| 4-Cl-C₆H₄-CH₂- | —C(CH₃)₃ | —CH₂-C₆H₅ | —C₂H₅ |
| 4-Cl-C₆H₄-CH₂- | —C(CH₃)₃ | —NH—CH₃ | —C₂H₅ |
| 4-Cl-C₆H₄-CH(CH₃)- | —C(CH₃)₃ | —CH₃ | —C₂H₅ |
| 4-Cl-C₆H₄-CH(CH₃)- | —C(CH₃)₃ | —C₂H₅ | —C₂H₅ |
| 4-Cl-C₆H₄-CH(CH₃)- | —C(CH₃)₃ | —CH₂-C₆H₅ | —C₂H₅ |
| 4-Cl-C₆H₄-CH(CH₃)- | —C(CH₃)₃ | —NH—CH₃ | —C₂H₅ |

TABLE 1-continued (Ib) Structure: triazole-thione with N-CH$_2$-C(OH)(R$^7$)(R$^8$) substituent and N-P(=S)(R$^1$)(OR$^{2'}$) substituent

| R$^7$ | R$^8$ | R$^1$ | R$^{2'}$ |
|---|---|---|---|
| 4-F-C$_6$H$_4$- | 2-F-C$_6$H$_4$- | —CH$_3$ | —C$_2$H$_5$ |
| 4-F-C$_6$H$_4$- | 2-F-C$_6$H$_4$- | —C$_2$H$_5$ | —C$_2$H$_5$ |
| 4-F-C$_6$H$_4$- | 2-F-C$_6$H$_4$- | —CH$_2$-C$_6$H$_5$ | —C$_2$H$_5$ |
| 4-F-C$_6$H$_4$- | 2-F-C$_6$H$_4$- | —NH—CH$_3$ | —C$_2$H$_5$ |
| 2,4-Cl$_2$-C$_6$H$_3$- | —C$_4$H$_9$-n | —CH$_3$ | —C$_2$H$_5$ |
| 2,4-Cl$_2$-C$_6$H$_3$- | —C$_4$H$_9$-n | —C$_2$H$_5$ | —C$_2$H$_5$ |
| 2,4-Cl$_2$-C$_6$H$_3$- | —C$_4$H$_9$-n | —CH$_2$-C$_6$H$_5$ | —C$_2$H$_5$ |
| 2,4-Cl$_2$-C$_6$H$_3$- | —C$_4$H$_9$-n | —NH—CH$_3$ | —C$_2$H$_5$ |

TABLE 1-continued (Ib)

$$\underset{\substack{\text{R}^7-\text{C}-\text{R}^8\\|\\ \text{CH}_2}}{\overset{\text{OH}}{|}} \text{—(triazole-thione-phosphorothioate ring system)}$$

| R⁷ | R⁸ | R¹ | R²' |
|---|---|---|---|
| 4-Cl-C₆H₄— | —CH(CH₃)(cyclopropyl) | —CH₃ | —C₂H₅ |
| 4-Cl-C₆H₄— | —CH(CH₃)(cyclopropyl) | —OCH₃ | —C₂H₅ |
| 4-Cl-C₆H₄— | —CH(CH₃)(cyclopropyl) | —CH₂—C₆H₅ | —C₂H₅ |
| 4-Cl-C₆H₄— | —CH(CH₃)(cyclopropyl) | —NH—CH₃ | —C₂H₅ |
| 4-Cl-C₆H₄—O—CH₂— | —C(CH₃)₃ | —CH₃ | —C₂H₅ |
| 4-Cl-C₆H₄—O—CH₂— | —C(CH₃)₃ | —OC₂H₅ | —C₂H₅ |
| 4-Cl-C₆H₄—O—CH₂— | —C(CH₃)₃ | —CH₂—C₆H₅ | —C₂H₅ |
| 4-Cl-C₆H₄—O—CH₂— | —C(CH₃)₃ | —OCH₃ | —C₂H₅ |
| Cl₂CH—CCl₂—CH₂— | —C(CH₃)₃ | —OCH₃ | —C₂H₅ |
| Cl₂CH—CCl₂—CH₂— | —C(CH₃)₃ | —OC₂H₅ | —C₂H₅ |
| Cl₂CH—CCl₂—CH₂— | (cyclopropyl-Cl) | —OCH₃ | —C₂H₅ |
| Cl₂CH—CCl₂—CH₂— | (cyclopropyl-Cl) | —OC₂H₅ | —C₂H₅ |
| Cl₂CH—CCl₂—CH₂— | (cyclopropyl-Cl) | —OC₃H₇ | —C₂H₅ |
| Cl₂CH—CCl₂—CH₂— | (cyclopropyl-Cl) | —OCH₃ | —C₂H₅ |

TABLE 1-continued (Ib)

| R⁷ | R⁸ | R¹ | R²' |
|---|---|---|---|
| 4-Cl-C₆H₄-CH=CH- | —C(CH₃)₃ | —OCH₃ | —C₂H₅ |
| 4-Cl-C₆H₄-CH=CH- | —C(CH₃)₃ | —OC₂H₅ | —C₂H₅ |
| 4-Cl-C₆H₄-CH=CH- | cyclopropyl-Cl | —OCH₃ | —C₂H₅ |
| 4-Cl-C₆H₄-CH₂-CH₂- | cyclopropyl-Cl | —OC₂H₅ | —C₂H₅ |
| 4-Cl-C₆H₄-CH₂- | cyclopropyl-Cl | —OC₂H₅ | —C₂H₅ |
| 4-Cl-C₆H₄-CH(CH₃)- | cyclopropyl-Cl | —OC₂H₅ | —C₂H₅ |
| 4-Cl-C₆H₄-O-CH₂- | cyclopropyl-Cl | —OCH(CH₃)₂ | —C₂H₅ |
| Cl₂CH—CCl₂ | cyclopropyl-Cl | —OCH(CH₃)₂ | —C₂H₅ |
| 2-furyl-CH₂-CH₂- | —C(CH₃)₃ | —OCH(CH₃)₂ | —C₂H₅ |
| 2-pyridyl-CH₂-CH₂- | —C(CH₃) | —OC₂H₅ | —C₂H₅ |
| 4-Cl-C₆H₄-CH₂-CH₂- | —C(CH₃)₃ | —C₆H₅ | —C₂H₅ |

TABLE 2

(Ic)

| R⁹ | R¹⁰ | R¹ | R²' |
|---|---|---|---|
| phenyl | 2-chlorophenyl | —OC₂H₅ | —C₂H₅ |
| 4-chlorophenyl | 2-chlorophenyl | —OC₂H₅ | —C₂H₅ |
| 4-biphenylyl | 2-chlorophenyl | —OC₂H₅ | —C₂H₅ |
| 2,4-dichlorophenyl | 2-chlorophenyl | —OC₂H₅ | —C₂H₅ |
| 2-chlorophenyl | 2-chlorophenyl | —OC₂H₅ | —C₂H₅ |
| 2-fluorophenyl | 2-chlorophenyl | —OC₂H₅ | —C₂H₅ |
| 4-methylphenyl | 2-chlorophenyl | —OC₂H₅ | —C₂H₅ |
| —C(CH₃)₂CH₂F | 2-chlorophenyl | —OC₂H₅ | —C₂H₅ |
| 3-bromo-4-fluorophenyl | 2-chlorophenyl | —OC₂H₅ | —C₂H₅ |
| 4-bromophenyl | 2-chlorophenyl | —OC₂H₅ | —C₂H₅ |
| 2,4-dichlorophenyl | 2-chlorophenyl | —OC₂H₅ | —C₂H₅ |
| 4-tert-butylphenyl | 2-chlorophenyl | —OC₂H₅ | —C₂H₅ |
| 3-chlorophenyl | 2-chlorophenyl | —OC₂H₅ | —C₂H₅ |
| 3,5-dichlorophenyl | 2-chlorophenyl | —OC₂H₅ | —C₂H₅ |
| 4-phenoxyphenyl | 2-chlorophenyl | —OC₂H₅ | —C₂H₅ |
| 4-trifluoromethoxyphenyl | 2-chlorophenyl | —OC₂H₅ | —C₂H₅ |

TABLE 2-continued
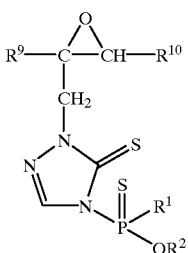
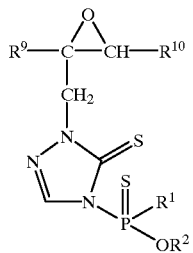

TABLE 2-continued (Ic)

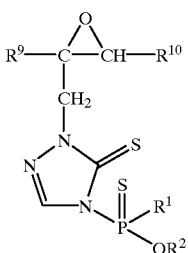

| R⁹ | R¹⁰ | R¹ | R²' |
|---|---|---|---|
| 4-phenoxyphenyl | 2-F-phenyl | —OC₂H₅ | —C₂H₅ |
| 2-Cl-phenyl | 4-F-phenyl | —OC₂H₅ | —C₂H₅ |
| 4-Cl-phenyl | 2-Br-phenyl | —NH—CH₃ | —C₂H₅ |
| phenyl | 2-Br-phenyl | —NH—CH₃ | —C₂H₅ |
| 4-biphenyl | 2-Br-phenyl | —NH—CH₃ | —C₂H₅ |
| 2,4-diCl-phenyl | 2-Br-phenyl | —NH—CH₃ | —C₂H₅ |
| 2-Cl-phenyl | 2-Br-phenyl | —NH—CH₃ | —C₂H₅ |
| 2-F-phenyl | 2-Br-phenyl | —NH—CH₃ | —C₂H₅ |
| 4-CH₃-phenyl | 2-Br-phenyl | —NH—CH₃ | —C₂H₅ |
| 4-F-phenyl | 2-Br-phenyl | —OC₂H₅ | —C₂H₅ |
| 3-Br-4-F-phenyl | 2-Br-phenyl | —OC₂H₅ | —C₂H₅ |
| 4-Br-phenyl | 2-Br-phenyl | —OC₂H₅ | —C₂H₅ |
| 2,4-diCl-phenyl | 2-Br-phenyl | —OC₂H₅ | —C₂H₅ |
| 4-C(CH₃)₃-phenyl | 2-Br-phenyl | —OC₂H₅ | —C₂H₅ |
| 3-Cl-phenyl | 2-Br-phenyl | —OC₂H₅ | —C₂H₅ |
| 3,5-diCl-phenyl | 2-Br-phenyl | —OC₂H₅ | —C₂H₅ |

TABLE 2-continued (Ic)

Structure: R⁹—C(—O—CH—R¹⁰ epoxide)—CH₂—N(triazole-thione)—N—P(=S)(R¹)(OR²)

| R⁹ | R¹⁰ | R¹ | R²' |
|---|---|---|---|
| 4-phenoxyphenyl | 2-bromophenyl | —OC₂H₅ | —C₂H₅ |
| —CH₃ | 2-chlorophenyl | —OC₂H₅ | —C₂H₅ |
| —CH₃ | 2-fluorophenyl | —OC₂H₅ | —C₂H₅ |
| —CH₃ | 2-bromophenyl | —OC₂H₅ | —C₂H₅ |
| —C(CH₃)₃ | 2-chlorophenyl | —OC₂H₅ | —C₂H₅ |
| 1-chlorocyclopropyl | 2-chlorophenyl | —OC₂H₅ | —C₂H₅ |
| phenyl | 2-chlorophenyl | —C₂H₅ | —C₂H₅ |
| 4-chlorophenyl | 2-chlorophenyl | —C₂H₅ | —C₂H₅ |
| 4-biphenyl | 2-chlorophenyl | —C₂H₅ | —C₂H₅ |
| 2,4-dichlorophenyl | 2-chlorophenyl | —C₂H₅ | —C₂H₅ |
| 2-chlorophenyl | 2-chlorophenyl | —C₂H₅ | —C₂H₅ |
| 2-fluorophenyl | 2-chlorophenyl | —C₂H₅ | —C₂H₅ |
| 4-methylphenyl | 2-chlorophenyl | —C₂H₅ | —C₂H₅ |
| 3-bromo-4-fluorophenyl | 2-chlorophenyl | —C₂H₅ | —C₂H₅ |
| 4-bromophenyl | 2-chlorophenyl | —C₂H₅ | —C₂H₅ |
| 2,4-dichlorophenyl | 2-chlorophenyl | —C₂H₅ | —C₂H₅ |

TABLE 2-continued
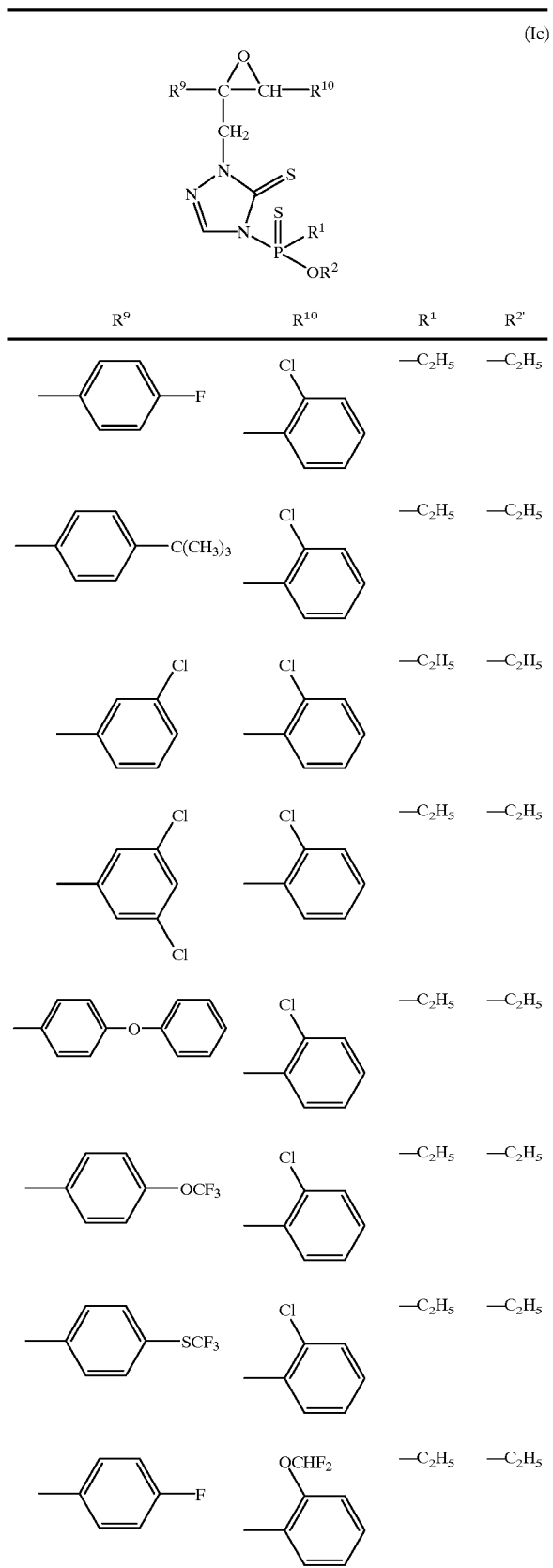
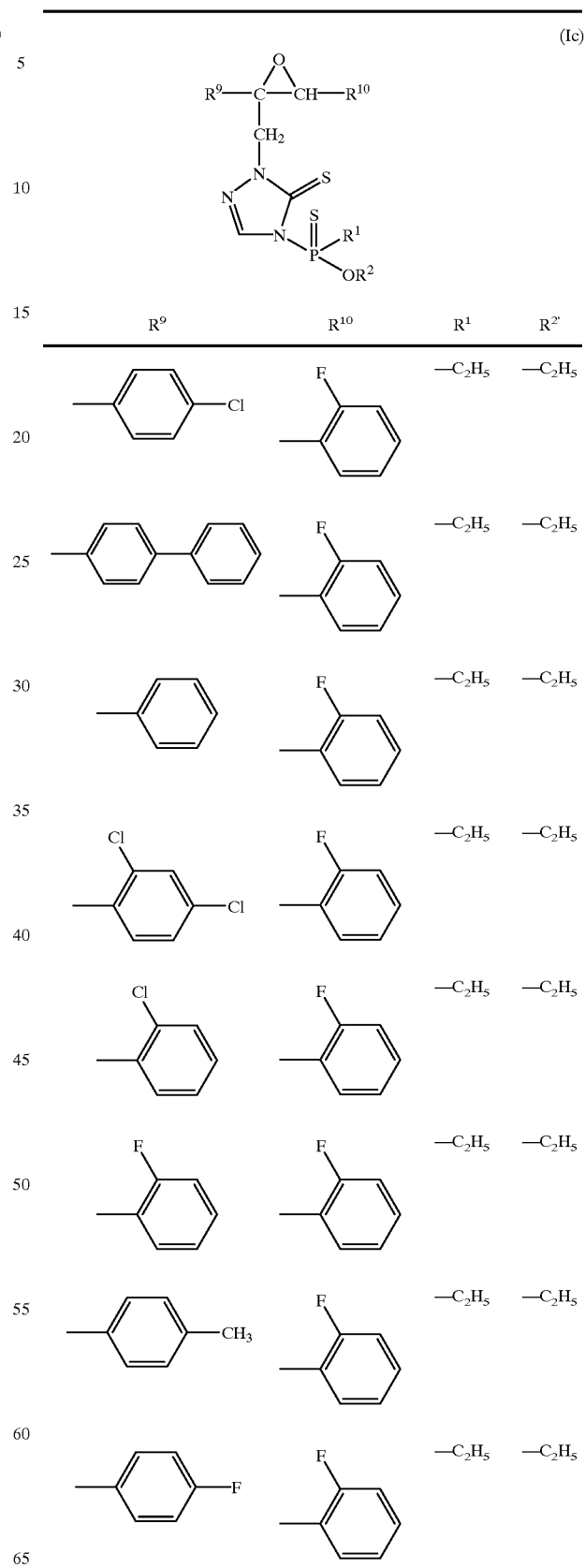

TABLE 2-continued (Ic)

| $R^9$ | $R^{10}$ | $R^1$ | $R^{2'}$ |
|---|---|---|---|
| 3-Br-4-F-phenyl | 2-F-phenyl | —C$_2$H$_5$ | —C$_2$H$_5$ |
| 4-Br-phenyl | 2-F-phenyl | —C$_2$H$_5$ | —C$_2$H$_5$ |
| 2,4-di-Cl-phenyl | 2-F-phenyl | —C$_2$H$_5$ | —C$_2$H$_5$ |
| 4-C(CH$_3$)$_3$-phenyl | 2-F-phenyl | —C$_2$H$_5$ | —C$_2$H$_5$ |
| 3-Cl-phenyl | 2-F-phenyl | —C$_2$H$_5$ | —C$_2$H$_5$ |
| 3,5-di-Cl-phenyl | 2-F-phenyl | —C$_2$H$_5$ | —C$_2$H$_5$ |
| 4-phenoxy-phenyl | 2-F-phenyl | —C$_2$H$_5$ | —C$_2$H$_5$ |
| 4-Cl-phenyl | 2-Br-phenyl | —C$_2$H$_5$ | —C$_2$H$_5$ |
| phenyl | 2-Br-phenyl | —C$_2$H$_5$ | —C$_2$H$_5$ |
| 4-biphenyl | 2-Br-phenyl | —C$_2$H$_5$ | —C$_2$H$_5$ |
| 2,4-di-Cl-phenyl | 2-Br-phenyl | —C$_2$H$_5$ | —C$_2$H$_5$ |
| 2-Cl-phenyl | 2-Br-phenyl | —C$_2$H$_5$ | —C$_2$H$_5$ |
| 2-F-phenyl | 2-Br-phenyl | —C$_2$H$_5$ | —C$_2$H$_5$ |
| 4-CH$_3$-phenyl | 2-Br-phenyl | —C$_2$H$_5$ | —C$_2$H$_5$ |
| 4-F-phenyl | 2-Br-phenyl | —C$_2$H$_5$ | —C$_2$H$_5$ |
| 3-Br-4-F-phenyl | 2-Br-phenyl | —C$_2$H$_5$ | —C$_2$H$_5$ |

TABLE 2-continued (Ic)

[Structure: oxirane-CH₂-linked 1,2,4-triazole-3-thione with N-P(=S)(R¹)(OR²') substituent; R⁹ and R¹⁰ on the oxirane carbons]

| R⁹ | R¹⁰ | R¹ | R²' |
|---|---|---|---|
| 4-Br-phenyl | 2-Br-phenyl | —C₂H₅ | —C₂H₅ |
| 2,4-Cl₂-phenyl | 2-Br-phenyl | —C₂H₅ | —C₂H₅ |
| 4-C(CH₃)₃-phenyl | 2-Br-phenyl | —C₂H₅ | —C₂H₅ |
| 3-Cl-phenyl | 2-Br-phenyl | —C₂H₅ | —C₂H₅ |
| —C(CH₃)₂CH₂F | 2-Cl-phenyl | —C₂H₅ | —C₂H₅ |
| 3,5-Cl₂-phenyl | 2-Br-phenyl | —C₂H₅ | —C₂H₅ |
| 4-phenoxyphenyl | 2-Br-phenyl | —C₂H₅ | —C₂H₅ |
| —CH₃ | 2-Cl-phenyl | —C₂H₅ | —C₂H₅ |

TABLE 2-continued (Ic)

[Structure: same as above]

| R⁹ | R¹⁰ | R¹ | R²' |
|---|---|---|---|
| —CH₃ | 2-F-phenyl | —C₂H₅ | —C₂H₅ |
| —CH₃ | 2-Br-phenyl | —C₂H₅ | —C₂H₅ |
| —C(CH₃)₃ | 2-Cl-phenyl | —C₂H₅ | —C₂H₅ |
| 1-Cl-cyclopropyl | 2-Cl-phenyl | —C₂H₅ | —C₂H₅ |

TABLE 3

(Id)

[Structure: cyclopentane bearing R¹¹, R¹² at one carbon, OH and CH₂-triazolyl at adjacent carbon, and CH₂-aryl(X¹ₘ) substituent; triazole N-P(=S)(R¹)(OR²')]

| R¹¹ | R¹² | R¹ | R²' | X¹ₘ |
|---|---|---|---|---|
| —CH₃ | —CH₃ | —OC₂H₅ | —C₂H₅ | 4-Br |
| —CH₃ | —CH₃ | —OC₂H₅ | —C₂H₅ | 4-F |
| —CH₃ | —CH₃ | —OC₂H₅ | —C₂H₅ | 2,4-Cl₂ |
| —CH₃ | H | —OC₂H₅ | —C₂H₅ | 4-Cl |
| —CH₃ | —CH₃ | —OC₂H₅ | —C₂H₅ | — |
| —CH₃ | —CH₃ | —OC₂H₅ | —C₂H₅ | 4-CH₃ |
| —CH₃ | —CH₃ | —OC₂H₅ | —C₂H₅ | 2-F, 4-Cl |
| —C₂H₅ | H | —OC₂H₅ | —C₂H₅ | 4-Cl |
| —C₂H₅ | —C₂H₅ | —OC₂H₅ | —C₂H₅ | 4-Cl |
| —C₃H₇-n | H | —OC₂H₅ | —C₂H₅ | 2,4-Cl₂ |
| —C₂H₅ | H | —OC₂H₅ | —C₂H₅ | 2,4-Cl₂ |
| —C₂H₅ | H | —OC₂H₅ | —C₂H₅ | 4-F |
| —C₂H₅ | H | —OC₂H₅ | —C₂H₅ | 4-Br |

TABLE 3-continued

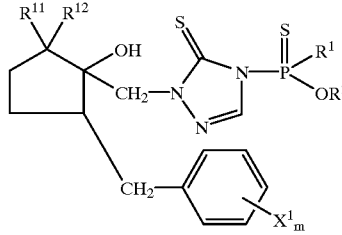

(Id)

| R¹¹ | R¹² | R¹ | R²' | X¹ₘ |
|---|---|---|---|---|
| —C₂H₅ | H | —OC₂H₅ | —C₂H₅ | 4-phenyl |
| —C₂H₅ | H | —OC₂H₅ | —C₂H₅ | 4-C₄H₉-t |
| —C₃H₇-i | H | —OC₂H₅ | —C₂H₅ | 4-Cl |
| —C₅H₁₁-n | H | —OC₂H₅ | —C₂H₅ | 4-Cl |
| —CH₃ | —CH₃ | —OC₂H₅ | —C₂H₅ | 4-phenyl |
| —CH₃ | —CH₃ | —OC₂H₅ | —C₂H₅ | 4-C₄H₉-t |
| —C₄H₉-n | H | —OC₂H₅ | —C₂H₅ | 4-Cl |
| —C₄H₉-i | H | —OC₂H₅ | —C₂H₅ | 4-Cl |
| —CH₃ | —C₂H₅ | —OC₂H₅ | —C₂H₅ | 4-Cl |
| —CH₃ | —CH₃ | —C₂H₅ | —C₂H₅ | 4-Cl |
| —CH₃ | —CH₃ | —C₂H₅ | —C₂H₅ | 4-Br |
| —CH₃ | —CH₃ | —C₂H₅ | —C₂H₅ | 4-F |
| —CH₃ | —CH₃ | —C₂H₅ | —C₂H₅ | 2,4-Cl₂ |
| —CH₃ | H | —C₂H₅ | —C₂H₅ | 4-Cl |
| —CH₃ | —C₂H₅ | —C₂H₅ | —C₂H₅ | — |
| —CH₃ | —CH₃ | —C₂H₅ | —C₂H₅ | 4-CH₃ |
| —CH₃ | —CH₃ | —C₂H₅ | —C₂H₅ | 2-F, 4-Cl |
| —C₂H₅ | H | —C₂H₅ | —C₂H₅ | 4-Cl |
| —C₂H₅ | —C₂H₅ | —C₂H₅ | —C₂H₅ | 4-Cl |
| —C₃H₇-n | H | —C₂H₅ | —C₂H₅ | 4-Cl |
| —C₂H₅ | H | —C₂H₅ | —C₂H₅ | 2,4-Cl₂ |
| —C₂H₅ | H | —C₂H₅ | —C₂H₅ | 4-F |
| —C₂H₅ | H | —C₂H₅ | —C₂H₅ | 4-F |
| —C₂H₅ | H | —C₂H₅ | —C₂H₅ | 4-Br |
| —C₂H₅ | H | —C₂H₅ | —C₂H₅ | 4-phenyl |
| —C₂H₅ | H | —C₂H₅ | —C₂H₅ | 4-C₄H₉-t |
| —C₃H₇-i | H | —C₂H₅ | —C₂H₅ | 4-Cl |
| —C₅H₁₁-n | H | —C₂H₅ | —C₂H₅ | 4-Cl |
| —CH₃ | —CH₃ | —C₂H₅ | —C₂H₅ | 4-phenyl |
| —CH₃ | —CH₃ | —C₂H₅ | —C₂H₅ | 4-C₄H₉-t |
| —C₄H₉-n | H | —C₂H₅ | —C₂H₅ | 4-Cl |
| —C₄H₉-i | H | —C₂H₅ | —C₂H₅ | 4-Cl |
| —CH₃ | —C₂H₅ | —C₂H₅ | —C₂H₅ | 4-Cl |
| —CH₃ | —CH₃ | —OC₂H₅ | —C₂H₅ | 2-Cl |
| —CH₃ | —CH₃ | —OC₂H₅ | —C₂H₅ | 2,3-Cl₂ |
| —CH₃ | —CH₃ | —OC₂H₅ | —C₂H₅ | 4-CF₃ |
| —CH₃ | —CH₃ | —OC₂H₅ | —C₂H₅ | 4-OCF₃ |
| —CH₃ | —CH₃ | —OC₂H₅ | —C₂H₅ | 4-Cl |

TABLE 4

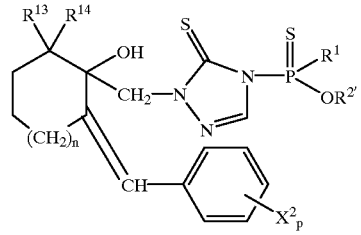

(Ie)

| R¹³ | R¹⁴ | R¹ | X²ₚ | n | R²' |
|---|---|---|---|---|---|
| —CH₃ | —CH₃ | —OC₂H₅ | 4-Br | 0 | —C₂H₅ |
| —CH₃ | —CH₃ | —OC₂H₅ | 4-F | 0 | —C₂H₅ |
| —CH₃ | —CH₃ | —OC₂H₅ | 2,4-Cl₂ | 0 | —C₂H₅ |
| —CH₃ | H | —OC₂H₅ | 4-Cl | 0 | —C₂H₅ |
| —CH₃ | —CH₃ | —OC₂H₅ | — | 0 | —C₂H₅ |
| —CH₃ | —CH₃ | —OC₂H₅ | 4-CH₃ | 0 | —C₂H₅ |
| —CH₃ | —CH₃ | —OC₂H₅ | 2-F, 4-Cl | 0 | —C₂H₅ |
| —C₂H₅ | H | —OC₂H₅ | 4-Cl | 0 | —C₂H₅ |
| —C₂H₅ | —C₂H₅ | —OC₂H₅ | 4-Cl | 0 | —C₂H₅ |
| —C₃H₇-n | H | —OC₂H₅ | 4-Cl | 0 | —C₂H₅ |
| —C₂H₅ | H | —OC₂H₅ | 2,4-Cl₂ | 0 | —C₂H₅ |
| —C₂H₅ | H | —OC₂H₅ | 4-F | 0 | —C₂H₅ |
| —C₂H₅ | H | —OC₂H₅ | 4-Br | 0 | —C₂H₅ |
| —C₂H₅ | H | —OC₂H₅ | 4-NO₂ | 0 | —C₂H₅ |
| —C₂H₅ | H | —OC₂H₅ | 4-C₄H₉-t | 0 | —C₂H₅ |
| —C₃H₇-i | H | —OC₂H₅ | 4-Cl | 0 | —C₂H₅ |
| —C₅H₁₁-n | H | —OC₂H₅ | 4-Cl | 0 | —C₂H₅ |
| —CH₃ | —CH₃ | —OC₂H₅ | 4-CN | 0 | —C₂H₅ |
| —CH₃ | —CH₃ | —OC₂H₅ | 4-C₄H₉-t | 0 | —C₂H₅ |
| —C₄H₉-n | H | —OC₂H₅ | 4-Cl | 0 | —C₂H₅ |
| —C₄H₉-i | H | —OC₂H₅ | 4-Cl | 0 | —C₂H₅ |
| —CH₃ | —C₂H₅ | —OC₂H₅ | 4-Cl | 0 | —C₂H₅ |
| —CH₃ | —CH₃ | —C₂H₅ | 4-Cl | 0 | —C₂H₅ |
| —CH₃ | —CH₃ | —C₂H₅ | 4-Br | 0 | —C₂H₅ |
| —CH₃ | —CH₃ | —C₂H₅ | 4-F | 0 | —C₂H₅ |
| —CH₃ | —CH₃ | —C₂H₅ | 2,4-Cl₂ | 0 | —C₂H₅ |
| —CH₃ | H | —C₂H₅ | 4-Cl | 0 | —C₂H₅ |
| —CH₃ | —CH₃ | —C₂H₅ | — | 0 | —C₂H₅ |
| —CH₃ | —CH₃ | —C₂H₅ | 4-CH₃ | 0 | —C₂H₅ |
| —CH₃ | —CH₃ | —C₂H₅ | 2-F, 4-Cl | 0 | —C₂H₅ |
| —C₂H₅ | H | —C₂H₅ | 4-Cl | 0 | —C₂H₅ |
| —C₂H₅ | —C₂H₅ | —C₂H₅ | 4-Cl | 0 | —C₂H₅ |
| —C₃H₇-n | H | —C₂H₅ | 4-Cl | 0 | —C₂H₅ |
| —C₂H₅ | H | —C₂H₅ | 2,4-Cl₂ | 0 | —C₂H₅ |
| —C₂H₅ | H | —C₂H₅ | 4-F | 0 | —C₂H₅ |
| —C₂H₅ | H | —C₂H₅ | 4-Br | 0 | —C₂H₅ |
| —C₂H₅ | H | —C₂H₅ | 4-NO₂ | 0 | —C₂H₅ |
| —C₂H₅ | H | —C₂H₅ | 4-C₄H₉-t | 0 | —C₂H₅ |
| —C₃H₇-i | H | —C₂H₅ | 4-Cl | 0 | —C₂H₅ |
| —C₅H₁₁-n | H | —C₂H₅ | 4-Cl | 0 | —C₂H₅ |
| —CH₃ | —CH₃ | —C₂H₅ | 4-CN | 0 | —C₂H₅ |
| —CH₃ | —CH₃ | —C₂H₅ | 4-C₄H₉-t | 0 | —C₂H₅ |
| —C₄H₉-n | H | —C₂H₅ | 4-Cl | 0 | —C₂H₅ |
| —C₄H₉-i | H | —C₂H₅ | 4-Cl | 0 | —C₂H₅ |
| —CH₃ | —C₂H₅ | —C₂H₅ | 4-Cl | 0 | —C₂H₅ |
| —CH₃ | —CH₃ | —OC₂H₅ | 4-OCH₃ | 0 | —C₂H₅ |
| —CH₃ | —CH₃ | —OC₂H₅ | 2-OCH₃ | 0 | —C₂H₅ |
| —CH₃ | —CH₃ | —OC₂H₅ | 2-CF₃ | 0 | —C₂H₅ |
| —CH₃ | —CH₃ | —OC₂H₅ | 4-CF₃ | 0 | —C₂H₅ |
| —CH₃ | —CH₃ | —OC₂H₅ | 2-OCF₃ | 0 | —C₂H₅ |
| —CH₃ | —CH₃ | —OC₂H₅ | 2-OCHF₂ | 0 | —C₂H₅ |
| —CH₃ | —CH₃ | —OC₂H₅ | 4-OCF₃ | 0 | —C₂H₅ |
| —CH₃ | —CH₃ | —C₂H₅ | 4-OCH₃ | 0 | —C₂H₅ |
| —CH₃ | —CH₃ | —C₂H₅ | 2-OCH₃ | 0 | —C₂H₅ |
| —CH₃ | —CH₃ | —C₂H₅ | 2-CF₃ | 0 | —C₂H₅ |
| —CH₃ | —CH₃ | —C₂H₅ | 4-CF₃ | 0 | —C₂H₅ |
| —CH₃ | —CH₃ | —C₂H₅ | 2-OCF₃ | 0 | —C₂H₅ |
| —CH₃ | —CH₃ | —C₂H₅ | 2-OCHF₂ | 0 | —C₂H₅ |
| —CH₃ | —CH₃ | —C₂H₅ | 4-OCF₃ | 0 | —C₂H₅ |
| —CH₃ | —CH₃ | —OC₂H₅ | 4-Br | 1 | —C₂H₅ |
| —CH₃ | —CH₃ | —OC₂H₅ | 4-F | 1 | —C₂H₅ |
| —CH₃ | —CH₃ | —OC₂H₅ | 2,4-Cl₂ | 1 | —C₂H₅ |
| —CH₃ | H | —OC₂H₅ | 4-Cl | 1 | —C₂H₅ |

TABLE 4-continued

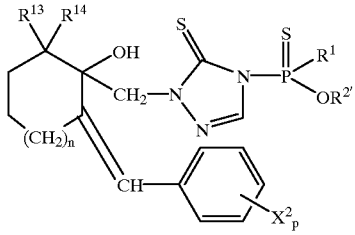

(Ie)

| R13 | R14 | R1 | X2p | n | R2' |
|---|---|---|---|---|---|
| —CH3 | —CH3 | —OC2H5 | — | 1 | —C2H5 |
| —CH3 | —CH3 | —OC2H5 | 4-CH3 | 1 | —C2H5 |
| —CH3 | —CH3 | —OC2H5 | 2-F, 4-Cl | 1 | —C2H5 |
| —C2H5 | H | —OC2H5 | 4-Cl | 1 | —C2H5 |
| —C2H5 | —C2H5 | —OC2H5 | 4-Cl | 1 | —C2H5 |
| —C3H7-n | H | —OC2H5 | 4-Cl | 1 | —C2H5 |
| —C2H5 | H | —OC2H5 | 2,4-Cl2 | 1 | —C2H5 |
| —C2H5 | H | —OC2H5 | 4-F | 1 | —C2H5 |
| —C2H5 | H | —OC2H5 | 4-Br | 1 | —C2H5 |
| —C2H5 | H | —OC2H5 | 4-NO2 | 1 | —C2H5 |
| —C2H5 | H | —OC2H5 | 4-C4H9-t | 1 | —C2H5 |
| —C3H7-i | H | —OC2H5 | 4-Cl | 1 | —C2H5 |
| —C5H11-n | H | —OC2H5 | 4-Cl | 1 | —C2H5 |
| —CH3 | —CH3 | —OC2H5 | 4-CN | 1 | —C2H5 |
| —CH3 | —CH3 | —OC2H5 | 4-C4H9-t | 1 | —C2H5 |
| —C4H9-n | H | —OC2H5 | 4-Cl | 1 | —C2H5 |
| —CH3 | —CH3 | —OC2H5 | 4-Cl | 1 | —C2H5 |
| —CH3 | —CH3 | —C2H5 | 4-Cl | 1 | —C2H5 |
| —C4H9-i | H | —OC2H5 | 4-Cl | 1 | —C2H5 |
| —CH3 | —C2H5 | —OC2H5 | 4-Cl | 1 | —C2H5 |
| —CH3 | —CH3 | —C2H5 | 4-Cl | 1 | —C2H5 |
| —CH3 | —CH3 | —C2H5 | 4-Br | 1 | —C2H5 |
| —CH3 | —CH3 | —C2H5 | 4-F | 1 | —C2H5 |
| —CH3 | —CH3 | —C2H5 | 2,4-Cl2 | 1 | —C2H5 |
| —CH3 | H | —C2H5 | 4-Cl | 1 | —C2H5 |
| —CH3 | —CH3 | —C2H5 | — | 1 | —C2H5 |
| —CH3 | —CH3 | —C2H5 | 4-CH3 | 1 | —C2H5 |
| —CH3 | —CH3 | —C2H5 | 2-F, 4-Cl | 1 | —C2H5 |
| —C2H5 | H | —C2H5 | 4-Cl | 1 | —C2H5 |
| —C2H5 | —C2H5 | —C2H5 | 4-Cl | 1 | —C2H5 |
| —C3H7-n | H | —C2H5 | 4-Cl | 1 | —C2H5 |
| —C2H5 | H | —C2H5 | 2,4-Cl2 | 1 | —C2H5 |
| —C2H5 | H | —C2H5 | 4-F | 1 | —C2H5 |
| —C2H5 | H | —C2H5 | 4-Br | 1 | —C2H5 |
| —C2H5 | H | —C2H5 | 4-NO2 | 1 | —C2H5 |
| —C2H5 | H | —C2H5 | 4-C4H9-t | 1 | —C2H5 |
| —C3H7-i | H | —C2H5 | 4-Cl | 1 | —C2H5 |
| —C5H11-n | H | —C2H5 | 4-Cl | 1 | —C2H5 |
| —CH3 | —CH3 | —C2H5 | 4-CN | 1 | —C2H5 |
| —CH3 | —CH3 | —C2H5 | 4-C4H9-t | 1 | —C2H5 |
| —C4H9-n | H | —C2H5 | 4-Cl | 1 | —C2H5 |
| —C4H9-i | H | —C2H5 | 4-Cl | 1 | —C2H5 |
| —CH3 | —C2H5 | —C2H5 | 4-Cl | 1 | —C2H5 |
| —CH3 | —CH3 | —OC2H5 | 4-OCH3 | 1 | —C2H5 |
| —CH3 | —CH3 | —OC2H5 | 2-OCH3 | 1 | —C2H5 |
| —CH3 | —CH3 | —OC2H5 | 2-CF3 | 1 | —C2H5 |
| —CH3 | —CH3 | —OC2H5 | 4-CF3 | 1 | —C2H5 |
| —CH3 | —CH3 | —OC2H5 | 2-OCF3 | 1 | —C2H5 |
| —CH3 | —CH3 | —OC2H5 | 2-OCHF2 | 1 | —C2H5 |
| —CH3 | —CH3 | —OC2H5 | 4-OCF3 | 1 | —C2H5 |
| —CH3 | —CH3 | —C2H5 | 4-OCH3 | 1 | —C2H5 |
| —CH3 | —CH3 | —C2H5 | 2-OCH3 | 1 | —C2H5 |
| —CH3 | —CH3 | —C2H5 | 2-CF3 | 1 | —C2H5 |
| —CH3 | —CH3 | —C2H5 | 4-CF3 | 1 | —C2H5 |
| —CH3 | —CH3 | —C2H5 | 2-OCF3 | 1 | —C2H5 |
| —CH3 | —CH3 | —C2H5 | 2-OCHF2 | 1 | —C2H5 |
| —CH3 | —CH3 | —C2H5 | 2-OCF3 | 1 | —C2H5 |
| —CH3 | —CH3 | —OC2H5 | 2-Cl | 0 | —C2H5 |
| —CH3 | —CH3 | —OC2H5 | 2,3-Cl2 | 0 | —C2H5 |
| —CH3 | —CH3 | —OC2H5 | 2-Cl | 1 | —C2H5 |
| —CH3 | —CH3 | —OC2H5 | 4-Cl | 0 | —C2H5 |

TABLE 5

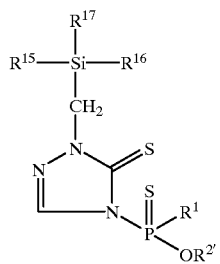

(If)

| R15 | R16 | R17 | R1 | R2' |
|---|---|---|---|---|
|  | —CH3 | —CH3 | —OC2H5 | —C2H5 |

TABLE 5-continued
(If)
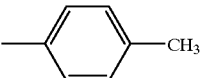
| R$^{15}$ | R$^{16}$ | R$^{17}$ | R$^1$ | R$^{2'}$ |
|---|---|---|---|---|
| 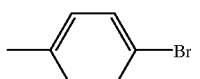 | —CH$_3$ | —CH$_3$ | —OC$_2$H$_5$ | —C$_2$H$_5$ |
| 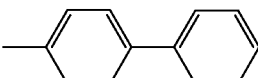 | —CH$_3$ | —CH$_3$ | —OC$_2$H$_5$ | —C$_2$H$_5$ |
| 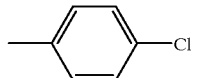 | —CH$_3$ | —CH$_3$ | —OC$_2$H$_5$ | —C$_2$H$_5$ |
| 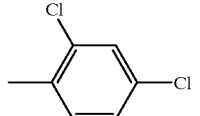 | —CH$_3$ | —CH$_3$ | —OC$_2$H$_5$ | —C$_2$H$_5$ |
|  | —CH$_3$ | —CH$_3$ | —OC$_2$H$_5$ | —C$_2$H$_5$ |
| 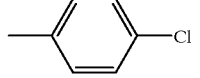 | —C$_4$H$_9$-n | —CH$_3$ | —OC$_2$H$_5$ | —C$_2$H$_5$ |
| 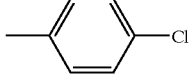 | 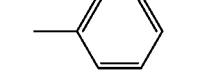 | —CH$_3$ | —OC$_2$H$_5$ | —C$_2$H$_5$ |
| 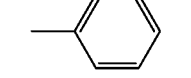 | 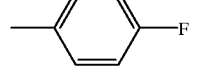 | —CH$_3$ | —OC$_2$H$_5$ | —C$_2$H$_5$ |
| 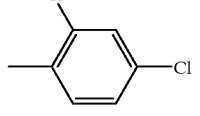 | —CH$_3$ | —CH$_3$ | —OC$_2$H$_5$ | —C$_2$H$_5$ |
|  | —C$_4$H$_9$-n | —CH$_3$ | —OC$_2$H$_5$ | —C$_2$H$_5$ |

TABLE 5-continued (If)

$$\text{structure with } R^{15}, R^{16}, R^{17} \text{ on Si-CH}_2\text{-N of triazole-thione with P(=S)(R^1)(OR^{2'})}$$

| R$^{15}$ | R$^{16}$ | R$^{17}$ | R$^1$ | R$^{2'}$ |
|---|---|---|---|---|
| 2,4-di-Cl-C$_6$H$_3$ | 2,4-di-Cl-C$_6$H$_3$ | —CH$_3$ | —OC$_2$H$_5$ | —C$_2$H$_5$ |
| 2,4-di-Cl-C$_6$H$_3$ | C$_6$H$_5$ | —CH$_3$ | —OC$_2$H$_5$ | —C$_2$H$_5$ |
| 4-Cl-C$_6$H$_4$ | C$_6$H$_5$ | —CH$_3$ | —OC$_2$H$_5$ | —C$_2$H$_5$ |
| 4-F-C$_6$H$_4$ | C$_6$H$_5$ | —CH$_3$ | —OC$_2$H$_5$ | —C$_2$H$_5$ |
| C$_6$H$_5$ | —C$_4$H$_9$-n | —CH$_3$ | —OC$_2$H$_5$ | —C$_2$H$_5$ |
| 4-F-C$_6$H$_4$ | —C$_4$H$_9$-n | —CH$_3$ | —OC$_2$H$_5$ | —C$_2$H$_5$ |
| 4-C$_6$H$_5$-C$_6$H$_4$ | 4-C$_6$H$_5$-C$_6$H$_4$ | —CH$_3$ | —OC$_2$H$_5$ | —C$_2$H$_5$ |
| 4-C$_6$H$_5$-C$_6$H$_4$ | —C$_4$H$_9$-n | —CH$_3$ | —OC$_2$H$_5$ | —C$_2$H$_5$ |
| 4-C$_6$H$_5$-C$_6$H$_4$ | C$_6$H$_5$ | —CH$_3$ | —OC$_2$H$_5$ | —C$_2$H$_5$ |
| C$_6$H$_5$ | —CH$_3$ | —CH$_3$ | —C$_2$H$_5$ | —C$_2$H$_5$ |

TABLE 5-continued
(If)
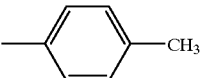
| R¹⁵ | R¹⁶ | R¹⁷ | R¹ | R²' |
|---|---|---|---|---|
| 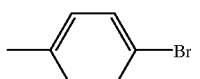 | —CH₃ | —CH₃ | —C₂H₅ | —C₂H₅ |
| 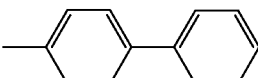 | —CH₃ | —CH₃ | —C₂H₅ | —C₂H₅ |
| 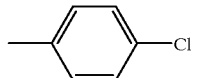 | —CH₃ | —CH₃ | —C₂H₅ | —C₂H₅ |
| 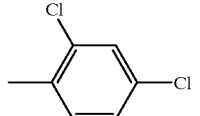 | —CH₃ | —CH₃ | —C₂H₅ | —C₂H₅ |
|  | —CH₃ | —CH₃ | —C₂H₅ | —C₂H₅ |
| 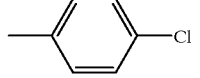 | —C₄H₉-n | —CH₃ | —C₂H₅ | —C₂H₅ |
| 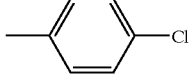 | 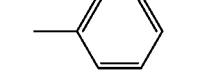 | —CH₃ | —C₂H₅ | —C₂H₅ |
| 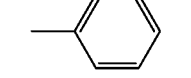 | 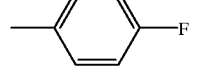 | —CH₃ | —C₂H₅ | —C₂H₅ |
| 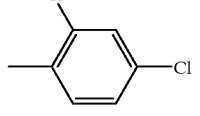 | —CH₃ | —CH₃ | —C₂H₅ | —C₂H₅ |
|  | —C₄H₉-n | —CH₃ | —C₂H₅ | —C₂H₅ |

TABLE 5-continued
(If)
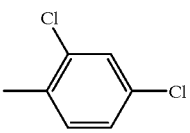
| R15 | R16 | R17 | R1 | R2' |
|---|---|---|---|---|
| 2,4-diClC6H3 | 2,4-diClC6H3 | —CH3 | —C2H5 | —C2H5 |
| 2,4-diClC6H3 | C6H5 | —CH3 | —C2H5 | —C2H5 |
| 4-ClC6H4 | C6H5 | —CH3 | —C2H5 | —C2H5 |
| 4-FC6H4 | C6H5 | —CH3 | —C2H5 | —C2H5 |
| C6H5 | —C4H9-n | —CH3 | —C2H5 | —C2H5 |
| 4-FC6H4 | —C4H9-n | —CH3 | —C2H5 | —C2H5 |
| 4-biphenyl | 4-biphenyl | —CH3 | —C2H5 | —C2H5 |
| 4-biphenyl | —C4H9-n | —CH3 | —C2H5 | —C2H5 |
| 4-biphenyl | C6H5 | —CH3 | —C2H5 | —C2H5 |
| 4-FC6H4 | 4-FC6H4 | —CH3 | —OC2H5 | —C2H5 |

TABLE 5-continued
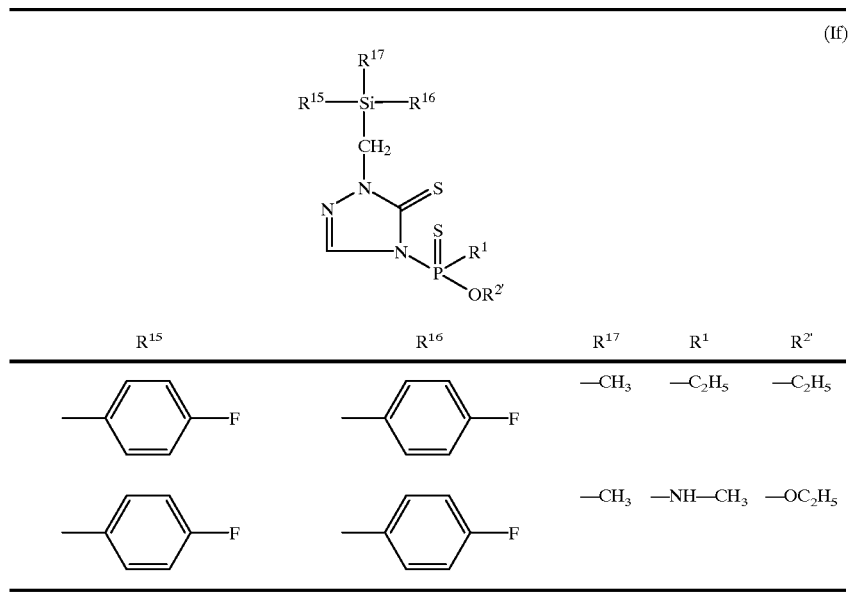
(If)
| R¹⁵ | R¹⁶ | R¹⁷ | R¹ | R²' |
|---|---|---|---|---|
| 4-F-C₆H₄– | 4-F-C₆H₄– | —CH₃ | —C₂H₅ | —C₂H₅ |
| 4-F-C₆H₄– | 4-F-C₆H₄– | —CH₃ | —NH—CH₃ | —OC₂H₅ |
TABLE 6
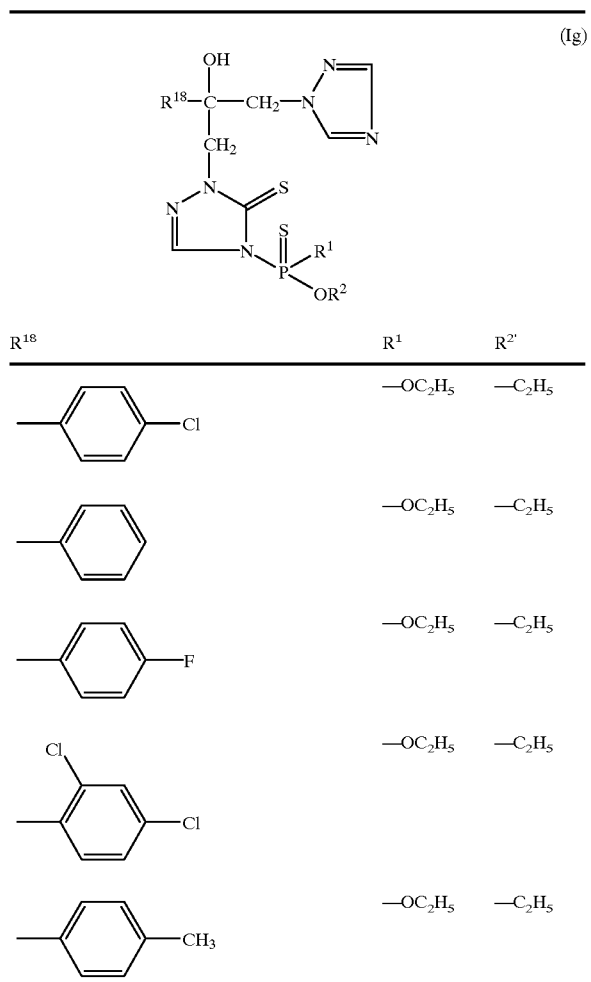
(Ig)
TABLE 6-continued
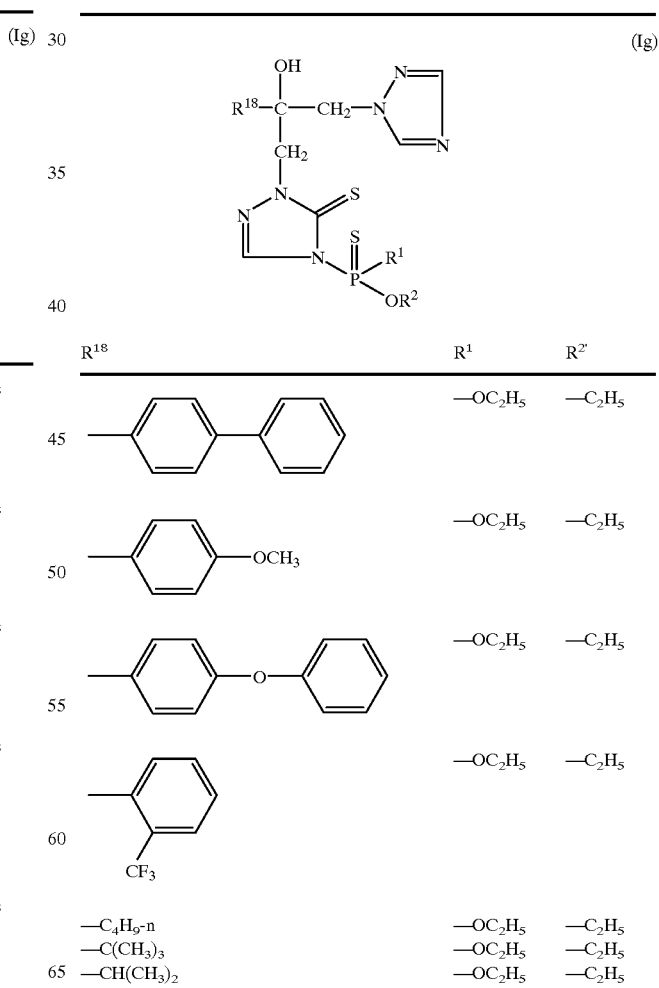
(Ig)
| R¹⁸ | R¹ | R²' |
|---|---|---|
| 4-Cl-C₆H₄– | —OC₂H₅ | —C₂H₅ |
| C₆H₅– | —OC₂H₅ | —C₂H₅ |
| 4-F-C₆H₄– | —OC₂H₅ | —C₂H₅ |
| 2,4-Cl₂-C₆H₃– | —OC₂H₅ | —C₂H₅ |
| 4-CH₃-C₆H₄– | —OC₂H₅ | —C₂H₅ |
| 4-C₆H₅-C₆H₄– | —OC₂H₅ | —C₂H₅ |
| 4-OCH₃-C₆H₄– | —OC₂H₅ | —C₂H₅ |
| 4-C₆H₅O-C₆H₄– | —OC₂H₅ | —C₂H₅ |
| 2-CF₃-C₆H₄– | —OC₂H₅ | —C₂H₅ |
| —C₄H₉-n | —OC₂H₅ | —C₂H₅ |
| —C(CH₃)₃ | —OC₂H₅ | —C₂H₅ |
| —CH(CH₃)₂ | —OC₂H₅ | —C₂H₅ |

TABLE 6-continued
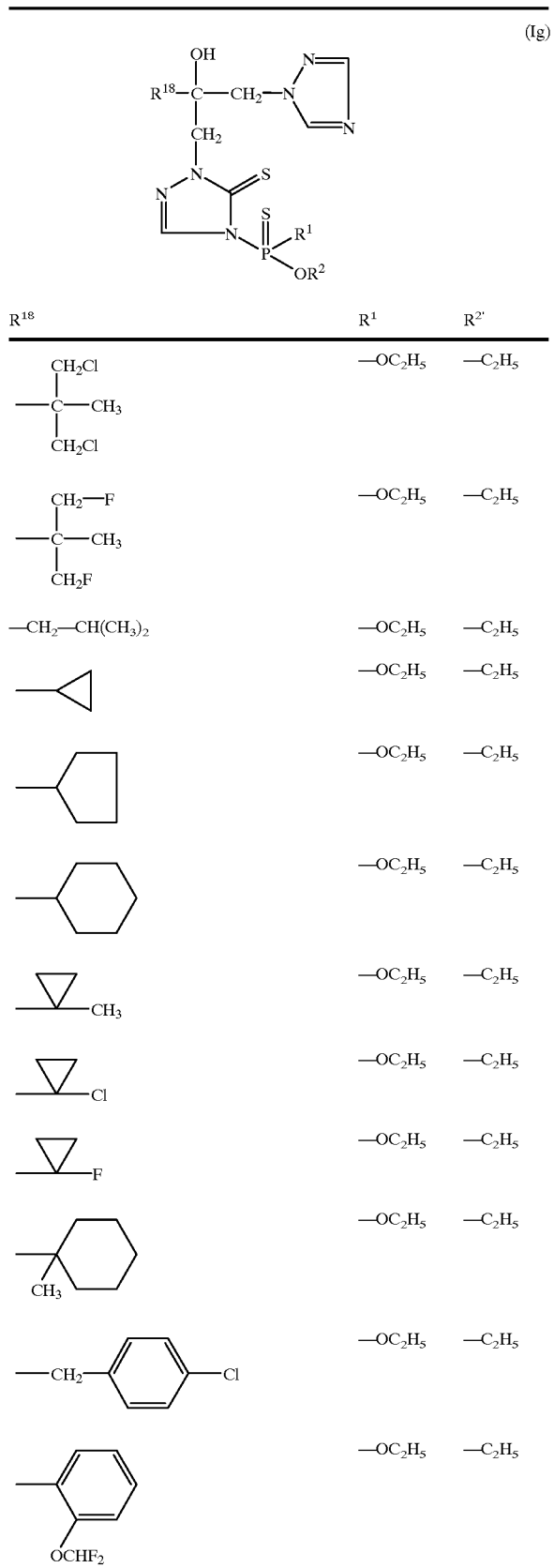
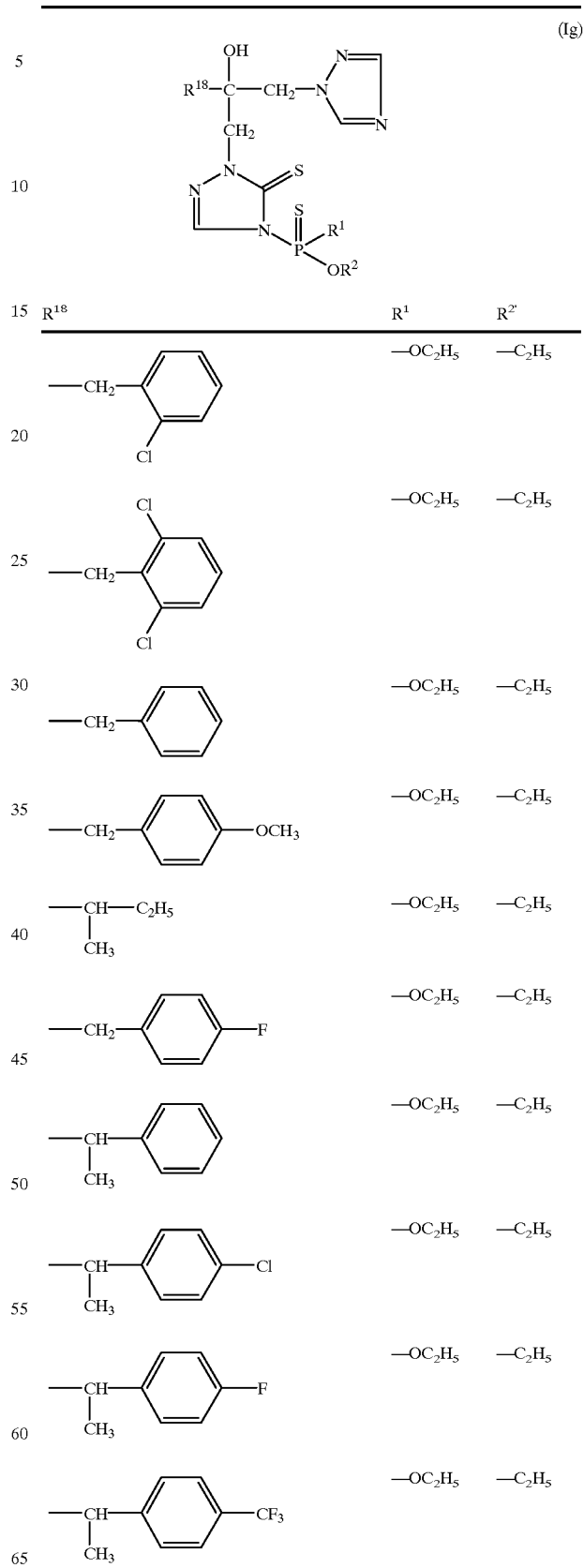

TABLE 6-continued
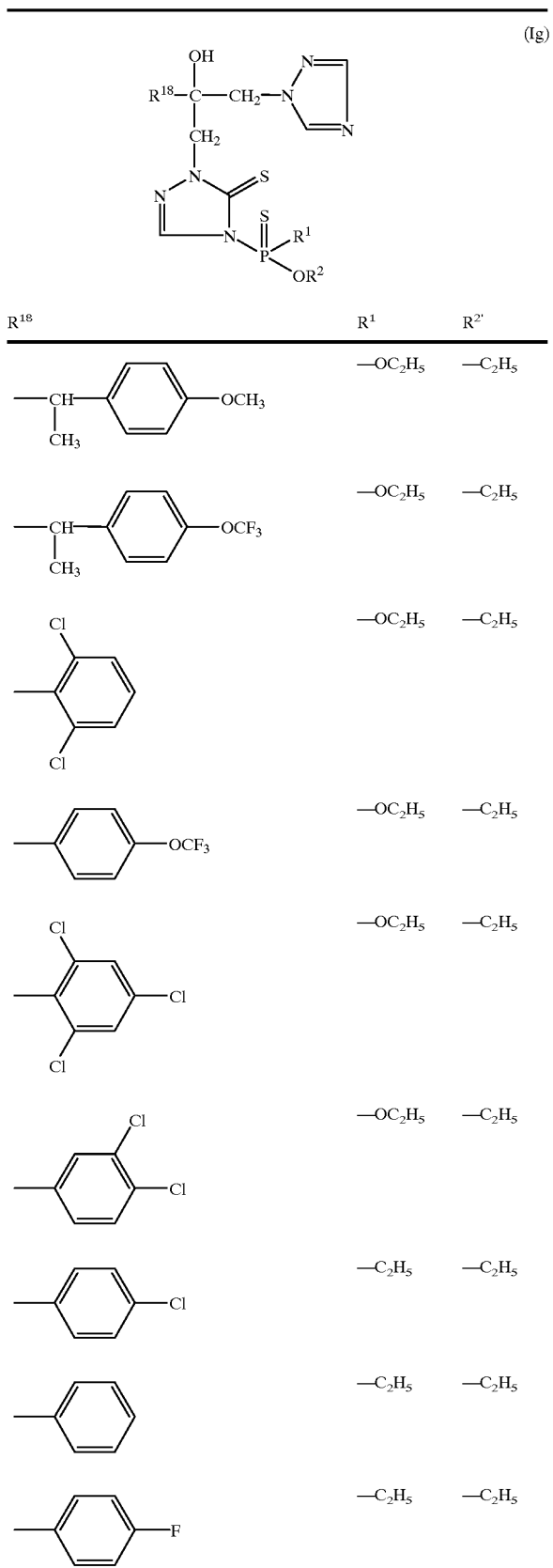
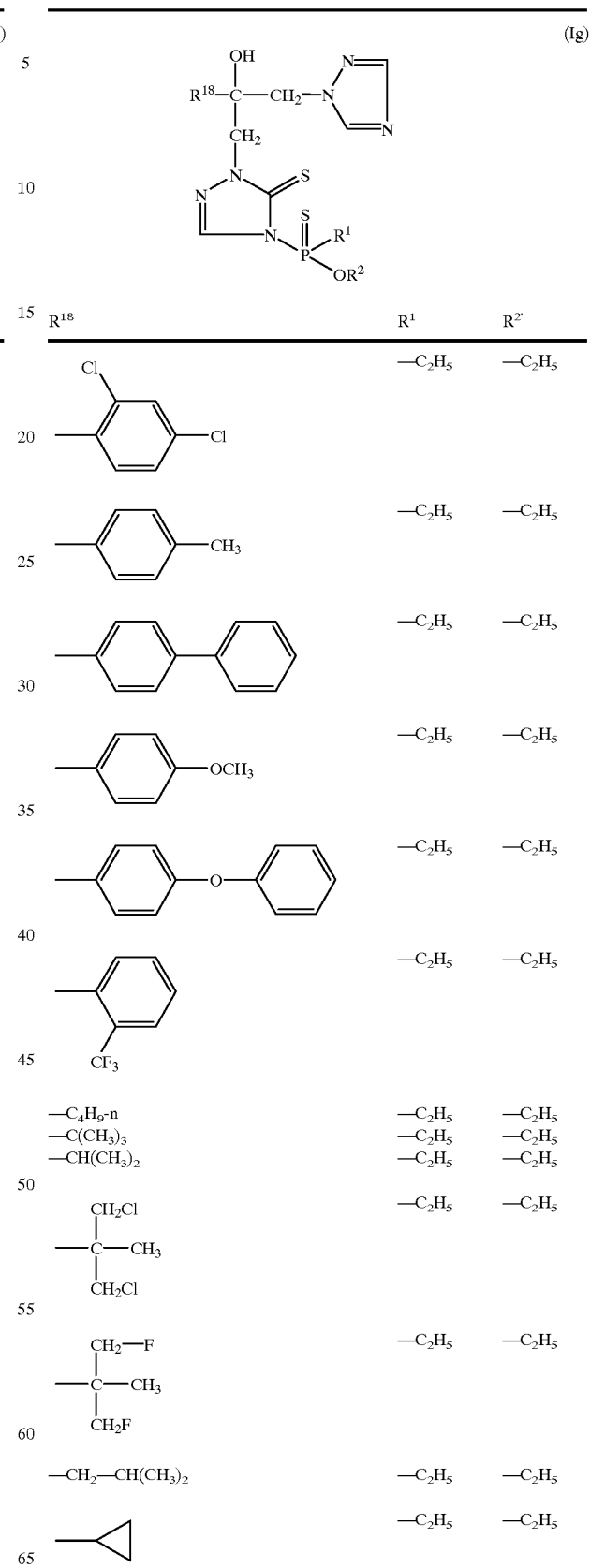

TABLE 6-continued
(Ig)
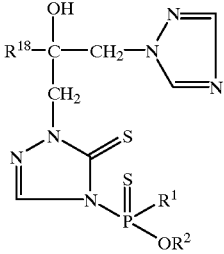
| R[18] | R[1] | R[2'] |
|---|---|---|
| 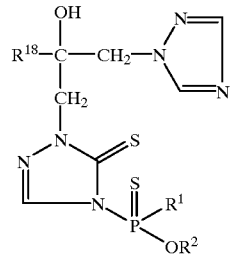 | —C$_2$H$_5$ | —C$_2$H$_5$ |
| 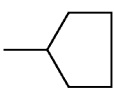 | —C$_2$H$_5$ | —C$_2$H$_5$ |
| 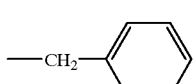 | —C$_2$H$_5$ | —C$_2$H$_5$ |
| 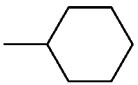 | —C$_2$H$_5$ | —C$_2$H$_5$ |
| 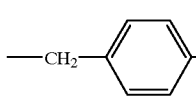 | —C$_2$H$_5$ | —C$_2$H$_5$ |
| 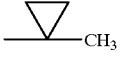 | —C$_2$H$_5$ | —C$_2$H$_5$ |
| 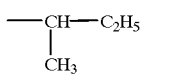 | —C$_2$H$_5$ | —C$_2$H$_5$ |
| 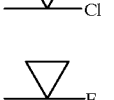 | —C$_2$H$_5$ | —C$_2$H$_5$ |
| 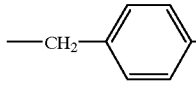 | —C$_2$H$_5$ | —C$_2$H$_5$ |
| 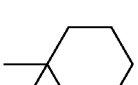 | —C$_2$H$_5$ | —C$_2$H$_5$ |
TABLE 6-continued
(Ig)
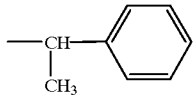
| R[18] | R[1] | R[2'] |
|---|---|---|
| 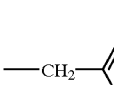 | —C$_2$H$_5$ | —C$_2$H$_5$ |
| 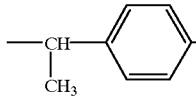 | —C$_2$H$_5$ | —C$_2$H$_5$ |
| 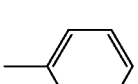 | —C$_2$H$_5$ | —C$_2$H$_5$ |
| 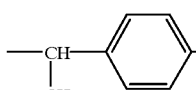 | —C$_2$H$_5$ | —C$_2$H$_5$ |
| 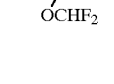 | —C$_2$H$_5$ | —C$_2$H$_5$ |
| 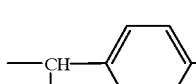 | —C$_2$H$_5$ | —C$_2$H$_5$ |
|  | —C$_2$H$_5$ | —C$_2$H$_5$ |
| 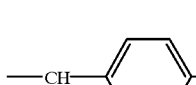 | —C$_2$H$_5$ | —C$_2$H$_5$ |
| 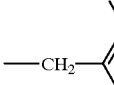 | —C$_2$H$_5$ | —C$_2$H$_5$ |
| 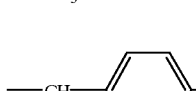 | —C$_2$H$_5$ | —C$_2$H$_5$ |

TABLE 6-continued (Ig)

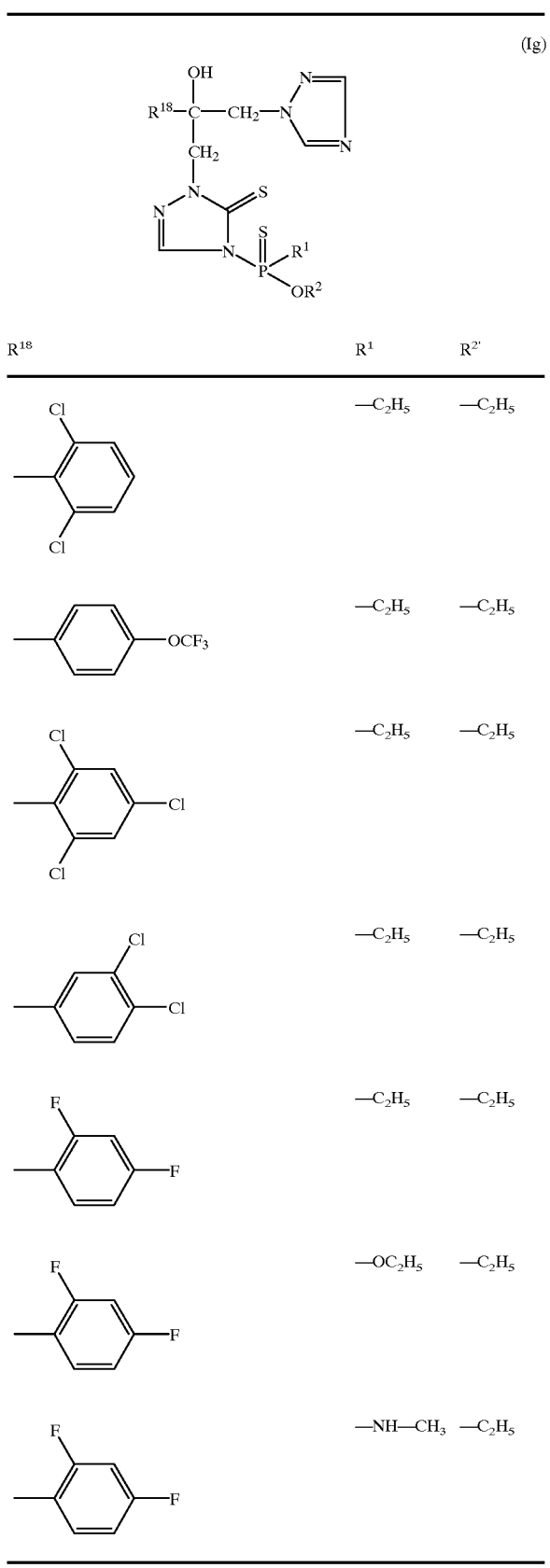

| R[18] | R[1] | R[2'] |
|---|---|---|
| 2,6-dichlorophenyl | —C$_2$H$_5$ | —C$_2$H$_5$ |
| 4-OCF$_3$-phenyl | —C$_2$H$_5$ | —C$_2$H$_5$ |
| 2,4,6-trichlorophenyl | —C$_2$H$_5$ | —C$_2$H$_5$ |
| 3,4-dichlorophenyl | —C$_2$H$_5$ | —C$_2$H$_5$ |
| 2,4-difluorophenyl | —C$_2$H$_5$ | —C$_2$H$_5$ |
| 2,4-difluorophenyl | —OC$_2$H$_5$ | —C$_2$H$_5$ |
| 2,4-difluorophenyl | —NH—CH$_3$ | —C$_2$H$_5$ |

TABLE 7

(Ih)

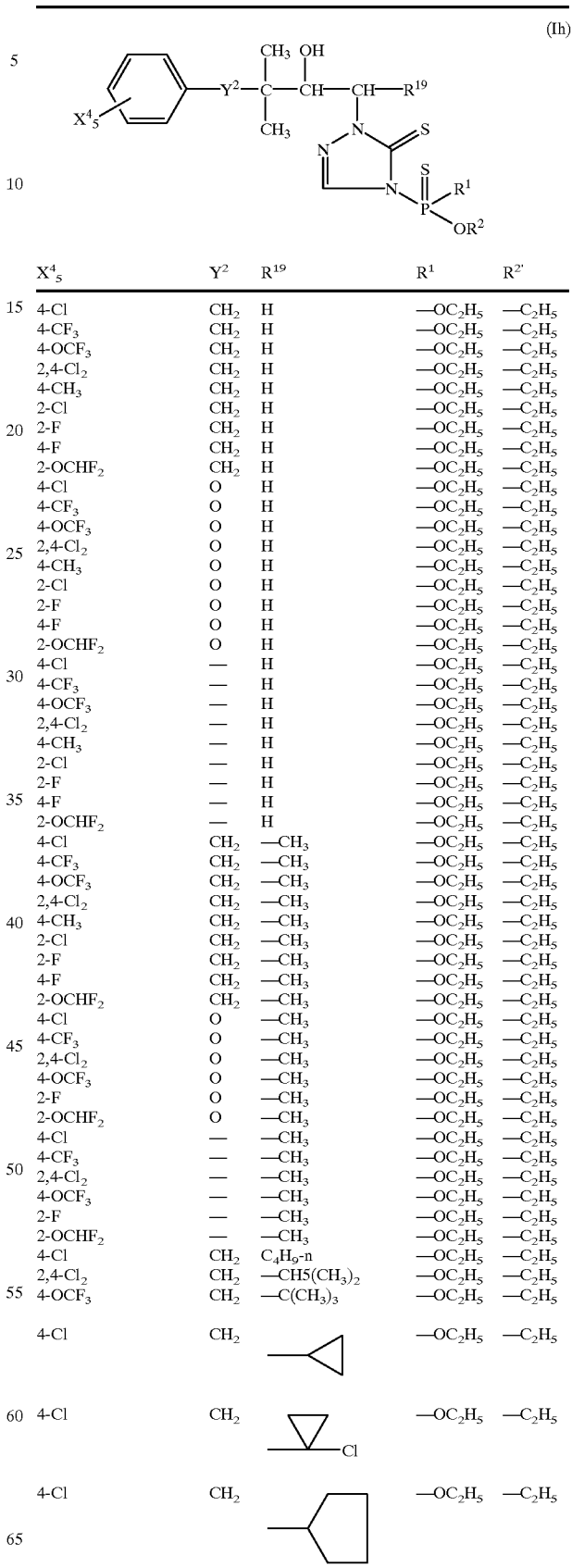

| X$^4_5$ | Y$^2$ | R[19] | R[1] | R[2'] |
|---|---|---|---|---|
| 4-Cl | CH$_2$ | H | —OC$_2$H$_5$ | —C$_2$H$_5$ |
| 4-CF$_3$ | CH$_2$ | H | —OC$_2$H$_5$ | —C$_2$H$_5$ |
| 4-OCF$_3$ | CH$_2$ | H | —OC$_2$H$_5$ | —C$_2$H$_5$ |
| 2,4-Cl$_2$ | CH$_2$ | H | —OC$_2$H$_5$ | —C$_2$H$_5$ |
| 4-CH$_3$ | CH$_2$ | H | —OC$_2$H$_5$ | —C$_2$H$_5$ |
| 2-Cl | CH$_2$ | H | —OC$_2$H$_5$ | —C$_2$H$_5$ |
| 2-F | CH$_2$ | H | —OC$_2$H$_5$ | —C$_2$H$_5$ |
| 4-F | CH$_2$ | H | —OC$_2$H$_5$ | —C$_2$H$_5$ |
| 2-OCHF$_2$ | CH$_2$ | H | —OC$_2$H$_5$ | —C$_2$H$_5$ |
| 4-Cl | O | H | —OC$_2$H$_5$ | —C$_2$H$_5$ |
| 4-CF$_3$ | O | H | —OC$_2$H$_5$ | —C$_2$H$_5$ |
| 4-OCF$_3$ | O | H | —OC$_2$H$_5$ | —C$_2$H$_5$ |
| 2,4-Cl$_2$ | O | H | —OC$_2$H$_5$ | —C$_2$H$_5$ |
| 4-CH$_3$ | O | H | —OC$_2$H$_5$ | —C$_2$H$_5$ |
| 2-Cl | O | H | —OC$_2$H$_5$ | —C$_2$H$_5$ |
| 2-F | O | H | —OC$_2$H$_5$ | —C$_2$H$_5$ |
| 4-F | O | H | —OC$_2$H$_5$ | —C$_2$H$_5$ |
| 2-OCHF$_2$ | O | H | —OC$_2$H$_5$ | —C$_2$H$_5$ |
| 4-Cl | — | H | —OC$_2$H$_5$ | —C$_2$H$_5$ |
| 4-CF$_3$ | — | H | —OC$_2$H$_5$ | —C$_2$H$_5$ |
| 4-OCF$_3$ | — | H | —OC$_2$H$_5$ | —C$_2$H$_5$ |
| 2,4-Cl$_2$ | — | H | —OC$_2$H$_5$ | —C$_2$H$_5$ |
| 4-CH$_3$ | — | H | —OC$_2$H$_5$ | —C$_2$H$_5$ |
| 2-Cl | — | H | —OC$_2$H$_5$ | —C$_2$H$_5$ |
| 2-F | — | H | —OC$_2$H$_5$ | —C$_2$H$_5$ |
| 4-F | — | H | —OC$_2$H$_5$ | —C$_2$H$_5$ |
| 2-OCHF$_2$ | — | H | —OC$_2$H$_5$ | —C$_2$H$_5$ |
| 4-Cl | CH$_2$ | —CH$_3$ | —OC$_2$H$_5$ | —C$_2$H$_5$ |
| 4-CF$_3$ | CH$_2$ | —CH$_3$ | —OC$_2$H$_5$ | —C$_2$H$_5$ |
| 4-OCF$_3$ | CH$_2$ | —CH$_3$ | —OC$_2$H$_5$ | —C$_2$H$_5$ |
| 2,4-Cl$_2$ | CH$_2$ | —CH$_3$ | —OC$_2$H$_5$ | —C$_2$H$_5$ |
| 4-CH$_3$ | CH$_2$ | —CH$_3$ | —OC$_2$H$_5$ | —C$_2$H$_5$ |
| 2-Cl | CH$_2$ | —CH$_3$ | —OC$_2$H$_5$ | —C$_2$H$_5$ |
| 2-F | CH$_2$ | —CH$_3$ | —OC$_2$H$_5$ | —C$_2$H$_5$ |
| 4-F | CH$_2$ | —CH$_3$ | —OC$_2$H$_5$ | —C$_2$H$_5$ |
| 2-OCHF$_2$ | CH$_2$ | —CH$_3$ | —OC$_2$H$_5$ | —C$_2$H$_5$ |
| 4-Cl | O | —CH$_3$ | —OC$_2$H$_5$ | —C$_2$H$_5$ |
| 4-CF$_3$ | O | —CH$_3$ | —OC$_2$H$_5$ | —C$_2$H$_5$ |
| 2,4-Cl$_2$ | O | —CH$_3$ | —OC$_2$H$_5$ | —C$_2$H$_5$ |
| 4-OCF$_3$ | O | —CH$_3$ | —OC$_2$H$_5$ | —C$_2$H$_5$ |
| 2-F | O | —CH$_3$ | —OC$_2$H$_5$ | —C$_2$H$_5$ |
| 2-OCHF$_2$ | O | —CH$_3$ | —OC$_2$H$_5$ | —C$_2$H$_5$ |
| 4-Cl | — | —CH$_3$ | —OC$_2$H$_5$ | —C$_2$H$_5$ |
| 4-CF$_3$ | — | —CH$_3$ | —OC$_2$H$_5$ | —C$_2$H$_5$ |
| 2,4-Cl$_2$ | — | —CH$_3$ | —OC$_2$H$_5$ | —C$_2$H$_5$ |
| 4-OCF$_3$ | — | —CH$_3$ | —OC$_2$H$_5$ | —C$_2$H$_5$ |
| 2-F | — | —CH$_3$ | —OC$_2$H$_5$ | —C$_2$H$_5$ |
| 2-OCHF$_2$ | — | —CH$_3$ | —OC$_2$H$_5$ | —C$_2$H$_5$ |
| 4-Cl | CH$_2$ | C$_4$H$_9$-n | —OC$_2$H$_5$ | —C$_2$H$_5$ |
| 2,4-Cl$_2$ | CH$_2$ | —CH5(CH$_3$)$_2$ | —OC$_2$H$_5$ | —C$_2$H$_5$ |
| 4-OCF$_3$ | CH$_2$ | —C(CH$_3$)$_3$ | —OC$_2$H$_5$ | —C$_2$H$_5$ |
| 4-Cl | CH$_2$ | cyclopropyl | —OC$_2$H$_5$ | —C$_2$H$_5$ |
| 4-Cl | CH$_2$ | chlorocyclopropyl | —OC$_2$H$_5$ | —C$_2$H$_5$ |
| 4-Cl | CH$_2$ | cyclopentyl | —OC$_2$H$_5$ | —C$_2$H$_5$ |

TABLE 7-continued

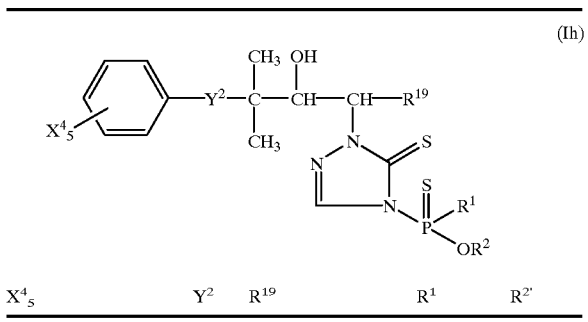

(Ih)

| $X^4_5$ | $Y^2$ | $R^{19}$ | $R^1$ | $R^{2'}$ |
|---|---|---|---|---|
| 4-Cl | $CH_2$ | cyclohexyl-CH₂ | $-OC_2H_5$ | $-C_2H_5$ |
| 2,4,6-$Cl_3$ | $CH_2$ | $-CH_3$ | $-OC_2H_5$ | $-C_2H_5$ |
| 4-phenyl | $CH_2$ | $-CH_3$ | $-OC_2H_5$ | $-C_2H_5$ |
| 4-O-phenyl | $CH_2$ | $-CH_3$ | $-OC_2H_5$ | $-C_2H_5$ |
| 4-Cl | $CH_2$ | H | $-C_2H_5$ | $-C_2H_5$ |
| 4-$CF_3$ | $CH_2$ | H | $-C_2H_5$ | $-C_2H_5$ |
| 4-$OCF_3$ | $CH_2$ | H | $-C_2H_5$ | $-C_2H_5$ |
| 2,4-$Cl_2$ | $CH_2$ | H | $-C_2H_5$ | $-C_2H_5$ |
| 4-$CH_3$ | $CH_2$ | H | $-C_2H_5$ | $-C_2H_5$ |
| 2-Cl | $CH_2$ | H | $-C_2H_5$ | $-C_2H_5$ |
| 2-F | $CH_2$ | H | $-C_2H_5$ | $-C_2H_5$ |
| 4-F | $CH_2$ | H | $-C_2H_5$ | $-C_2H_5$ |
| 2-$OCHF_2$ | $CH_2$ | H | $-C_2H_5$ | $-C_2H_5$ |
| 4-Cl | O | H | $-C_2H_5$ | $-C_2H_5$ |
| 4-$CF_3$ | O | H | $-C_2H_5$ | $-C_2H_5$ |
| 4-$OCF_3$ | O | H | $-C_2H_5$ | $-C_2H_5$ |
| 2,4-$Cl_2$ | O | H | $-C_2H_5$ | $-C_2H_5$ |
| 4-$CH_3$ | O | H | $-C_2H_5$ | $-C_2H_5$ |
| 2-Cl | O | H | $-C_2H_5$ | $-C_2H_5$ |
| 2-F | O | H | $-C_2H_5$ | $-C_2H_5$ |
| 4-F | O | H | $-C_2H_5$ | $-C_2H_5$ |
| 2-$OCHF_2$ | O | H | $-C_2H_5$ | $-C_2H_5$ |
| 4-Cl | — | H | $-C_2H_5$ | $-C_2H_5$ |
| 4-$CF_3$ | — | H | $-C_2H_5$ | $-C_2H_5$ |
| 4-$OCF_3$ | — | H | $-C_2H_5$ | $-C_2H_5$ |
| 2,4-$Cl_2$ | — | H | $-C_2H_5$ | $-C_2H_5$ |
| 4-$CH_3$ | — | H | $-C_2H_5$ | $-C_2H_5$ |
| 2-Cl | — | H | $-C_2H_5$ | $-C_2H_5$ |
| 2-F | — | H | $-C_2H_5$ | $-C_2H_5$ |
| 4-F | — | H | $-C_2H_5$ | $-C_2H_5$ |
| 2-$OCHF_2$ | — | H | $-C_2H_5$ | $-C_2H_5$ |
| 4-Cl | $CH_2$ | $-CH_3$ | $-C_2H_5$ | $-C_2H_5$ |
| 4-$CF_3$ | $CH_2$ | $-CH_3$ | $-C_2H_5$ | $-C_2H_5$ |
| 4-$OCF_3$ | $CH_2$ | $-CH_3$ | $-C_2H_5$ | $-C_2H_5$ |
| 2,4-$Cl_2$ | $CH_2$ | $-CH_3$ | $-C_2H_5$ | $-C_2H_5$ |
| 4-$CH_3$ | $CH_2$ | $-CH_3$ | $-C_2H_5$ | $-C_2H_5$ |
| 2-Cl | $CH_2$ | $-CH_3$ | $-C_2H_5$ | $-C_2H_5$ |
| 2-F | $CH_2$ | $-CH_3$ | $-C_2H_5$ | $-C_2H_5$ |
| 4-F | $CH_2$ | $-CH_3$ | $-C_2H_5$ | $-C_2H_5$ |
| 2-$OCHF_2$ | $CH_2$ | $-CH_3$ | $-C_2H_5$ | $-C_2H_5$ |
| 4-Cl | O | $-CH_3$ | $-C_2H_5$ | $-C_2H_5$ |
| 4-$CF_3$ | O | $-CH_3$ | $-C_2H_5$ | $-C_2H_5$ |
| 2,4-$Cl_2$ | O | $-CH_3$ | $-C_2H_5$ | $-C_2H_5$ |
| 4-$OCF_3$ | O | $-CH_3$ | $-C_2H_5$ | $-C_2H_5$ |
| 2-F | O | $-CH_3$ | $-C_2H_5$ | $-C_2H_5$ |
| 2-$OCHF_2$ | O | $-CH_3$ | $-C_2H_5$ | $-C_2H_5$ |
| 4-Cl | — | $-CH_3$ | $-C_2H_5$ | $-C_2H_5$ |
| 4-$CF_3$ | — | $-CH_3$ | $-C_2H_5$ | $-C_2H_5$ |
| 2,4-$Cl_2$ | — | $-CH_3$ | $-C_2H_5$ | $-C_2H_5$ |

TABLE 7-continued

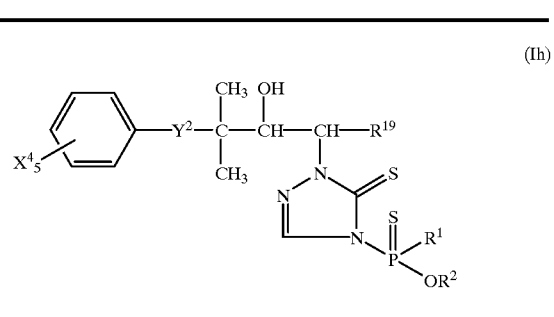

(Ih)

| $X^4_5$ | $Y^2$ | $R^{19}$ | $R^1$ | $R^{2'}$ |
|---|---|---|---|---|
| 4-$OCF_3$ | — | $-CH_3$ | $-C_2H_5$ | $-C_2H_5$ |
| 2-F | — | $-CH_3$ | $-C_2H_5$ | $-C_2H_5$ |
| 2-$OCHF_2$ | — | $-CH_3$ | $-C_2H_5$ | $-C_2H_5$ |
| 4-Cl | $CH_2$ | $C_4H_9$-n | $-C_2H_5$ | $-C_2H_5$ |
| 2,4-$Cl_2$ | $CH_2$ | $-CH(CH_3)_2$ | $-C_2H_5$ | $-C_2H_5$ |
| 4-$OCF_3$ | $CH_2$ | $-C(CH_3)_3$ | $-C_2H_5$ | $-C_2H_5$ |
| 4-Cl | $CH_2$ | cyclopropyl | $-C_2H_5$ | $-C_2H_5$ |
| 4-Cl | $CH_2$ | cyclopropyl-Cl | $-C_2H_5$ | $-C_2H_5$ |
| 4-Cl | $CH_2$ | cyclopentyl | $-C_2H_5$ | $-C_2H_5$ |
| 4-Cl | $CH_2$ | cyclohexyl | $-C_2H_5$ | $-C_2H_5$ |
| 2,4,6-$Cl_3$ | $CH_2$ | $-CH_3$ | $-C_2H_5$ | $-C_2H_5$ |
| 4-phenyl | $CH_2$ | $-CH_3$ | $-C_2H_5$ | $-C_2H_5$ |
| 4-O-phenyl | $CH_2$ | $-CH_3$ | $-C_2H_5$ | $-C_2H_5$ |
| 4-$OCF_3$ | $CH_2$ | $-CH_3$ | $-C_2H_5$ | $-C_2H_5$ |

TABLE 8

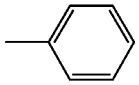

(Ii)

| $X^5_t$ | $R^{20}$ | $R^1$ | $Y^3$ | $R^{2'}$ |
|---|---|---|---|---|
| 2,4-Cl$_2$ | 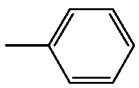 | —OC$_2$H$_5$ | O | —C$_2$H$_5$ |
| 4-Cl | 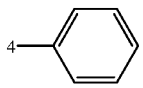 | —OC$_2$H$_5$ | O | —C$_2$H$_5$ |
| 4-Br | —C(CH$_3$)$_3$ | —OC$_2$H$_5$ | O | —C$_2$H$_5$ |
| — | —C(CH$_3$)$_3$ | —OC$_2$H$_5$ | O | —C$_2$H$_5$ |
| 4-C(CH$_3$)$_3$ | —C(CH$_3$)$_3$ | —OC$_2$H$_5$ | O | —C$_2$H$_5$ |
| 2-Cl | —C(CH$_3$)$_3$ | —OC$_2$H$_5$ | O | —C$_2$H$_5$ |
| 3-Cl | —C(CH$_3$)$_3$ | —OC$_2$H$_5$ | O | —C$_2$H$_5$ |
| 4-F | —C(CH$_3$)$_3$ | —OC$_2$H$_5$ | O | —C$_2$H$_5$ |
| 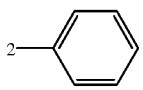 | —C(CH$_3$)$_3$ | —OC$_2$H$_5$ | O | —C$_2$H$_5$ |
| 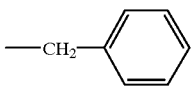 | —C(CH$_3$)$_3$ | —OC$_2$H$_5$ | O | —C$_2$H$_5$ |
| 2,4-Cl$_2$ | —C(CH$_3$)$_3$ | —OC$_2$H$_5$ | O | —C$_2$H$_5$ |
| 2-CH$_3$, 4-Cl | —C(CH$_3$)$_3$ | —OC$_2$H$_5$ | O | —C$_2$H$_5$ |
| 3,4-(CH$_3$)$_2$ | —C(CH$_3$)$_3$ | —OC$_2$H$_5$ | O | —C$_2$H$_5$ |
| 2,4,5-Cl$_3$ | —C(CH$_3$)$_3$ | —OC$_2$H$_5$ | O | —C$_2$H$_5$ |
| 4-Cl | —CH$_3$ | —OC$_2$H$_5$ | O | —C$_2$H$_5$ |
| 4-Cl | 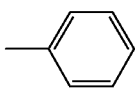 | —OC$_2$H$_5$ | O | —C$_2$H$_5$ |
| 4-CF$_3$ | —C(CH$_3$)$_3$ | —OC$_2$H$_5$ | O | —C$_2$H$_5$ |
| 4-OCF$_3$ | —C(CH$_3$)$_3$ | —OC$_2$H$_5$ | O | —C$_2$H$_5$ |
| 2-OCHF$_2$ | —C(CH$_3$)$_3$ | —OC$_2$H$_5$ | O | —C$_2$H$_5$ |
| 4-OCH$_3$ | —C(CH$_3$)$_3$ | —OC$_2$H$_5$ | O | —C$_2$H$_5$ |
| 2,4-Cl$_2$ | 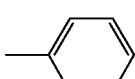 | —C$_2$H$_5$ | O | —C$_2$H$_5$ |
| 4-Cl | 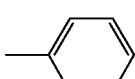 | —C$_2$H$_5$ | O | —C$_2$H$_5$ |
| 4-Br | —C(CH$_3$)$_3$ | —C$_2$H$_5$ | O | —C$_2$H$_5$ |
| — | —C(CH$_3$)$_3$ | —C$_2$H$_5$ | O | —C$_2$H$_5$ |
| 4-C(CH$_3$)$_3$ | —C(CH$_3$)$_3$ | —C$_2$H$_5$ | O | —C$_2$H$_5$ |
| 2-Cl | —C(CH$_3$)$_3$ | —C$_2$H$_5$ | O | —C$_2$H$_5$ |
| 3-Cl | —C(CH$_3$)$_3$ | —C$_2$H$_5$ | O | —C$_2$H$_5$ |
| 4-F | —C(CH$_3$)$_3$ | —C$_2$H$_5$ | O | —C$_2$H$_5$ |

TABLE 8-continued (Ii)

$$\begin{array}{c} X^5_t\text{-Ph-}Y^3\text{-CH(N-triazole-thione-P(=S)(R^1)(OR^2))-CH(OH)-R^{20}} \end{array}$$

| $X^5_t$ | $R^{20}$ | $R^1$ | $Y^3$ | $R^{2'}$ |
|---|---|---|---|---|
| 4-Ph | —C(CH$_3$)$_3$ | —C$_2$H$_5$ | O | —C$_2$H$_5$ |
| 2-Ph | —C(CH$_3$)$_3$ | —C$_2$H$_5$ | O | —C$_2$H$_5$ |
| 2,4-Cl$_2$ | —C(CH$_3$)$_3$ | —C$_2$H$_5$ | O | —C$_2$H$_5$ |
| 2-CH$_3$, 4-Cl | —C(CH$_3$)$_3$ | —C$_2$H$_5$ | O | —C$_2$H$_5$ |
| 3,4-(CH$_3$)$_2$ | —C(CH$_3$)$_3$ | —C$_2$H$_5$ | O | —C$_2$H$_5$ |
| 2,4,5-Cl$_3$ | —C(CH$_3$)$_3$ | —C$_2$H$_5$ | O | —C$_2$H$_5$ |
| 4-Cl | —CH$_3$ | —C$_2$H$_5$ | O | —C$_2$H$_5$ |
| 4-Cl | —CH$_2$-Ph | —C$_2$H$_5$ | O | —C$_2$H$_5$ |
| 4-CF$_3$ | —C(CH$_3$)$_3$ | —C$_2$H$_5$ | O | —C$_2$H$_5$ |
| 4-OCF$_3$ | —C(CH$_3$)$_3$ | —C$_2$H$_5$ | O | —C$_2$H$_5$ |
| 2-OCHF$_2$ | —C(CH$_3$)$_3$ | —C$_2$H$_5$ | O | —C$_2$H$_5$ |
| 4-OCH$_3$ | —C(CH$_3$)$_3$ | —C$_2$H$_5$ | O | —C$_2$H$_5$ |
| 4-Cl | —C(CH$_3$)$_2$CH$_2$F | —OC$_2$H$_5$ | O | —C$_2$H$_5$ |
| 4-Cl | —C(CH$_2$F)$_2$CH$_3$ | —OC$_2$H$_5$ | O | —C$_2$H$_5$ |
| 4-Cl | —C(CH$_3$)$_2$CH$_2$F | —C$_2$H$_5$ | O | —C$_2$H$_5$ |
| 4-Cl | —C(CH$_2$F)$_2$CH$_3$ | —C$_2$H$_5$ | O | —C$_2$H$_5$ |
| 2,4-Cl$_2$ | —Ph | —OC$_2$H$_5$ | CH$_2$ | —C$_2$H$_5$ |
| 4-Cl | —Ph | —OC$_2$H$_5$ | CH$_2$ | —C$_2$H$_5$ |

TABLE 8-continued

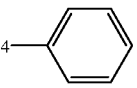
(Ii)

| X⁵ₜ | R²⁰ | R¹ | Y³ | R²' |
|---|---|---|---|---|
| 4-Br | —C(CH₃)₃ | —OC₂H₅ | CH₂ | —C₂H₅ |
| — | —C(CH₃)₃ | —OC₂H₅ | CH₂ | —C₂H₅ |
| 4-C(CH₃)₃ | —C(CH₃)₃ | —OC₂H₅ | CH₂ | —C₂H₅ |
| 2-Cl | —C(CH₃)₃ | —OC₂H₅ | CH₂ | —C₂H₅ |
| 3-Cl | —C(CH₃)₃ | —OC₂H₅ | CH₂ | —C₂H₅ |
| 4-F | —C(CH₃)₃ | —OC₂H₅ | CH₂ | —C₂H₅ |
| 4-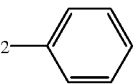 | —C(CH₃)₃ | —OC₂H₅ | CH₂ | —C₂H₅ |
| 2-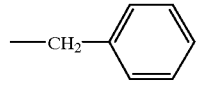 | —C(CH₃)₃ | —OC₂H₅ | CH₂ | —C₂H₅ |
| 2,4-Cl₂ | —C(CH₃)₃ | —OC₂H₅ | CH₂ | —C₂H₅ |
| 2-CH₃, 4-Cl | —C(CH₃)₃ | —OC₂H₅ | CH₂ | —C₂H₅ |
| 3,4-(CH₃)₂ | —C(CH₃)₃ | —OC₂H₅ | CH₂ | —C₂H₅ |
| 2,4,5-Cl₃ | —C(CH₃)₃ | —OC₂H₅ | CH₂ | —C₂H₅ |
| 4-Cl | —CH₃ | —OC₂H₅ | CH₂ | —C₂H₅ |
| 4-Cl | —CH₂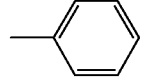 | —OC₂H₅ | CH₂ | —C₂H₅ |
| 4-CF₃ | —C(CH₃)₃ | —OC₂H₅ | CH₂ | —C₂H₅ |
| 4-OCF₃ | —C(CH₃)₃ | —OC₂H₅ | CH₂ | —C₂H₅ |
| 2-OCHF₂ | —C(CH₃)₃ | —OC₂H₅ | CH₂ | —C₂H₅ |
| 4-OCH₃ | —C(CH₃)₃ | —OC₂H₅ | CH₂ | —C₂H₅ |
| 2,4-Cl₂ | 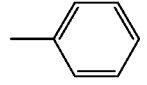 | —C₂H₅ | CH₂ | —C₂H₅ |
| 4-Cl | 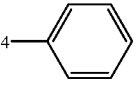 | —C₂H₅ | CH₂ | —C₂H₅ |
| 4-Br | —C(CH₃)₃ | —C₂H₅ | CH₂ | —C₂H₅ |
| — | —C(CH₃)₃ | —C₂H₅ | CH₂ | —C₂H₅ |
| 4-C(CH₃)₃ | —C(CH₃)₃ | —C₂H₅ | CH₂ | —C₂H₅ |
| 2-Cl | —C(CH₃)₃ | —C₂H₅ | CH₂ | —C₂H₅ |
| 3-Cl | —C(CH₃)₃ | —C₂H₅ | CH₂ | —C₂H₅ |
| 4-F | —C(CH₃)₃ | —C₂H₅ | CH₂ | —C₂H₅ |
| 4-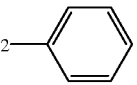 | —C(CH₃)₃ | —C₂H₅ | CH₂ | —C₂H₅ |
| 2- | —C(CH₃)₃ | —C₂H₅ | CH₂ | —C₂H₅ |
| 2,4-Cl₂ | —C(CH₃)₃ | —C₂H₅ | CH₂ | —C₂H₅ |

TABLE 8-continued (Ii)

| $X^5_t$ | $R^{20}$ | $R^1$ | $Y^3$ | $R^{2'}$ |
|---|---|---|---|---|
| 2-CH$_3$, 4-Cl | —C(CH$_3$)$_3$ | —C$_2$H$_5$ | CH$_2$ | —C$_2$H$_5$ |
| 3,4-(CH$_3$)$_2$ | —C(CH$_3$)$_3$ | —C$_2$H$_5$ | CH$_2$ | —C$_2$H$_5$ |
| 2,4,5-Cl$_3$ | —C(CH$_3$)$_3$ | —C$_2$H$_5$ | CH$_2$ | —C$_2$H$_5$ |
| 4-Cl | —CH$_3$ | —C$_2$H$_5$ | CH$_2$ | —C$_2$H$_5$ |
| 4-Cl | —CH$_2$–C$_6$H$_5$ (benzyl) | —C$_2$H$_5$ | CH$_2$ | —C$_2$H$_5$ |
| 4-CF$_3$ | —C(CH$_3$)$_3$ | —C$_2$H$_5$ | CH$_2$ | —C$_2$H$_5$ |
| 4-OCF$_3$ | —C(CH$_3$)$_3$ | —C$_2$H$_5$ | CH$_2$ | —C$_2$H$_5$ |
| 4-OCHF$_2$ | —C(CH$_3$)$_3$ | —C$_2$H$_5$ | CH$_2$ | —C$_2$H$_5$ |
| 4-OCH$_3$ | —C(CH$_3$)$_3$ | —C$_2$H$_5$ | CH$_2$ | —C$_2$H$_5$ |
| 4-Cl | —C(CH$_3$)$_2$CH$_2$F | —OC$_2$H$_5$ | CH$_2$ | —C$_2$H$_5$ |
| 4-Cl | —C(CH$_2$F)$_2$CH$_3$ | —OC$_2$H$_5$ | CH$_2$ | —C$_2$H$_5$ |
| 4-Cl | —C(CH$_3$)$_2$CH$_2$F | —C$_2$H$_5$ | CH$_2$ | —C$_2$H$_5$ |
| 4-Cl | —C(CH$_2$F)$_2$CH$_3$ | —C$_2$H$_5$ | CH$_2$ | —C$_2$H$_5$ |
| 4-Cl | —C(CH$_3$)$_3$ | —OC$_2$H$_5$ | O | —C$_2$H$_5$ |
| 4-Cl | —C(CH$_3$)$_3$ | —C$_2$H$_5$ | O | —C$_2$H$_5$ |
| 4-Cl | —C(CH$_3$)$_3$ | —NH—CH$_3$ | O | —C$_2$H$_5$ |

TABLE 9

(Ik)

[Structure: phenyl ring with $X^6_u$ substituents, connected via C(bonded to A in a ring with two O atoms) to CH₂-N of a thione-containing triazole ring bearing P(=S)(R¹)(OR²)]

| $X^6_u$ | A | $R^1$ | $R^{2'}$ |
|---|---|---|---|
| 2,4-Cl₂ | —(CH₂)₃— | —OC₂H₅ | —C₂H₅ |
| 2,4-Cl₂ | —(CH₂)₂— | —OC₂H₅ | —C₂H₅ |
| 4-Cl | —CH₂—CH(CH₃)— | —OC₂H₅ | —C₂H₅ |
| 4-CF₃ | —CH₂—CH(C₃H₇-n)— | —OC₂H₅ | —C₂H₅ |
| 2-Cl, 4-O-(4-Cl-C₆H₄) | —CH₂—CH₂— | —OC₂H₅ | —C₂H₅ |
| 2-Cl, 4-O-(4-Cl-C₆H₄) | —CH₂—CH(C₂H₅)— | —OC₂H₅ | —C₂H₅ |
| 4-F | —CH₂—CH(C₃H₇-n)— | —OC₂H₅ | —C₂H₅ |
| 4-OCF₃ | —CH₂—CH(C₃H₇-n)— | —OC₂H₅ | —C₂H₅ |
| 2,4-F₂ | —CH₂—CH(C₃H₇-n)— | —OC₂H₅ | —C₂H₅ |
| 2-OCHF₂ | —CH₂—CH(C₃H₇-n)— | —OC₂H₅ | —C₂H₅ |
| 2-Cl, 4-O-(4-Cl-C₆H₄) | —(CH₂)₃— | —OC₂H₅ | —C₂H₅ |
| 2,4,6-Cl₃ | —CH₂—CH(C₃H₇-n)— | —OC₂H₅ | —C₂H₅ |
| — | —CH₂—CH(C₃H₇-n)— | —OC₂H₅ | —C₂H₅ |
| 2,4-F₂ | —CH₂—CH(CH₃)— | —OC₂H₅ | —C₂H₅ |

TABLE 9-continued (Ik)

$$\text{X}^6_u-\text{C}_6\text{H}_{4-u}-\underset{\underset{A}{O}}{\overset{\overset{}{C}}{\underset{|}{C}}}-\text{CH}_2-\text{N}-\text{N}=\text{CH}-\text{N}-\overset{S}{\underset{OR^2}{P}}-R^1$$

| $X^6_u$ | A | $R^1$ | $R^{2'}$ |
|---|---|---|---|
| 2-Cl, 4-O—C$_6$H$_4$—Cl | —CH$_2$—CH(CH$_3$)— | —OC$_2$H$_5$ | —C$_2$H$_5$ |
| 2,4-Cl$_2$ | —CH(CH$_3$)—CH(CH$_3$)— | —OC$_2$H$_5$ | —C$_2$H$_5$ |
| 2-Cl, 4-O—C$_6$H$_4$—Cl | —CH(CH$_3$)—CH(CH$_3$)— | —OC$_2$H$_5$ | —C$_2$H$_5$ |
| 2,4-Cl$_2$ | —CH$_2$—CH(F)— | —OC$_2$H$_5$ | —C$_2$H$_5$ |
| 2-Cl, 4-O—C$_6$H$_4$—Cl | —CH$_2$—CH(C$_4$H$_9$-n)— | —OC$_2$H$_5$ | —C$_2$H$_5$ |
| 2,4-Cl$_2$ | —CH$_2$—CH(C$_2$H$_5$)— | —OC$_2$H$_5$ | —C$_2$H$_5$ |
| 2,4-Cl$_2$ | —(CH$_2$)$_3$— | —C$_2$H$_5$ | —C$_2$H$_5$ |
| 2,4-Cl$_2$ | —(CH$_2$)$_2$— | —C$_2$H$_5$ | —C$_2$H$_5$ |
| 4-Cl | —CH$_2$—CH(CH$_3$)— | —C$_2$H$_5$ | —C$_2$H$_5$ |
| 4-CF$_3$ | —CH$_2$—CH(C$_3$H$_7$-n)— | —C$_2$H$_5$ | —C$_2$H$_5$ |
| 2-Cl, 4-O—C$_6$H$_4$—Cl | —CH$_2$—CH$_2$— | —C$_2$H$_5$ | —C$_2$H$_5$ |
| 2-Cl, 4-O—C$_6$H$_4$—Cl | —CH$_2$—CH(C$_2$H$_5$)— | —C$_2$H$_5$ | —C$_2$H$_5$ |
| 4-F | —CH$_2$—CH(C$_3$H$_7$-n)— | —C$_2$H$_5$ | —C$_2$H$_5$ |
| 4-OCF$_3$ | —CH$_2$—CH(C$_3$H$_7$-n)— | —C$_2$H$_5$ | —C$_2$H$_5$ |

TABLE 9-continued (Ik)

[Structure of formula Ik showing phenyl ring with $X^6_u$ substituents, connected to a 1,3-dioxetane ring with A bridge, CH$_2$ linker to triazole-thione with P(=S)(R$^1$)(OR$^2$) group]

| $X^6_u$ | A | $R^1$ | $R^{2\prime}$ |
|---|---|---|---|
| 2,4-F$_2$ | —CH$_2$—CH(C$_3$H$_7$-n)— | —C$_2$H$_5$ | —C$_2$H$_5$ |
| 2-OCHF$_2$ | —CH$_2$—CH(C$_3$H$_7$-n)— | —C$_2$H$_5$ | —C$_2$H$_5$ |
| 2-Cl, 4-O—C$_6$H$_4$—Cl | —(CH$_2$)$_3$— | —C$_2$H$_5$ | —C$_2$H$_5$ |
| 2,4,6-Cl$_3$ | —CH$_2$—CH(C$_3$H$_7$-n)— | —C$_2$H$_5$ | —C$_2$H$_5$ |
| — | —CH$_2$—CH(C$_3$H$_7$-n)— | —C$_2$H$_5$ | —C$_2$H$_5$ |
| 2,4-F$_2$ | —CH$_2$—CH(CH$_3$)— | —C$_2$H$_5$ | —C$_2$H$_5$ |
| 2-Cl, 4-O—C$_6$H$_4$—Cl | —CH$_2$—CH(CH$_3$)— | —C$_2$H$_5$ | —C$_2$H$_5$ |
| 2,4-Cl$_2$ | —CH(CH$_3$)—CH(CH$_3$)— | —C$_2$H$_5$ | —C$_2$H$_5$ |
| 2-Cl, 4-O—C$_6$H$_4$—Cl | —CH(CH$_3$)—CH(CH$_3$)— | —C$_2$H$_5$ | —C$_2$H$_5$ |
| 2,4-Cl$_2$ | —CH$_2$—CH(F)— | —C$_2$H$_5$ | —C$_2$H$_5$ |
| 2-Cl, 4-O—C$_6$H$_4$—Cl | —CH$_2$—CH(C$_4$H$_9$-n)— | —C$_2$H$_5$ | —C$_2$H$_5$ |
| 2,4-Cl$_2$ | —CH$_2$—CH(C$_2$H$_5$)— | —C$_2$H$_5$ | —C$_2$H$_5$ |
| 2,4-Cl$_2$ | —CH$_2$—CH(C$_3$H$_7$-n)— | —OC$_2$H$_5$ | —C$_2$H$_5$ |

TABLE 9-continued (Ik)

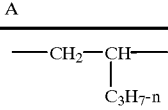

| X⁶ᵤ | A | R¹ | R²' |
|---|---|---|---|
| 2,4-Cl₂ | —CH₂—CH(C₃H₇-n)— | —C₂H₅ | —C₂H₅ |
| 2,4-Cl₂ | —CH₂—CH(C₃H₇-n)— | —NH—CH₃ | —C₂H₅ |

TABLE 10

(Im)

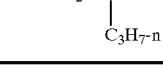

| X⁷ᵥ | R²¹ | R¹ | R²⁴⁰ |
|---|---|---|---|
| 2,4-Cl₂ | —CH₃ | —OC₂H₅ | —C₂H₅ |
| 2,4-Cl₂ | —C₂H₅ | —OC₂H₅ | —C₂H₅ |
| 2,4-Cl₂ | —CH(CH₃)₂ | —OC₂H₅ | —C₂H₅ |
| 4-Cl | —C₃H₇-n | —OC₂H₅ | —C₂H₅ |
| 2,4-Cl₂ | —C₄H₉-n | —OC₂H₅ | —C₂H₅ |
| 2,4-Cl₂ | —CH(CH₃)C₂H₅ | —OC₂H₅ | —C₂H₅ |
| 2,4-Cl₂ | —C(CH₃)₃ | —OC₂H₅ | —C₂H₅ |
| 2-Cl | —C₃H₇-n | —OC₂H₅ | —C₂H₅ |
| 2-OCF₃ | —C₃H₇-n | —OC₂H₅ | —C₂H₅ |
| 4-CF₃ | —C₃H₇-n | —OC₂H₅ | —C₂H₅ |
| 4-CH₃ | —C₃H₇-n | —OC₂H₅ | —C₂H₅ |
| 2,4,6-Cl₃ | —C₃H₇-n | —OC₂H₅ | —C₂H₅ |
| 2,4,Cl₂ |  | —OC₂H₅ | —C₂H₅ |
| 4-F | —C₃H₇-n | —OC₂H₅ | —C₂H₅ |
| 2,4-Cl₂ |  | —OC₂H₅ | —C₂H₅ |
| 2,4-Cl₂ | 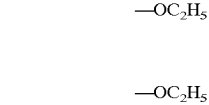 | —OC₂H₅ | —C₂H₅ |
| 2,4-Cl₂ |  | —OC₂H₅ | —C₂H₅ |

TABLE 10-continued (Im)

| X⁷ᵥ | R²¹ | R¹ | R²⁴⁰ |
|---|---|---|---|
| 2,4-Cl₂ |  | —OC₂H₅ | —C₂H₅ |
| 2,4-Cl₂ | 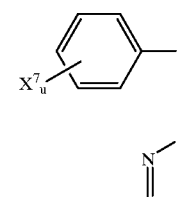 | —OC₂H₅ | —C₂H₅ |
| 2,4-Cl₂ | 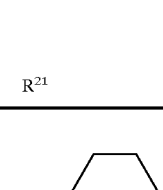 | —OC₂H₅ | —C₂H₅ |
| 2,4-Cl₂ | 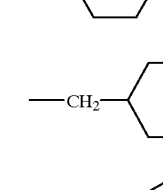 | —OC₂H₅ | —C₂H₅ |
| 2,4-Cl₂ | 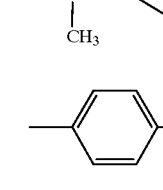 | —OC₂H₅ | —C₂H₅ |
| 2,4-Cl₂ | 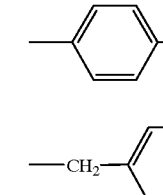 | —OC₂H₅ | —C₂H₅ |

TABLE 10-continued (Im)

| $X^7_v$ | $R^{21}$ | $R^1$ | $R^{240}$ |
|---|---|---|---|
| 2,4-Cl$_2$ | —CH$_2$—C$_6$H$_4$—F (4-F) | —OC$_2$H$_5$ | —C$_2$H$_5$ |
| 2,4-Cl$_2$ | —CH$_2$—O—CF$_2$—CHF$_2$ | —OC$_2$H$_5$ | —C$_2$H$_5$ |
| 2,4-Cl$_2$ | —CH$_2$—O—CF$_2$—CH$_3$ | —OC$_2$H$_5$ | —C$_2$H$_5$ |
| 4-Cl | —CH$_2$—O—CF$_2$—CHF$_2$ | —OC$_2$H$_5$ | —C$_2$H$_5$ |
| 2,4-Cl$_2$ | —CH$_2$—O—CF$_3$ | —OC$_2$H$_5$ | —C$_2$H$_5$ |
| 4-F | —CH$_2$—O—CF$_2$—CHF$_2$ | —OC$_2$H$_5$ | —C$_2$H$_5$ |
| 2-Cl | —CH$_2$—O—CF$_2$—CHF$_2$ | —OC$_2$H$_5$ | —C$_2$H$_5$ |
| 2,4-Cl$_2$ | —CH$_3$ | —C$_2$H$_5$ | —C$_2$H$_5$ |
| 2,4-Cl$_2$ | —C$_2$H$_5$ | —C$_2$H$_5$ | —C$_2$H$_5$ |
| 2,4-Cl$_2$ | —CH(CH$_3$)$_2$ | —C$_2$H$_5$ | —C$_2$H$_5$ |
| 4-Cl | —C$_3$H$_7$-n | —C$_2$H$_5$ | —C$_2$H$_5$ |
| 2,4-Cl$_2$ | —C$_4$H$_9$-n | —C$_2$H$_5$ | —C$_2$H$_5$ |
| 2,4-Cl$_2$ | —CH(CH$_3$)—C$_2$H$_5$ | —C$_2$H$_5$ | —C$_2$H$_5$ |
| 2,4-Cl$_2$ | —C(CH$_3$)$_3$ | —C$_2$H$_5$ | —C$_2$H$_5$ |
| 2-Cl | —C$_3$H$_7$-n | —C$_2$H$_5$ | —C$_2$H$_5$ |
| 2-OCF$_3$ | —C$_3$H$_7$-n | —C$_2$H$_5$ | —C$_2$H$_5$ |
| 4-CF$_3$ | —C$_3$H$_7$-n | —C$_2$H$_5$ | —C$_2$H$_5$ |
| 4-CH$_3$ | —C$_3$H$_7$-n | —C$_2$H$_5$ | —C$_2$H$_5$ |
| 2,4,6-Cl$_3$ | —C$_3$H$_7$-n | —C$_2$H$_5$ | —C$_2$H$_5$ |
| 2,4-Cl$_2$ | chlorocyclopropyl | —C$_2$H$_5$ | —C$_2$H$_5$ |
| 4-F | —C$_3$H$_7$-n | —C$_2$H$_5$ | —C$_2$H$_5$ |
| 2,4-Cl$_2$ | fluorocyclopropyl | —C$_2$H$_5$ | —C$_2$H$_5$ |
| 2,4-Cl$_2$ | cyclopropyl | —C$_2$H$_5$ | —C$_2$H$_5$ |
| 2,4-Cl$_2$ | cyclopentyl | —C$_2$H$_5$ | —C$_2$H$_5$ |
| 2,4-Cl$_2$ | cyclohexyl | —C$_2$H$_5$ | —C$_2$H$_5$ |
| 2,4-Cl$_2$ | —CH$_2$-cyclohexyl | —C$_2$H$_5$ | —C$_2$H$_5$ |
| 2,4-Cl$_2$ | —CH(CH$_3$)-cyclopropyl | —C$_2$H$_5$ | —C$_2$H$_5$ |

TABLE 10-continued (Im)

| $X^7_v$ | $R^{21}$ | $R^1$ | $R^{240}$ |
|---|---|---|---|
| 2,4-Cl$_2$ | 4-Cl-C$_6$H$_4$— | —C$_2$H$_5$ | —C$_2$H$_5$ |
| 2,4-Cl$_2$ | 4-F-C$_6$H$_4$— | —C$_2$H$_5$ | —C$_2$H$_5$ |
| 2,4-Cl$_2$ | —CH$_2$—C$_6$H$_4$-4-Cl | —C$_2$H$_5$ | —C$_2$H$_5$ |
| 2,4-Cl$_2$ | —CH$_2$—C$_6$H$_4$-4-F | —C$_2$H$_5$ | —C$_2$H$_5$ |
| 2,4-Cl$_2$ | —CH$_2$—O—CF$_2$—CHF$_2$ | —C$_2$H$_5$ | —C$_2$H$_5$ |
| 2,4-Cl$_2$ | —CH$_2$—O—CF$_2$—CH$_3$ | —C$_2$H$_5$ | —C$_2$H$_5$ |
| 4-Cl | —CH$_2$—O—CF$_2$—CHF$_2$ | —C$_2$H$_5$ | —C$_2$H$_5$ |
| 2,4-Cl$_2$ | —CH$_2$—O—CF$_3$ | —C$_2$H$_5$ | —C$_2$H$_5$ |
| 4-F | —CH$_2$—O—CF$_2$—CHF$_2$ | —C$_2$H$_5$ | —C$_2$H$_5$ |
| 2-Cl | —CH$_2$—O—CF$_2$—CHF$_2$ | —C$_2$H$_5$ | —C$_2$H$_5$ |
| 2,4-Cl$_2$ | —CH$_2$—CF$_3$ | —OC$_2$H$_5$ | —C$_2$H$_5$ |
| 2,4-Cl$_2$ | —CH$_2$—CF$_3$ | —OC$_2$H$_5$ | —C$_2$H$_5$ |
| 2,4-Cl$_2$ | —C$_3$H$_7$-n | —OC$_2$H$_5$ | —C$_2$H$_5$ |
| 2,4-Cl$_2$ | —C$_3$H$_7$-n | —C$_2$H$_5$ | —C$_2$H$_5$ |
| 2,4-Cl$_2$ | —C$_3$H$_7$-n | —NH—CH$_3$ | —C$_2$H$_5$ |

TABLE 11

(In)

| $X^8_w$ | $R^{22}$ | $R^1$ | $Y^4$ | $R^{2'}$ |
|---|---|---|---|---|
| 2,4-Cl$_2$ | C$_6$H$_5$— | —OC$_2$H$_5$ | O | —C$_2$H$_5$ |

TABLE 11-continued (In)

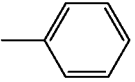

| $X^8_w$ | $R^{22}$ | $R^1$ | $Y^4$ | $R^{2'}$ |
|---|---|---|---|---|
| 4-Cl | 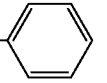 | —OC₂H₅ | O | —C₂H₅ |
| 4-Br | —C(CH₃)₃ | —OC₂H₅ | O | —C₂H₅ |
| — | —C(CH₃)₃ | —OC₂H₅ | O | —C₂H₅ |
| 4-C(CH₃)₃ | —C(CH₃)₃ | —OC₂H₅ | O | —C₂H₅ |
| 2-Cl | —C(CH₃)₃ | —OC₂H₅ | O | —C₂H₅ |
| 3-Cl | —C(CH₃)₃ | —OC₂H₅ | O | —C₂H₅ |
| 4-F | —C(CH₃)₃ | —OC₂H₅ | O | —C₂H₅ |
| 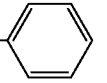 | —C(CH₃)₃ | —OC₂H₅ | O | —C₂H₅ |
| 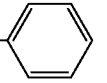 | —C(CH₃)₃ | —OC₂H₅ | O | —C₂H₅ |
| 2,4-Cl₂ | —C(CH₃)₃ | —OC₂H₅ | O | —C₂H₅ |
| 2-CH₃, 4-Cl | —C(CH₃)₃ | —OC₂H₅ | O | —C₂H₅ |
| 3,4-(CH₃)₂ | —C(CH₃)₃ | —OC₂H₅ | O | —C₂H₅ |
| 2,4,5-Cl₃ | —C(CH₃)₃ | —OC₂H₅ | O | —C₂H₅ |
| 4-Cl | —CH₃ | —OC₂H₅ | O | —C₂H₅ |
| 4-Cl | 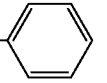 | —OC₂H₅ | O | —C₂H₅ |
| 4-CF₃ | —C(CH₃)₃ | —OC₂H₅ | O | —C₂H₅ |
| 4-OCF₃ | —C(CH₃)₃ | —OC₂H₅ | O | —C₂H₅ |
| 2-OCHF₂ | —C(CH₃)₃ | —OC₂H₅ | O | —C₂H₅ |
| 4-OCH₃ | —C(CH₃)₃ | —OC₂H₅ | O | —C₂H₅ |
| 2,4-Cl₂ | 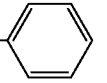 | —C₂H₅ | O | —C₂H₅ |
| 4-Cl | 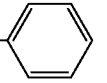 | —C₂H₅ | O | —C₂H₅ |
| 4-Br | —C(CH₃)₃ | —C₂H₅ | O | —C₂H₅ |
| — | —C(CH₃)₃ | —C₂H₅ | O | —C₂H₅ |
| 4-C(CH₃)₃ | —C(CH₃)₃ | —C₂H₅ | O | —C₂H₅ |
| 2-Cl | —C(CH₃)₃ | —C₂H₅ | O | —C₂H₅ |
| 3-Cl | —C(CH₃)₃ | —C₂H₅ | O | —C₂H₅ |
| 4-F | —C(CH₃)₃ | —C₂H₅ | O | —C₂H₅ |
| 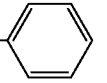 | —C(CH₃)₃ | —C₂H₅ | O | —C₂H₅ |

TABLE 11-continued (In)

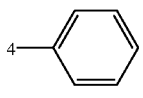

| $X^8_w$ | $R^{22}$ | $R^1$ | $Y^4$ | $R^{2'}$ |
|---|---|---|---|---|
| 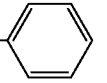 | —C(CH₃)₃ | —C₂H₅ | O | —C₂H₅ |
| 2,4-Cl₂ | —C(CH₃)₃ | —C₂H₅ | O | —C₂H₅ |
| 2-CH₃, 4-Cl | —C(CH₃)₃ | —C₂H₅ | O | —C₂H₅ |
| 3,4-(CH₃)₂ | —C(CH₃)₃ | —C₂H₅ | O | —C₂H₅ |
| 2,4,5-Cl₃ | —C(CH₃)₃ | —C₂H₅ | O | —C₂H₅ |
| 4-Cl | —CH₃ | —C₂H₅ | O | —C₂H₅ |
| 4-Cl | 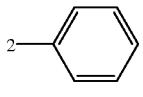 | —C₂H₅ | O | —C₂H₅ |
| 4-CF₃ | —C(CH₃)₃ | —C₂H₅ | O | —C₂H₅ |
| 4-OCF₃ | —C(CH₃)₃ | —C₂H₅ | O | —C₂H₅ |
| 2-OCHF₂ | —C(CH₃)₃ | —C₂H₅ | O | —C₂H₅ |
| 4-OCH₃ | —C(CH₃)₃ | —C₂H₅ | O | —C₂H₅ |
| 4-Cl | 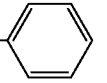 | —OC₂H₅ | O | —C₂H₅ |
| 4-Cl | 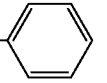 | —OC₂H₅ | O | —C₂H₅ |
| 4-Cl | 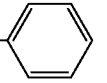 | —C₂H₅ | O | —C₂H₅ |
| 4-Cl | 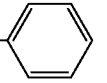 | —C₂H₅ | O | —C₂H₅ |
| 2,4-Cl₂ | 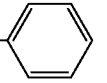 | —OC₂H₅ | CH₂ | —C₂H₅ |
| 4-Cl | 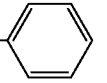 | —OC₂H₅ | CH₂ | —C₂H₅ |
| 4-Br | —C(CH₃)₃ | —OC₂H₅ | CH₂ | —C₂H₅ |
| — | —C(CH₃)₃ | —OC₂H₅ | CH₂ | —C₂H₅ |
| 4-C(CH₃)₃ | —C(CH₃)₃ | —OC₂H₅ | CH₂ | —C₂H₅ |
| 2-Cl | —C(CH₃)₃ | —OC₂H₅ | CH₂ | —C₂H₅ |
| 3-Cl | —C(CH₃)₃ | —OC₂H₅ | CH₂ | —C₂H₅ |

TABLE 11-continued (In)

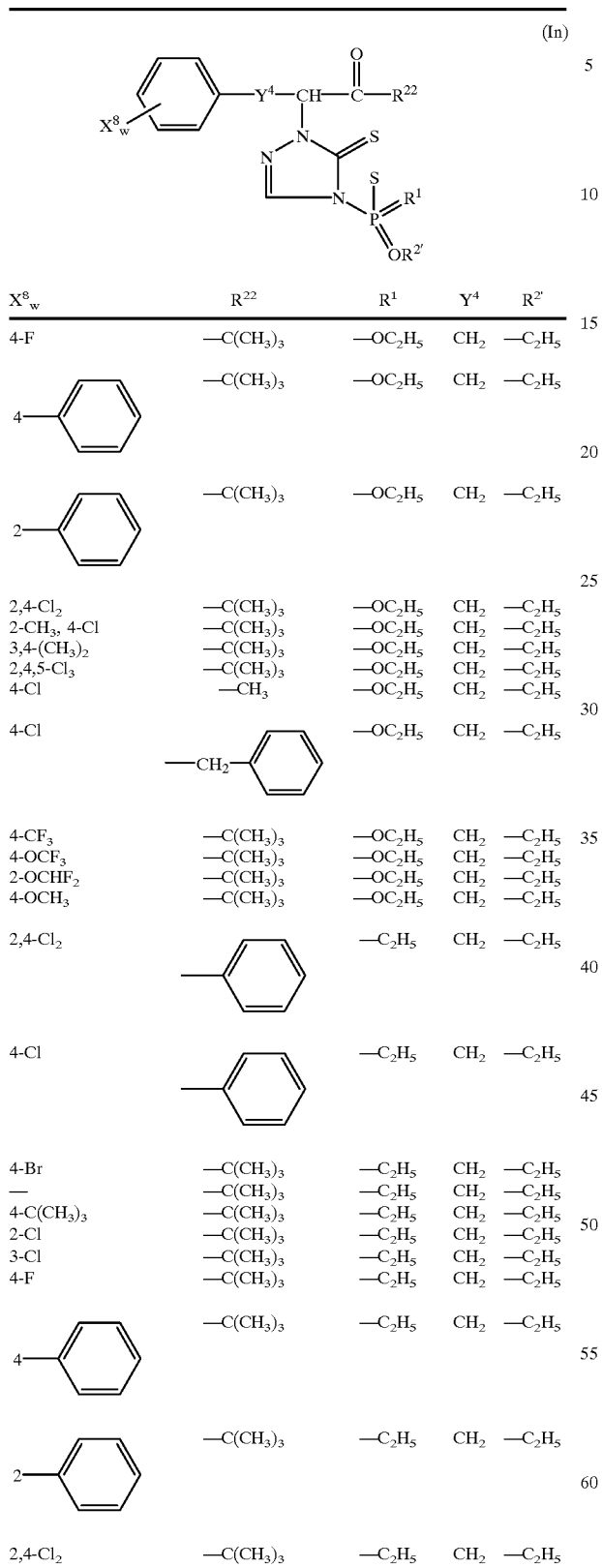

| $X^8_w$ | $R^{22}$ | $R^1$ | $Y^4$ | $R^{2'}$ |
|---|---|---|---|---|
| 4-F | —C(CH$_3$)$_3$ | —OC$_2$H$_5$ | CH$_2$ | —C$_2$H$_5$ |
| 4-phenyl | —C(CH$_3$)$_3$ | —OC$_2$H$_5$ | CH$_2$ | —C$_2$H$_5$ |
| 2-phenyl | —C(CH$_3$)$_3$ | —OC$_2$H$_5$ | CH$_2$ | —C$_2$H$_5$ |
| 2,4-Cl$_2$ | —C(CH$_3$)$_3$ | —OC$_2$H$_5$ | CH$_2$ | —C$_2$H$_5$ |
| 2-CH$_3$, 4-Cl | —C(CH$_3$)$_3$ | —OC$_2$H$_5$ | CH$_2$ | —C$_2$H$_5$ |
| 3,4-(CH$_3$)$_2$ | —C(CH$_3$)$_3$ | —OC$_2$H$_5$ | CH$_2$ | —C$_2$H$_5$ |
| 2,4,5-Cl$_3$ | —C(CH$_3$)$_3$ | —OC$_2$H$_5$ | CH$_2$ | —C$_2$H$_5$ |
| 4-Cl | —CH$_3$ | —OC$_2$H$_5$ | CH$_2$ | —C$_2$H$_5$ |
| 4-Cl | —CH$_2$-phenyl | —OC$_2$H$_5$ | CH$_2$ | —C$_2$H$_5$ |
| 4-CF$_3$ | —C(CH$_3$)$_3$ | —OC$_2$H$_5$ | CH$_2$ | —C$_2$H$_5$ |
| 4-OCF$_3$ | —C(CH$_3$)$_3$ | —OC$_2$H$_5$ | CH$_2$ | —C$_2$H$_5$ |
| 2-OCHF$_2$ | —C(CH$_3$)$_3$ | —OC$_2$H$_5$ | CH$_2$ | —C$_2$H$_5$ |
| 4-OCH$_3$ | —C(CH$_3$)$_3$ | —OC$_2$H$_5$ | CH$_2$ | —C$_2$H$_5$ |
| 2,4-Cl$_2$ | 4-methylphenyl | —OC$_2$H$_5$ | CH$_2$ | —C$_2$H$_5$ |
| 4-Cl | 4-methylphenyl | —OC$_2$H$_5$ | CH$_2$ | —C$_2$H$_5$ |
| 4-Br | —C(CH$_3$)$_3$ | —C$_2$H$_5$ | CH$_2$ | —C$_2$H$_5$ |
| — | —C(CH$_3$)$_3$ | —C$_2$H$_5$ | CH$_2$ | —C$_2$H$_5$ |
| 4-C(CH$_3$)$_3$ | —C(CH$_3$)$_3$ | —C$_2$H$_5$ | CH$_2$ | —C$_2$H$_5$ |
| 2-Cl | —C(CH$_3$)$_3$ | —C$_2$H$_5$ | CH$_2$ | —C$_2$H$_5$ |
| 3-Cl | —C(CH$_3$)$_3$ | —C$_2$H$_5$ | CH$_2$ | —C$_2$H$_5$ |
| 4-F | —C(CH$_3$)$_3$ | —C$_2$H$_5$ | CH$_2$ | —C$_2$H$_5$ |
| 4-phenyl | —C(CH$_3$)$_3$ | —C$_2$H$_5$ | CH$_2$ | —C$_2$H$_5$ |
| 2-phenyl | —C(CH$_3$)$_3$ | —C$_2$H$_5$ | CH$_2$ | —C$_2$H$_5$ |
| 2,4-Cl$_2$ | —C(CH$_3$)$_3$ | —C$_2$H$_5$ | CH$_2$ | —C$_2$H$_5$ |

(In)

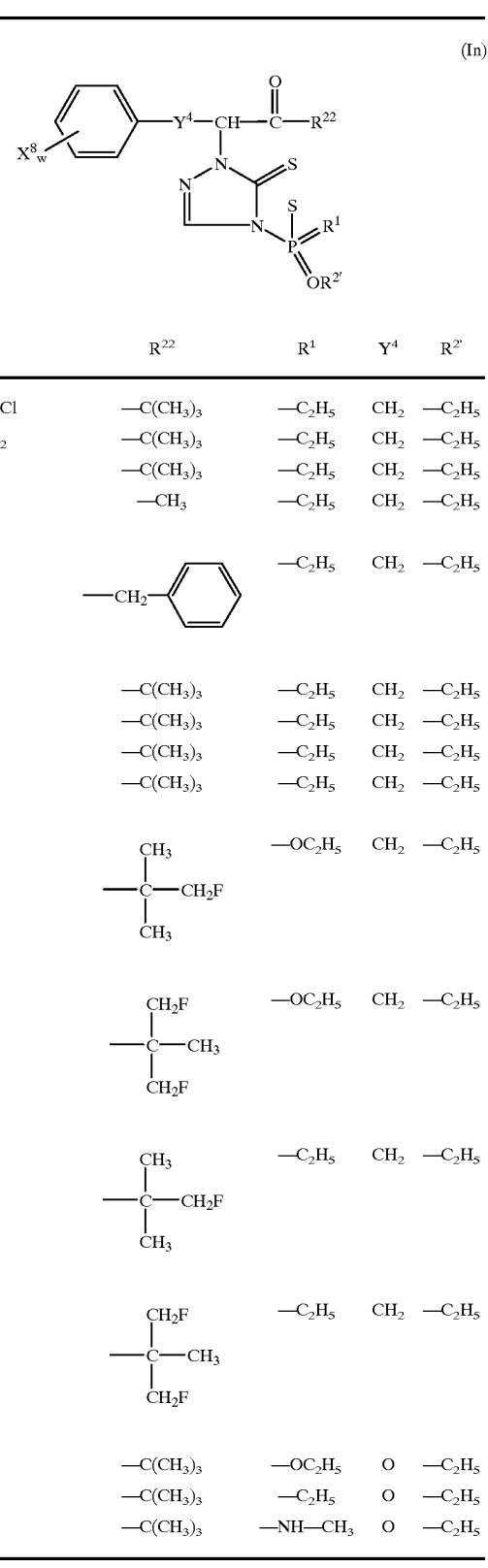

| $X^8_w$ | $R^{22}$ | $R^1$ | $Y^4$ | $R^{2'}$ |
|---|---|---|---|---|
| 2-CH$_3$, 4-Cl | —C(CH$_3$)$_3$ | —C$_2$H$_5$ | CH$_2$ | —C$_2$H$_5$ |
| 3,4-(CH$_3$)$_2$ | —C(CH$_3$)$_3$ | —C$_2$H$_5$ | CH$_2$ | —C$_2$H$_5$ |
| 2,4,5-Cl$_3$ | —C(CH$_3$)$_3$ | —C$_2$H$_5$ | CH$_2$ | —C$_2$H$_5$ |
| 4-Cl | —CH$_3$ | —C$_2$H$_5$ | CH$_2$ | —C$_2$H$_5$ |
| 4-Cl | —CH$_2$-phenyl | —C$_2$H$_5$ | CH$_2$ | —C$_2$H$_5$ |
| 4-CF$_3$ | —C(CH$_3$)$_3$ | —C$_2$H$_5$ | CH$_2$ | —C$_2$H$_5$ |
| 4-OCF$_3$ | —C(CH$_3$)$_3$ | —C$_2$H$_5$ | CH$_2$ | —C$_2$H$_5$ |
| 2-OCHF$_2$ | —C(CH$_3$)$_3$ | —C$_2$H$_5$ | CH$_2$ | —C$_2$H$_5$ |
| 4-OCH$_3$ | —C(CH$_3$)$_3$ | —C$_2$H$_5$ | CH$_2$ | —C$_2$H$_5$ |
| 4-Cl | —C(CH$_3$)$_2$CH$_2$F | —OC$_2$H$_5$ | CH$_2$ | —C$_2$H$_5$ |
| 4-Cl | —C(CH$_3$)(CH$_2$F)$_2$ | —OC$_2$H$_5$ | CH$_2$ | —C$_2$H$_5$ |
| 4-Cl | —C(CH$_3$)$_2$CH$_2$F | —C$_2$H$_5$ | CH$_2$ | —C$_2$H$_5$ |
| 4-Cl | —C(CH$_3$)(CH$_2$F)$_2$ | —C$_2$H$_5$ | CH$_2$ | —C$_2$H$_5$ |
| 4-Cl | —C(CH$_3$)$_3$ | —OC$_2$H$_5$ | O | —C$_2$H$_5$ |
| 4-Cl | —C(CH$_3$)$_3$ | —C$_2$H$_5$ | O | —C$_2$H$_5$ |
| 4-Cl | —C(CH$_3$)$_3$ | —NH—CH$_3$ | O | —C$_2$H$_5$ |

TABLE 12

(Ip)

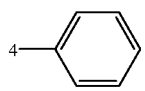

| $X^9{}_z$ | $R^{23}$ | $R^1$ | $R^{2'}$ |
|---|---|---|---|
| 4-Cl | —C$_4$H$_9$-n | —OC$_2$H$_5$ | —C$_2$H$_5$ |
| 2-Cl | —C$_4$H$_9$-n | —OC$_2$H$_5$ | —C$_2$H$_5$ |
| 2,4-Cl$_2$ | —C$_4$H$_9$-n | —OC$_2$H$_5$ | —C$_2$H$_5$ |
| 4-Br | —C$_4$H$_9$-n | —OC$_2$H$_5$ | —C$_2$H$_5$ |
| 4-F | —C$_4$H$_9$-n | —OC$_2$H$_5$ | —C$_2$H$_5$ |
| 4-C(CH$_3$)$_3$ | —C$_4$H$_9$-n | —OC$_2$H$_5$ | —C$_2$H$_5$ |
| 4-C$_6$H$_5$ | —C$_4$H$_9$-n | —OC$_2$H$_5$ | —C$_2$H$_5$ |
| 4-Cl | —C(CH$_3$)$_3$ | —OC$_2$H$_5$ | —C$_2$H$_5$ |
| 2-Cl | —C(CH$_3$)$_3$ | —OC$_2$H$_5$ | —C$_2$H$_5$ |
| 2,4-Cl$_2$ | —C(CH$_3$)$_3$ | —OC$_2$H$_5$ | —C$_2$H$_5$ |
| 2,4,6-Cl$_3$ | —C(CH$_3$)$_3$ | —OC$_2$H$_5$ | —C$_2$H$_5$ |
| 4-CF$_3$ | —C(CH$_3$)$_3$ | —OC$_2$H$_5$ | —C$_2$H$_5$ |
| 2-OCHF$_2$ | —C(CH$_3$)$_3$ | —OC$_2$H$_5$ | —C$_2$H$_5$ |
| 4-Cl | —C(CH$_3$)$_2$CH$_2$F | —OC$_2$H$_5$ | —C$_2$H$_5$ |
| 4-Cl | —C(CH$_3$)(CH$_2$F)$_2$ | —OC$_2$H$_5$ | —C$_2$H$_5$ |
| 4-Cl | —CH$_2$-C$_6$H$_4$-4-Cl | —OC$_2$H$_5$ | —C$_2$H$_5$ |
| 4-Cl | —CH(CH$_3$)-C$_6$H$_4$-4-Cl | —OC$_2$H$_5$ | —C$_2$H$_5$ |
| 4-Cl | —C$_6$H$_4$-4-Cl | —OC$_2$H$_5$ | —C$_2$H$_5$ |
| 4-Cl | —CH$_2$—CH$_2$-C$_6$H$_4$-4-Cl | —OC$_2$H$_5$ | —C$_2$H$_5$ |
| — | —CH$_2$—CH$_2$-C$_6$H$_4$-4-F | —OC$_2$H$_5$ | —C$_2$H$_5$ |
| 4-Cl | —C$_4$H$_9$-n | —C$_2$H$_5$ | —C$_2$H$_5$ |

TABLE 12-continued

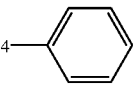
(Ip)

| X⁹_z | R²³ | R¹ | R²' |
|---|---|---|---|
| 2-Cl | —C₄H₉-n | —C₂H₅ | —C₂H₅ |
| 2,4-Cl₂ | —C₄H₉-n | —C₂H₅ | —C₂H₅ |
| 4-Br | —C₄H₉-n | —C₂H₅ | —C₂H₅ |
| 4-F | —C₄H₉-n | —C₂H₅ | —C₂H₅ |
| 4-C(CH₃)₃ | —C₄H₉-n | —C₂H₅ | —C₂H₅ |
| 4-C₆H₅ | —C₄H₉-n | —C₂H₅ | —C₂H₅ |
| 4-Cl | —C(CH₃)₃ | —C₂H₅ | —C₂H₅ |
| 2-Cl | —C(CH₃)₃ | —C₂H₅ | —C₂H₅ |
| 2,4-Cl₂ | —C(CH₃)₃ | —C₂H₅ | —C₂H₅ |
| 2,4,6-Cl₃ | —C(CH₃)₃ | —C₂H₅ | —C₂H₅ |
| 4-CF₃ | —C(CH₃)₃ | —C₂H₅ | —C₂H₅ |
| 2-OCHF₂ | —C(CH₃)₃ | —C₂H₅ | —C₂H₅ |
| 4-Cl | —C(CH₃)₂CH₂F | —C₂H₅ | —C₂H₅ |
| 4-Cl | —C(CH₃)(CH₂F)₂ | —C₂H₅ | —C₂H₅ |
| 4-Cl | —CH₂-C₆H₄-4-Cl | —C₂H₅ | —C₂H₅ |
| 4-Cl | —CH(CH₃)-C₆H₄-4-Cl | —C₂H₅ | —C₂H₅ |
| 4-Cl | —C₆H₄-4-Cl | —C₂H₅ | —C₂H₅ |
| 4-Cl | —CH₂CH₂-C₆H₄-4-Cl | —C₂H₅ | —C₂H₅ |
| — | —CH₂CH₂-C₆H₄-4-Cl | —C₂H₅ | —C₂H₅ |

TABLE 12-continued

(Ip)

| X$^9_z$ | R$^{23}$ | R$^1$ | R$^{2'}$ |
|---|---|---|---|
| — | —CH$_2$—CH$_2$—C$_6$H$_4$—F | —C$_2$H$_5$ | —C$_2$H$_5$ |
| — | —CH$_2$—CH$_2$—C$_6$H$_4$—Cl | —OC$_2$H$_5$ | —C$_2$H$_5$ |
| — | —CH$_2$—CH$_2$—C$_6$H$_4$—Cl | —NH—CH$_3$ | —C$_2$H$_5$ |

Using 2-(1-chloro-cyclopropyl)-1-(2-chlorophenyl)-3-(4,5-dihydro-5-thiono-1,2,4-triazol-1-yl)-propan-2-ol and diethyl chloro-thiophosphate as starting materials, the course of the process according to the invention can be illustrated by the formula scheme below.

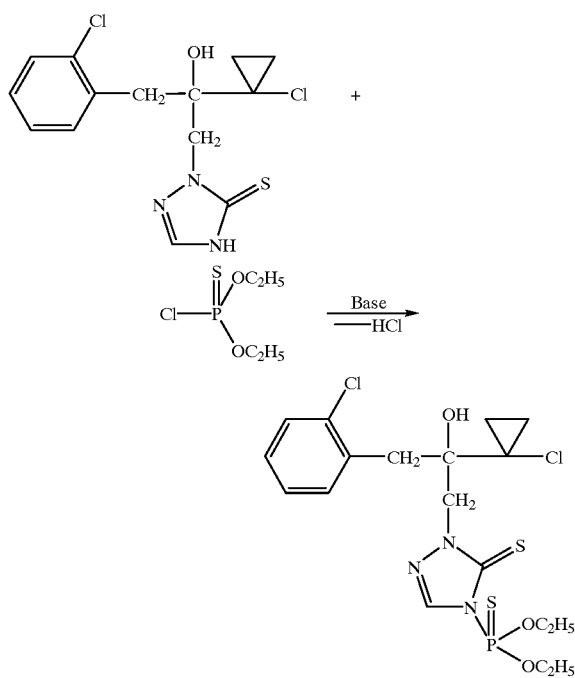

The formula (II) provides a general definition of the triazolinethiones required as starting materials for carrying out the process according to the invention. In this formula, R$^3$ preferably has those meanings which have already been mentioned in connection with the description of the substances of the formula (I) according to the invention as being preferred for this radical.

The triazolinethiones of the formula (II) are known or can be prepared by known methods (cf. WO 96-16 048, DE-A-195 20 097, DE-A-195 20 098, DE-A-195 20 096, DE-A-195 20 095, DE-A-195 20 597, DE-A-195 20 593, DE-A-195 21 030, DE-A-195 21 487, DE-A-195 28 300, DE-A-195 29 091 and DE-A-195 29 089).

The formula (III) provides a general definition of the phosphoric acid derivatives required as reaction components for carrying out the process according to the invention. In this formula, R$^1$, R$^2$ and Q each preferably have those meanings which have already been mentioned in connection with the description of the substances of the formula (I) according to the invention as bring preferred for these radicals.

The phosphoric acid derivatives of the formula (III) are known or can be prepared by known methods.

Suitable acid binders for carrying out the process according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicycloctane, (DABCO), diazabicyclononene (DBN) or diazabicycloundecene (DBU).

Suitable diluents for carrying out the process according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decaline; halogenated hydrocarbons; such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone, nitriles, such as acetonitrile, propionitrile, n- or i-butyronitrile or benzonitrile; esters, such as methyl acetate or ethyl acetate.

When carrying out the process according to the invention, the reaction temperatures can be varied within a certain range. In general, the process is carried out at temperatures between −20° C. and +40° C. preferably between −10° C. and +30° C.

The process according to the invention is generally carried out under atmospheric pressure. However, it is also possible to operate under elevated or reduced pressure.

The process according to the invention can also be carried out under an atmosphere of protective gas. Preferred protective gases are nitrogen and argon.

When carrying out the process according to the invention, generally 1 to 3 mol of phosphoric acid derivative of the formula (III) and an equivalent amount or else an excess of acid binder are employed per mole of triazolinethione of the formula (II). Work-up is carried out by customary methods. In general, the reaction mixture is concentrated, the residue is mixed with water, the resulting mixture is extracted with an organic solvent which is sparingly miscible with water and the combined organic phases are dried and concentrated. The resulting product can, if appropriate, be freed of any impurities which are still present using customary methods, for example recrystallization or chromatography.

The triazolinethione-phosphoric acid derivatives of the formula (I) obtainable by the process according to the invention can be converted into metal salt complexes.

Suitable salts for the preparation of metal salt complexes of the compounds of the formula (I) are preferably those of metals which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtering off, and, if appropriate, purified by recrystallization.

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Asomycetes, Basidiomycetes and Deuteromycetes.

Bactericides are employed in crop protection for controlling Pseudomonadacene, Rhizobiaceae, Enterobacteriaceae, Corynebacteriaceae and Streptomycetaceae, Some pathogens causing fungal and bacterial diseases which come under the generic names listed above are mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysidphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form; Drechslera, syn: Helminthosporium);
Cochliobolus species, such as, for example, *Cochiobolus sativus* (conidia form; Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum;*
Tilletia species, such as, for example, *Tilletia caries;*
Ustilago species, such as, for example, *Ustilago nuda* or *Ustilago avenae;*
Pelicularia species, such as, for example, *Pellicularia sasakii;*
Pyricularia species, such as, for example, *Pyricularia oryzae;*
Fusarium species, such as, for example, *Fusarium culmorum;*
Botyrtis species, such as, for example, *Botrytis cinerea;*
Septoria species, such as, for example, *Septoria nodorum;*
Leptosphaeria species, such as, for example, *Leptosphaertia nodorum;*
Cercospora species, such as, for example, *Cercospora canescens;*
Alternaria species, such as, for example, *Alternaria brassicae;* and
Pseudocerosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed in particular for controlling *Pyricularia oryzae* in rice and for controlling cereal diseases, such as Puccinia, Erysiphe and Fusarium species. Furthermore, the compounds according to the invention can be used very successfully against Venturia, Podosphaera and Sphaerotheca. They also have very good in vitro action.

Furthermore, the active compounds according to the invention may also be employed to increase the yield of crops. They are also of low toxicity and are well tolerated by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which maybe impaired by the proliferation of microorganisms, may also be mentioned within the scope of the materials to be protected. Industrial materials which may be mentioned within the scope of the present invention are preferably adhesives, sizes, paper and board, leather, wood, paints, cooling lubricants and heat-transfer liquids.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis,*
Arpergillus, such as *Aspergillus niger,*
Chaetomium, such as *Chaetomium globosum,*
Coniophora, such as *Coniophora puetana,*
Lentinus, such as *Lentinus tgrinus,*
Penicillium, such as *Penicillium glaucum,*
Polyporus, such as *Polyporus versicolor,*
Aurebasidium, such as *Aureobasidium pullulans,*
Sclerophoma, such as *Sclerophoma pityophila,*
Trichloderma, such as *Trichoderma viride,*
Escherichia, such as *Escherichia coli,*
Pseudomonas, such as *Pseudomonas aeruginosa,* and
Staphylococcus, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compounds for seeds, and ULV cool and warm fogging formulations.

These formulations are produced in a known manner, for example by mixing the active compounds with extenders, that is liquid solvents, liquefied gases, under pressure and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water.

Liquefied gaseous extenders or carriers are to be understood as meaning liquids which are gaseous at standard temperature and under atmospheric pressure, for example, aerosol propellants such as halogenated hydrocarbons, or else butane, propane, nitrogen and carbon dioxide. Suitable solid carriers are, for example, ground natural mineral such as kaolins, clays, talc, chalk, quartz, attapulgite, montmorillonite or diatomaceous earth, and ground synthetic minerals such as highly disperse silica, alumina and silicates. Suitable solid carriers for granules are, for example, crushed and fractionated natural rocks such as calcite, marble, pumice, sepiolite and dolomite, or else synthetic granules of inorganic and organic meals, and granules or organic material such as sawdust, coconut shells, maize cobs and tobacco stalks. Suitable emulsifiers and/or foam formers are, for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are, for example, lignin-sulphite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations, also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos, ampropylfos potassium, andoprim, anilazine, azacoazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofuluanid, dichlomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene(PCNB), sulphur and sulphur preparations, tebuconazole, tecloftalam, tecnazene, tetcyclasis, tetraconazole, thiabendazole, thicyofen, thiflurazmides, thiophanate-methyl, thiram, tioxymid, tolclofos-methyl, tolylfuanid, triadimefon, triadimenol, triazbutil, triazoxide, trichlamide, tricycloazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1-H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)suphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d] pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol(OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4,5]decane-2-methanamine, 8-hydroxyquinoline sulphate, 2H-xanthene-2-[(phenylamino)-carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydochloride, ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimideamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanemidamie,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
bromopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.
Insecticides/Acaricides/Nematicides:
abamectin, acephate, acrinathrin, alanycarb, aldicarb, alphamethrin, amitraz, avermectin, AZ60541, azadirachtin, azinphos A, azinphos M, azocyclotin,
Bacillus thuringiensis, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamides, chlorpyrifos, chlorpyrifos M, cis-resmethrin, clocythrin, clofentezine, cyanophos, cyprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethosprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluzinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, opxydeprofos,
parathion A, parathion M, permethrin, phenthoate, phorate, phosalone, phosmet, phosphamidon, phoxim, pirimicarb, pirimiphos M, pirimiphos A. profenophos, promecarb, propaphos, propoxur, prothiofos, prothoate, pymetrozin, pyrachlophos, pyridaphenethion, pyresmethrin, pyrethrum, pyridaben, pyrimidifen, pyriproxifen,
quinalphos,
salithion, sebufos, silafluofen, sulfotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth-promoting substances.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compound are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The compositions used for protecting industrial materials generally comprise an amount of 1 to 95% by weight, preferably 10 to 75% by weight, of the active compounds.

The use concentrations of the active compounds according to the invention depend on the species and the occurrence of the microorganisms to be controlled and on the composition of the material to be protected. The optimum rate of application can be determined by test series. In general, the use concentrations are in the range from 0.001 to 5% by weight, preferably from 0.05 to 1.0% by weight, based on the material to be protected.

The activity and the activity spectrum of the active compounds to be used according to the invention in the protection of materials and of the compositions, concentrates or quite generally formulations preparable from them can be increased by adding, if appropriate, other antimicrobially active compounds, fungicides, bactericides, herbicides, insecticides or other active compounds for increasing the activity spectrum or achieving particular effects, such as, for example, additional protection against insects. These mixtures may have a broader activity spectrum than the compounds according to the invention.

The preparation and the use of active compounds according to the invention are illustrated by the examples below.

PREPARATION EXAMPLES

Example 1

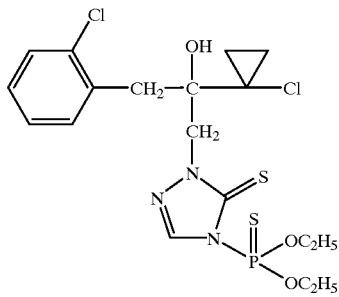

(I-1)

Under an atmosphere of argon and with stirring at room temperature, a solution of 3.45 g (0.02 mol) of diethyl chlorothiophosphate in 40 ml of absolute acetonitrile is slowly added dropwise to a mixture of 6.88 g (0.02 mol) of 2-(1-chloro-cyclopropyl)-1-(2-chlorophenyl)-3-(4,5-dihydro-5-thiono-1,2,4-trizol-1-yl)-propan-2-ol, 5.52 g (0.04 mol) of dried and ground potassium carbonate, a few drops of diazabicyclooctane (DABCO) and 60 ml of absolute acetonitrile. After the addition has ended, the reaction mixture is stirred at room temperature for another 16 hours and then concentrated under reduced pressure. The residue that remains is stirred with 100 ml of water and the resulting mixture is extracted three times with 75 ml of methylene chloride each time. The combined organic phases are dried over sodium sulphate and then concentrated under reduced pressure. This gives 3.17 g of a product which, according to HPLC analysis, comprises 82% of 2-(1-chloro-cyclopropyl)-1-(2-chloro-phenyl)-3-[4,5-dihydro-5-thiono-4-(O,O-diethyl-thiophosphonyl)-1,2,4-triazol-1-yl]-propan-2-ol. Thus, the calculated yield is 63.8% of theory.

NMR spectrum (CDCl$_3$, 162 MHz):

$^{31}$P δ=55.4 ppm

The substances listed in Tables 13 and 14 below are also prepared by the methods mentioned above.

TABLE 13

(Ib)

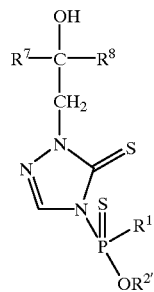

| Ex. No. | R$^7$ | R$^8$ | R$^1$ | R$^{2'}$ | Physical const. |
|---|---|---|---|---|---|
| 2 | ![2-chlorophenyl-CH2]  | ![cyclopropyl-Cl] | —O—CH$_2$—CH$_2$—CH(CH$_3$)—C$_2$H$_5$ with CH$_3$ | | δ = 55.7 ppm*) |

TABLE 13-continued
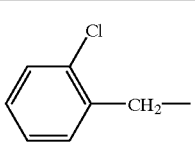
(Ib)
| Ex. No. | R⁷ | R⁸ | R¹ | R²' | Physical const. |
|---|---|---|---|---|---|
| 3 |  | 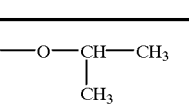 | —O—CH(CH₃)—CH₃ | —C₂H₅ | δ = 53.6 ppm*) |
| 4 | 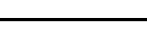 | 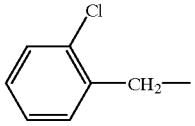 | —O—CH₂—CH₂—OCH₃ | —C₂H₅ | δ = 56.1 ppm*) |
| 5 |  | 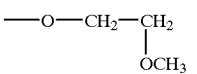 | —CH₃ | —CH(CH₃)—C₂H₅ | δ = 80.4 ppm*) |
| 6 |  | 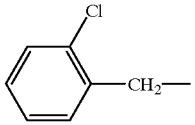 | —C₂H₅ | —C₂H₅ | δ = 91.3 ppm*) |
| 7 |  |  | —NH—CH₃ | —C₂H₅ | δ = 63.7 ppm*) |
| 8 | 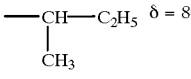 | 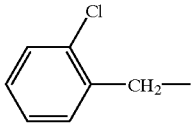 |  | —CH(CH₃)₂ | δ = 68.2 ppm*) |
| 9 |  |  | —O—C₆H₅ | —C₂H₅ | δ = 51.2 ppm*) |
*)In each case, the signal in the ³¹P NMR spectrum (162 MHz, CDCl₃) is stated.

TABLE 14

(Ib)

[Structure of compound Ib]

| Ex. No. | R⁷ | R⁸ | R¹ | R²' | Physical const. |
|---|---|---|---|---|---|
| 10 | 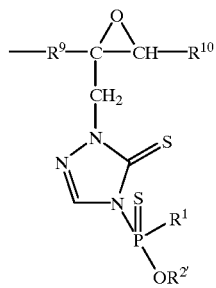 (4-F-C₆H₄-) | (2,6-diCl-C₆H₃-) | —OC₂H₅ | —C₂H₅ | δ = 55.4 ppm*) |
| 11 | (4-F-C₆H₄-) | (2-F-6-CH₃-C₆H₃-) | —OC₂H₅ | —C₂H₅ | δ = 55.4 ppm*) |

*)In each case, the signal in the $^{31}$P NMR spectrum (162 MHz, CDCl$_3$) is stated.

USE EXAMPLES

Example A

Podosphaera test (apple)/protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the causative organism of apple mildew *Podosphaera leucotricha*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

Podosphaera test (apple)/protective

| Active compound | Application rate of active compound in g/ha | Efficacy in % |
|---|---|---|
| According to the invention: | | |
| 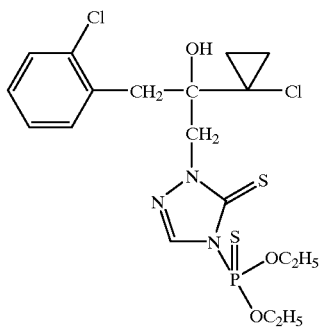 | 50 | 94 |

TABLE A-continued

Podosphaera test (apple)/protective

| Active compound | Application rate of active compound in g/ha | Efficacy in % |
|---|---|---|
| 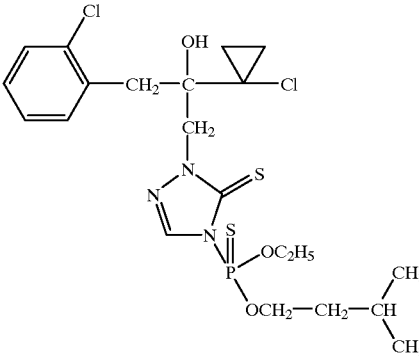 | 50 | 95 |
|  | 50 | 90 |
| 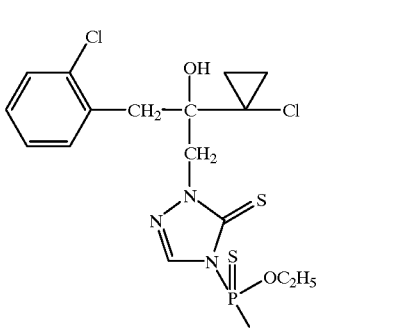 | 50 | 100 |

Example B

Sphaerotheca test (cucumber)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE B

Sphaerotheca test (cucumber)/protective

| Active compound | Application rate of active compound in g/ha | Efficacy in % |
|---|---|---|
| According to the invention: | | |
| (1) | 50 | 93 |

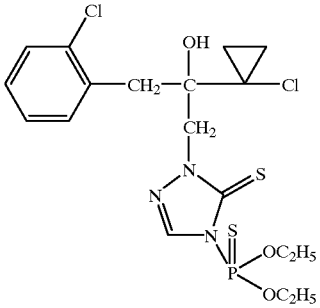

| | | |
|---|---|---|
| (4) | 50 | 95 |

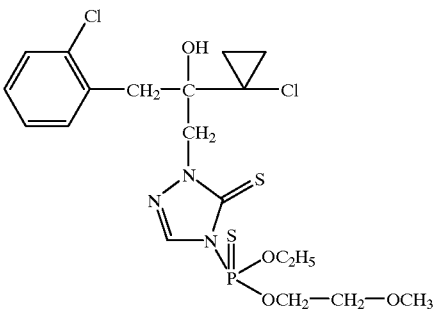

Example C

Venturia test (apple)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab *Venturia inaequalis* and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

Active compounds, application rates and test results are shown in the table below.

TABLE C

Venturia test (apple)/protective

| Active compound | Application rate of active compound in g/ha | Efficacy in % |
|---|---|---|
| According to the invention: | | |
| (1) [structure: 2-chlorobenzyl group attached to C(OH)(CH₂-)(chlorocyclopropyl), with CH₂ linked to N of triazole-thione, N-P(=S)(OC₂H₅)₂] | 50 | 99 |
| (2) [structure: 2-chlorobenzyl-C(OH)(chlorocyclopropyl)-CH₂-triazole-thione-N-P(=S)(OC₂H₅)(OCH₂-CH₂-CH(CH₃)₂)] | 50 | 89 |
| (3) [structure: 2-chlorobenzyl-C(OH)(chlorocyclopropyl)-CH₂-triazole-thione-N-P(=S)(OC₂H₅)(OCH(CH₃)₂)] | 50 | 91 |
| (4) [structure: 2-chlorobenzyl-C(OH)(chlorocyclopropyl)-CH₂-triazole-thione-N-P(=S)(OC₂H₅)(OCH₂-CH₂-OCH₃)] | 50 | 86 |

Example D

Erysiphe test (barley)/curative

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f.sp. *hordei*. 48 hours after the inoculation, the plants are sprayed with the preparation of active compound at the stated application rate.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection if observed.

Active compounds, application rates and test results are shown in the table below.

TABLE D

Erysiphe test (barley)/curative

| Active compound | Application rate of active compound in g/ha | Efficacy in % |
| --- | --- | --- |
| According to the invention: | | |
| [structure] | 250 | 100 |

Example E

Erysiphe test (barley)/protective

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE E

Erysiphe test (barley)/protective

| Active compound | Application rate of active compound in g/ha | Efficacy in % |
| --- | --- | --- |
| According to the invention: | | |
| (1) [structure] | 250 | 100 |

TABLE E-continued

Erysiphe test (barley)/protective

| Active compound | Application rate of active compound in g/ha | Efficacy in % |
| --- | --- | --- |
| (2) [structure] | 250 | 100 |
| (3) [structure] | 250 | 100 |
| (4) [structure] | 250 | 100 |
| (9) [structure] | 250 | 100 |

Example F

Erysiphe test (wheat)/curative

Solvent: 25 parts by weight of N,N-dimethylacetamide
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f.sp. *tritici*. 48 hours after the inoculation, the plants are sprayed with the preparation of active compound at the stated application rate.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE F

Erysiphe test (wheat)/curative

| Active compound | Application rate of active compound in g/ha | Efficacy in % |
| --- | --- | --- |
| According to the invention: | | |
| (1) [structure] | 250 | 100 |

Example G

Erysiphe test (wheat)/protective

Solvent: 25 parts by weight of N,N-dimethylacetamide
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *tritici*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE G

Erysiphe test (wheat)/protective

| Active compound | Application rate of active compound in g/ha | Efficacy in % |
| --- | --- | --- |
| According to the invention: | | |
| (1) [structure] | 250 | 100 |

Example H

Fusarium nivale (var. nivale) test (wheat)/protective

Solvent: 25 parts by weight of N,N-dimethylacetamide
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Fusarium nivale* (var. *nivale*).

The plants are placed in a greenhouse under transparent incubation hoods sat a temperature of approximately 15° C. and a relative atmospheric humidity of approximately 100%.

Evaluation is carried out 4 days after the inoculation. 0% means an efficacy which corresponds to that of the control, whereas an efficacy of 100% means that no infection is observed.

Active compounds, application rates and test results are shown in the table below.

TABLE H

*Fusarium nivale* (var. nivale) test (wheat)/protective

| Active compound | Application rate of active compound in g/ha | Efficacy in % |
|---|---|---|
| According to the invention: | | |
| (1) 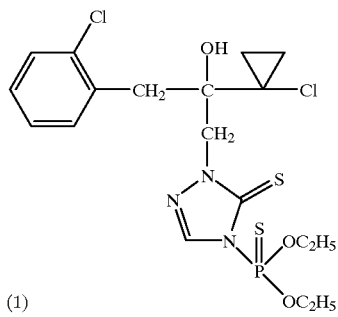 | 250 | 100 |

Example I

Puccinia test (wheat)/curative

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Puccinia recondita*. The plants remain in an incubation cabin at 20° C. and 100% relative atmospheric humidity for 48 hours. The plants are then sprayed with the preparation of active compound at the stated application rate.

The plants are placed in a greenhouse at a temperature of approximately 20° C. and a relative atmospheric humidity of approximately 80% to promote the development of rust pustules.

Evaluation is carried out 10 days after the inoculation. 0% means an efficacy which corresponds to that of the control, whereas an efficacy of 100% means that no infection is observed.

Active compounds, application rates and test results are shown in the table below.

TABLE I

Puccinia test (wheat)/curative

| Active compound | Application rate of active compound in g/ha | Efficacy in % |
|---|---|---|
| According to the invention: | | |
| (1) [same structure as above] | 250 | 100 |

TABLE I-continued
Puccinia test (wheat)/curative
| Active compound | Application rate of active compound in g/ha | Efficacy in % |
|---|---|---|
| (2) 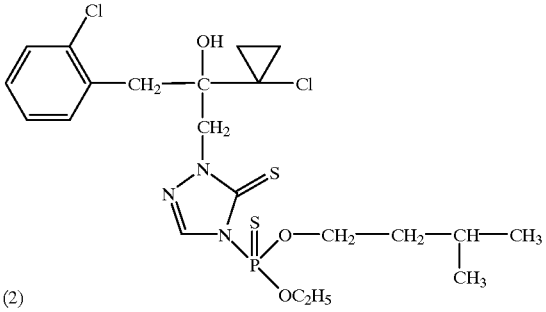 | 250 | 100 |
| (3) 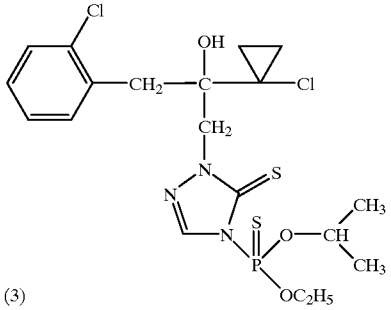 | 250 | 100 |
| (4) 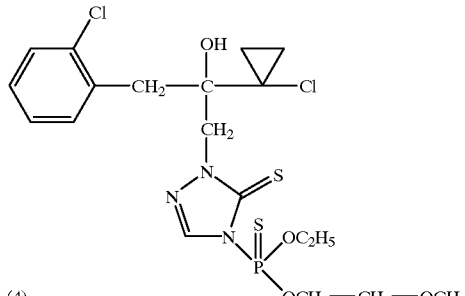 | 250 | 100 |
| (9) 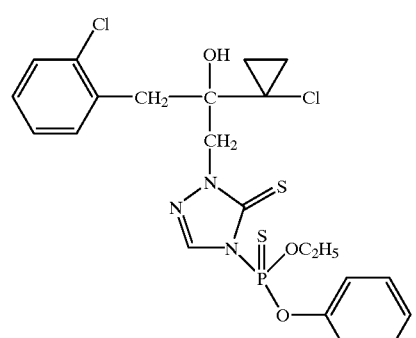 | 250 | 100 |

What is claimed is:

1. A triazolinethione-phosphoric acid derivative of the formula

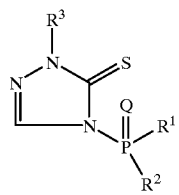 (I)

in which

R¹ represents a moiety selected from the group consisting of straight-chain or branched alkyl having 1 to 6 carbon atoms; cycloalkyl having 3 to 6 carbon atoms; straight-chain or branched alkoxy having 1 to 6 carbon atoms; alkoxyalkoxy having 1 to 4 carbon atoms in each alkoxy moiety; alkoxyalkyl having 1 to 4 carbon atoms in the alkoxy moiety and 1 to 4 carbon atoms in the alkyl moiety;

phenyl which may be mono-to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano:

phenylalkyl having 1 or 2 carbon atoms in the alkyl moiety, wherein the phenyl moiety may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano;

phenoxy which may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano;

phenylalkoxy having 1 or 2 carbon atoms in the alkoxy moiety, wherein the phenyl moiety may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano; and a radical of the formula

wherein

R⁴ represents hydrogen or alkyl having 1 to 4 carbon atoms and

R⁵ is a moiety selected from the group consisting of alkyl having 1 to 6 carbon atoms;

phenylalkyl having 1 to 2 carbon atoms in the alkyl moiety, wherein the phenyl moiety may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano; and phenyl which may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano;

R² represents a moiety selected from the group consisting of straight-chain or branched alkoxy having 1 to 6 carbon atoms, cycloalkoxy having 3 to 6 carbon atoms, alkoxyalkoxy having 1 to 4 carbon atoms in each alkoxy moiety;

phenoxy which may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano; and phenylalkoxy having 1 or 2 carbon atoms in the alkoxy moiety, wherein the phenyl moiety may be mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, phenyl, nitro and cyano; and R³ represents a radical of the formula

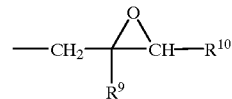

in which

R⁹ represents alkyl having 1 to 4 carbon atoms, halogenoalkyl having to 4 carbon atoms and 1 to 5 halogen atoms, optionally halogen-substituted cycloalkyl having 3 to 7 carbon atoms, naphthyl or represents phenyl which is optionally mono- to trisubstituted by identical or different substituents from the group consisting of halogen, nitro, phenyl, phenoxy, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms, and $R^{10}$ represents phenyl which is optionally mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms.

2. A microbicidal composition comprising a microbiocidally effective amount of one or more triazolinethione-phosphoric acid derivatives of the formula (I) of claim 1 in admixture with an inert diluent.

3. A method for controlling undesirable microorganisms in crop protection and in the protection of materials comprising applying a microbiocidally effective amount of one or more triazolinethione-phosphoric acid derivatives of the formula (I) of claim 1 to the microorganisms and/or their habitat.

4. A triazolinethione-phosphoric acid derivative of the formula

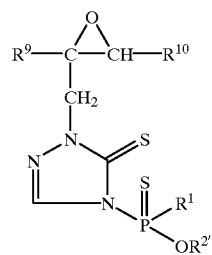

wherein $R^7$ is

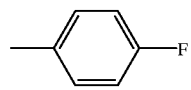

$R^8$ is

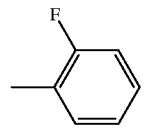

$R^1$ is —$OC_2H_5$, and $R^{2'}$ is —$C_2H_5$.

* * * * *